(12) United States Patent
Romesberg et al.

(10) Patent No.: US 12,281,137 B2
(45) Date of Patent: Apr. 22, 2025

(54) METHOD FOR THE SITE-SPECIFIC ENZYMATIC LABELLING OF NUCLEIC ACIDS IN VITRO BY INCORPORATION OF UNNATURAL NUCLEOTIDES

(71) Applicant: The Scripps Research Institute, La Jolla, CA (US)

(72) Inventors: Floyd E. Romesberg, La Jolla, CA (US); Denis A. Malyshev, Solana Beach, CA (US); Lingjun Li, San Diego, CA (US); Thomas Lavergne, Le Versoud (FR); Zhengtao Li, Pudong new district (CN)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 18/112,952

(22) Filed: Feb. 22, 2023

(65) Prior Publication Data

US 2024/0101590 A1    Mar. 28, 2024

Related U.S. Application Data

(62) Division of application No. 16/518,715, filed on Jul. 22, 2019, now Pat. No. 11,634,451, which is a
(Continued)

(51) Int. Cl.
*C07H 19/24* (2006.01)
*C07H 19/00* (2006.01)
(Continued)

(52) U.S. Cl.
CPC ............. *C07H 19/24* (2013.01); *C07H 19/00* (2013.01); *C07H 21/00* (2013.01); *C07H 21/04* (2013.01);
(Continued)

(58) Field of Classification Search
CPC ........ C07H 19/24; C07H 19/00; C07H 21/00; C07H 21/04
See application file for complete search history.

(56) References Cited

U.S. PATENT DOCUMENTS 3,687,808 A    8/1972   Merigan, Jr. et al.
4,469,863 A    9/1984   Ts'o et al.
(Continued)

FOREIGN PATENT DOCUMENTS

EP    0614907 A1    9/1994
EP    0629633 A2    12/1994
(Continued)

OTHER PUBLICATIONS

Acsadi et al. Human Dystrophin Expression in mdx Mice After Intramuscular Injection of DNA Constructs. Nature 352:815-818 (1991).
(Continued)

*Primary Examiner* — Jezia Riley
(74) *Attorney, Agent, or Firm* — Thomas Fitting

(57) ABSTRACT

Provided herein are analogs of unnatural nucleotides bearing predominantly hydrophobic nucleobase analogs that form unnatural base pairs during DNA polymerase-mediated replication of DNA or RNA polymerase-mediated transcription of RNA. In this manner, the unnatural nucleobases can be introduced in a site-specific way into oligonucleotides (single or double stranded DNA or RNA), where they can provide for site-specific cleavage, or can provide a reactive linker than can undergo functionalization with a cargo-bearing reagent by means of reaction with a primary amino group or by means of click chemistry with an alkyne group of the unnatural nucleobase linker.

35 Claims, 14 Drawing Sheets
Specification includes a Sequence Listing.

Related U.S. Application Data division of application No. 14/910,203, filed as application No. PCT/US2014/050423 on Aug. 8, 2014, now Pat. No. 10,626,138.

(60) Provisional application No. 61/863,649, filed on Aug. 8, 2013.

(51) Int. Cl.
*C07H 21/00* (2006.01)
*C07H 21/04* (2006.01)
*C12N 9/22* (2006.01)
*C12N 15/10* (2006.01)
*C12P 19/34* (2006.01)
*C12Q 1/6832* (2018.01)

(52) U.S. Cl.
CPC ........... *C12N 9/22* (2013.01); *C12N 15/1024* (2013.01); *C12P 19/34* (2013.01); *C12Q 1/6832* (2013.01)

(56) References Cited

U.S. PATENT DOCUMENTS

| | | |
|---|---|---|
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,036,066 A | 7/1991 | Fischer et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,899 A | 1/1997 | Sato et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |

(56) References Cited

U.S. PATENT DOCUMENTS

| | | | |
|---|---|---|---|
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,648,247 A | 7/1997 | Picataggio et al. | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,677,437 A | 10/1997 | Teng et al. | |
| 5,677,439 A | 10/1997 | Weis et al. | |
| 5,681,941 A | 10/1997 | Cook et al. | |
| 5,688,941 A | 11/1997 | Cook et al. | |
| 5,700,920 A | 12/1997 | Altmann et al. | |
| 5,714,331 A | 2/1998 | Buchardt et al. | |
| 5,719,262 A | 2/1998 | Buchardt et al. | |
| 5,750,692 A | 5/1998 | Cook et al. | |
| 5,763,588 A | 6/1998 | Matteucci et al. | |
| 5,830,653 A | 11/1998 | Froehler et al. | |
| 6,005,096 A | 12/1999 | Matteucci et al. | |
| 6,268,490 B1 | 7/2001 | Imanishi et al. | |
| 6,525,191 B1 | 2/2003 | Ramasamy | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 6,955,807 B1 | 10/2005 | Shanafelt et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 7,718,374 B2 | 5/2010 | Belousov et al. | |
| 8,383,792 B2 | 2/2013 | Okamoto et al. | |
| 8,501,805 B2 | 8/2013 | Seth et al. | |
| 8,546,556 B2 | 10/2013 | Seth et al. | |
| 10,626,138 B2 | 4/2020 | Romesberg et al. | |
| 10,696,719 B2 | 6/2020 | Romesberg et al. | |
| 10,696,720 B2 | 6/2020 | Romesberg et al. | |
| 11,466,279 B2 | 10/2022 | Romesberg et al. | |
| 11,634,451 B2 | 4/2023 | Romesberg et al. | |
| 11,879,145 B2 * | 1/2024 | Romesberg | C12P 19/34 |
| 2004/0171570 A1 | 9/2004 | Allerson et al. | |
| 2005/0118623 A1 | 6/2005 | Belousov et al. | |
| 2005/0130923 A1 | 6/2005 | Bhat et al. | |
| 2006/0074035 A1 | 4/2006 | Hong et al. | |
| 2007/0287831 A1 | 12/2007 | Seth et al. | |
| 2008/0039618 A1 | 2/2008 | Allerson et al. | |
| 2008/0300163 A1 | 12/2008 | Cho et al. | |
| 2009/0155844 A1 | 6/2009 | Yokoyama et al. | |
| 2012/0077252 A1 | 3/2012 | Picataggio et al. | |
| 2012/0244112 A1 | 9/2012 | Ast et al. | |
| 2014/0314864 A1 | 10/2014 | Cheng et al. | |
| 2014/0328791 A1 | 11/2014 | Bossard et al. | |
| 2017/0369871 A1 | 12/2017 | Ptacin et al. | |
| 2019/0218257 A1 | 7/2019 | Romesberg et al. | |
| 2019/0376054 A1 | 12/2019 | Ptacin et al. | |
| 2020/0017540 A1 | 1/2020 | Romesberg et al. | |
| 2020/0024597 A1 | 1/2020 | Ptacin et al. | |
| 2020/0131555 A1 | 4/2020 | Ptacin et al. | |
| 2020/0224234 A1 | 7/2020 | Romesberg et al. | |
| 2020/0277342 A1 | 9/2020 | Romesberg et al. | |
| 2020/0318122 A1 | 10/2020 | Romesberg et al. | |
| 2020/0377877 A1 | 12/2020 | Romesberg et al. | |
| 2020/0392550 A1 | 12/2020 | Romesberg et al. | |
| 2021/0222147 A1 | 7/2021 | Ptacin et al. | |
| 2022/0228148 A1 | 7/2022 | Romesberg et al. | |
| 2022/0243244 A1 | 8/2022 | Romesberg et al. | |

FOREIGN PATENT DOCUMENTS

| | | |
|---|---|---|
| EP | 2130835 A1 | 12/2009 |
| JP | 2007510401 A | 4/2007 |
| WO | WO-9213869 A1 | 8/1992 |
| WO | WO-9422890 A1 | 10/1994 |
| WO | WO-9735869 A1 | 10/1997 |
| WO | WO-9831697 A1 | 7/1998 |
| WO | WO-9914226 A2 | 3/1999 |
| WO | WO-9962923 A2 | 12/1999 |
| WO | WO-0023456 A1 | 4/2000 |
| WO | WO-0105801 A1 | 1/2001 |
| WO | WO-0132887 A1 | 5/2001 |
| WO | WO-02062816 A1 | 8/2002 |
| WO | WO-02070533 A2 | 9/2002 |
| WO | WO-03055898 A1 | 7/2003 |
| WO | WO-2004007713 A1 | 1/2004 |
| WO | WO-2004106356 A1 | 12/2004 |
| WO | WO-2005021570 A1 | 3/2005 |
| WO | WO-2005026187 A1 | 3/2005 |
| WO | WO-2005045015 A2 | 5/2005 |
| WO | WO-2006049297 A1 | 5/2006 |
| WO | WO-2007015557 A1 | 2/2007 |
| WO | WO-2007066737 A1 | 6/2007 |
| WO | WO-2007085485 A2 | 8/2007 |
| WO | WO-2007093599 A1 | 8/2007 |
| WO | WO-2007134181 A2 | 11/2007 |
| WO | WO-2008067825 A1 | 6/2008 |
| WO | WO-2008101157 A1 | 8/2008 |
| WO | WO-2008150729 A2 | 12/2008 |
| WO | WO-2008154401 A2 | 12/2008 |
| WO | WO-2009006478 A2 | 1/2009 |
| WO | WO-2009123216 A1 | 10/2009 |
| WO | WO-2011043385 A1 | 4/2011 |
| WO | WO-2011139699 A2 | 11/2011 |
| WO | WO-2015021432 A1 | 2/2015 |
| WO | WO-2016115168 | 7/2016 |
| WO | WO-2017106767 A1 | 6/2017 |
| WO | WO-2017223528 A1 | 12/2017 |
| WO | WO-2019014262 A1 | 1/2019 |
| WO | WO-2019133883 A1 | 7/2019 |
| WO | WO-2021067313 A1 | 4/2021 |
| WO | WO-2022087475 A1 | 4/2022 |

OTHER PUBLICATIONS

Adhikary et al. Adaptive Mutations Alter Antibody Structure and Dynamics During Affinity Maturation. Biochemistry 54(11):2085-93 (2015).

Agris. Decoding the genome: a modified view. Nucleic Acids Res 32:223-238 (2004).

Ambrogelly et al. Pyrrolysine is not hardwired for cotranslational insertion at UAG condons. PNAS 104(9):3141-3146 (2007).

Amiri et al. Deep origin of plastid/parasite ATP/ADP translocases. J. Mol. Evol. 56:137-150 (2003).

Arenas-Ramirez et al. Improved cancer immunotherapy by a CD25-mimobody conferring selectivity to human interleukin-2. Sci Transl Med 8:367ra166 (Nov. 30, 2016). 13 pages.

Arie et al. Phylogenetic identification of n-alkane assimilating Candida yeasts based on nucleotide divergence in the 59 end of LSU rDNA gene. J Gen Appl Microbiol. 46(5):257-262 (2000).

Ast et al. Diatom plastids depend on nucleotide import from the cytosol. PNAS USA 106:3621-3626 (2009).

Beigelman et al. Synthesis of 5'-C-Methyl-D-allo- & L-Talo-ribonucleoside 3'-O-Phosphoramidites & Their Incorporation into Hammerhead Ribozymes. Nucleosides and Nucleotides 14(3-5):901-905 (1995).

Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).

Berger et al. Stability and selectivity of unnatural DNA with five-membered-ring nucleobase analogues. J Am Chem Soc 124(7):1222-6 (2002).

Berger et al. Stable and selective hybridization of oligonucleotides with unnatural hydrophobic bases. Angew Chem Int Ed Engl 39:2940-2942 (2000).

Berger et al. Universal bases for hybridization, replication and chain termination. Nucleic Acids Res 28(15):2911-2914 (2000).

Betz et al. KlenTaq polymerase replicates unnatural base pairs by inducing a Watson-Crick geometry. Nat Chem Biol 8:612-614 (2012).

(56) References Cited

OTHER PUBLICATIONS

Betz et al. Structural insights into DNA replication without hydrogen bonds. J Am Chem Soc 135:18637-18643 (2013).
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bohringer et al. Synthesis of 5'-deoxy-5'-methylphosphonate linked thymidine oligonucleotides. Tet Lett 34:2723-2726 (1993).
Bordo et al. Suggestions for "safe" residue substitutions in site-directed mutagenesis. J Mol Biol 217:721-729 (1991).
Boyman et al. Selective Stimulation of T Cell subsets with Antibody-Cytokine Immune Complexes. Science 311:1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Braasch et al. Locked nucleic acid (LNA): fine-tuning the recognition of DNA and RNA. Chem Bio 8:1-7 (2001).
Branca. Rekindling cancer vaccines. Nat Biotechnol 34(10):1019-1025 (2016).
Cann et al. A heterodimeric DNA polymerase: Evidence that members of Euryarchaeota possess a distinct DNA polymerase. PNAS USA 95:14250 (1998).
Cariello et al. Fidelity of Thermococcus litoralis DNA polymerase (VentTM) in PCR determined by denaturing gradient gel electrophoresis Nucl Acid Res 19:4193-4198 (1991).
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Chastgner et al. Lack of intermediate-affinity interleukin-2 receptor in mice leads to dependence on interkeukin-2 receptor α,β and γ chain expression for T cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Chien et al. Deoxyribonucleic acid polymerase from the extreme thermophile Thermus aquaticus. J Bacteriol 127:1550-1557 (1976).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
Dahl et al. Discovery and validation of a series of aryl sulfonamides as selective inhibitors of tissue-nonspecific alkaline phosphatase (TNAP). J Med Chem 52(21):6919-6925 (2009).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Dranoff. Cytokines in cancer pathogenesis and cancer therapy. Nature Reviews Cancer 4:11-22 (2004).
Dupradeau et al. Differential solvation and tautomer stability of a model base pair within the minor and major grooves of DNA. J Am Chem Soc 127(44):15612-7 (2005).
Egholm et al. PNA hybridizes to complementary oligonucleotides obeying the Watson-Crick hydrogen-bonding rules. Nature 365(6446):566-568 (1993).
El Yacoubi et al. Biosynthesis and function of posttranscriptional modifications of transfer RNAs. Annu Rev Genet 46:69-95 (2012).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Fidanza et al. Functionalization of oligonucleotides by the incorporation of thio-specific reporter groups. In Protocols for Oligonucleotide Conjugates. Protocols for Oligonucleotide Conjugates: Synthesis and Analytical Techniques 26:121-143 (1994).
Fidanza et al. Site-specific labeling of DNA sequences containing phosphorothioate diesters. JACS 114(14):5509-5517 (2002).
Floros et al. Anticancer Cytokines: Biology and Clinical Effects of Interferon-α2, Interleukin (IL)-2, IL-15, IL-21, and IL-12. Semin Oncol 42(4):539-548 (2015).

(56) References Cited

OTHER PUBLICATIONS

Fourrey et al. Photo Rearrangement of Phenyl Selenide Derivatives Access to Selenium Substituted C Nucleosides. Tetrahedron Letters 21:455-458 (1980).
Fourrey et al. S-Nucleoside photorearrangement. Access to pyridine pseudonucleosides. J. Org. Chem. 44(11):1902-1894 (1979).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).

Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Insight-Esprit Study Group et al. Interleukin-2 Therapy in Patients with HIV Infection. N Engl J Med. 361(16):1548-59 (2009).
Ishizuka et al. Site-specific functionalization of RNA molecules by an unnatural base pair transcription system via click chemistry. Chem. Comm. 48:10835-10837 (2012).
Jager et al. Oligonucleotide N-alkylphosphoramidates: synthesis and binding to polynucleotides. Biochemistry 27:7247-7246 (1988).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Kim et al. Stability and polymerase recognition of pyridine nucleobase analogues: role of minor-groove H-bond acceptors. Angew Chem Int Ed Engl 45(46):7809-12 (2006).
Kimoto et al. Generation of high-affinity DNA aptamers using an expanded genetic alphabet. Nat. Biotech. 31(5):453-458 (2013).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).

(56) References Cited

OTHER PUBLICATIONS

Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kranaster et al. Increased single-nucleotide discrimination in allele-specific polymerase chain reactions through primer probes bearing nucleobase and 2'-deoxyribose modifications. Chem Eur J 13(21):6115-6122 (2007).
Krieg et al. Improved IL-2 immunotherapy by selective stimulation of IL-2 receptors on lymphocytes and endothelial cells. PNAS USA 107(26):11906-11911 (Jun. 29, 2010).
Kroschwitz. The Concise Encyclopedia of Polymer Science and Engineering. (pp. 858-859) (1990).
Kubelka et al. Synthesis of 2,6-disubstituted pyridin-3-yl C-2'-deoxyribonucleosides through chemoselective transformations of bromo-chloropyridine C-nucleosides. Org. Biomol. Chem. 11:4702-4718 (2013).
Kumar et al. The First Analogues of LNA (Locked Nucleic Acids): Phosphorothioate LNA and 2'-Thio-LNA. Bioorg Med Chem Lett 8:2219-2222 (1998).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lazear et al. Targeting of IL-2 to cytotoxic lymphocytes as an improved method of cytokine-driven immunotherapy. Oncoimmunology 6(2):e1265721 (2017).
Lecomte et al. Selective Inactivation of the 3' to 5' exonuclease activity of Escherichia coli DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Liu et al. Adding new chemistries to the genetic code. Annu Rev Biochem 79:413-444 (2010).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lou et al. Fixing vascular leak in IL-2 immunotherapy. SciBX 3(27):2 pgs (2010).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).

(56) References Cited

OTHER PUBLICATIONS

Manoharan et al. Oligonucleotide Conjugates: Alteration of the Pharmacokinetic Properties of Antisense Agents. Nucleosides & Nucleotides 14:969-973 (1995).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Merchant et al. Preclinical characterization of IL-2 Superkines engineered with biased CD8+ T cell stimulating properties. Poster (SITC 2018).
Meyers et al. Optimal alignments in linear space. CABIOS 4:11-17 (1989).
Micklefield. Backbone Modification of Nucleic Acids: Synthesis, Structure and Therapeutic Applications. Current Medicinal Chemistry 8:1157-1179 (2001).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Montero et al. Nucleosides de synthese XVI: Sur une synthese selective de divers ribofuranosyl-1-purines. Journal of Heterocyclic Chemistry 15(6):929-935 (1978) (English Abstract).
Morris et al. Synthetic Biology Parts for the Storage of Increased Genetic Information in Cells. ACS Synth Biol 6(10):1834-1840 (2017).
Myers et al. Reverse transcription and DNA amplification by a Thermus thermophilus DNA polymerase. Biochemistry 30:7661-7666 (1991).
Nawrot et al. A novel class of DNA analogs bearing 5'-C-phosphonothymidine units: synthesis and physicochemical and biochemical properties. Oligonucleotides16(1):68-82 (2006).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al. N3'-->P5' Oligodeoxyribonucleotide Phosphoramidates: A New Method of Synthesis Based on a Phosphoramidite Amine-Exchange Reaction. J Org Chem 62:7278-7287 (1997).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nicolini et al. The FAP-IL2v Immunocytokine is a Versatile Combination Partner for Cancer Immunotherapy. Poster (SITC 2018).
Nielsen et al. Sequence-selective recognition of DNA by strand displacement with a thymine-substituted polyamide. Science 254:1497-1500 (1991).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
PCT/US2014/050423 International Search Report and Written Opinion dated Nov. 24, 2014.
PCT/US2016/013095 International Search Report and Written Opinion dated Apr. 27, 2016.
PCT/US2018/041503 International Search Report and Written Opinion dated Nov. 7, 2018.
PCT/US2018/045257 International Search Report and Written Opinion dated Nov. 21, 2018.
Peyrottes et al. Oligodeoxynucleoside phosphoramidates (P-NH2): synthesis and thermal stability of duplexes with DNA and RNA targets. Nucleic Acids Res 24:1841-1848 (1996).
Pfannenstiel et al. A Novel, Individualized Xenograft Model of Cancer Immunotherapy and Tumor Growth Inhibition by ALKS 4230. Poster #P351 (SITC 2017).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Roessler et al. Cooperative interactions between the interleukin 2 receptor α and β chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1:Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).

(56) References Cited

OTHER PUBLICATIONS

Saha et al. 5'-Methyl-DNA—A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Schultz et al. Oligo-2'-fluoro-2'-deoxynucleotide N3'-->P5' phosphoramidates: synthesis and properties. Nucleic Acids Res 24:2966-2973 (1996).
Seo et al. Improved High-Efficiency Organic Solar Cells via Incorporation of a Conjugated Polyelectrolyte Interlayer. JACS 133:8416-8419 (2011).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Sharma et al. NKTR-214 enhances anti-tumor T cell immune responses induced by checkpoint blockade or vaccination. Poster (SITC 2017).
Shea et al. Synthesis, hybridization properties and antiviral activity of lipid-oligodeoxynucleotide conjugates. Nucl. Acids Res 18:3777-3783 (1990).
Shimizu et al. Cell-free translation systems for protein engineering. FEBS J 273:4133-4140 (2006).
Siegel et al. Interleukin-2 Toxicity. J Clin Oncol 9(4):694-704 (1991).
Sierzputowska-Gracz et al. Chemistry and structure of modified uridines in the anticodon, wobble position of transfer RNA are determined by thiolation. J Am Chem Soc 109:7171-7177 (1987).
Sim et al. IL2 Variant Circumvents ICOS+ Regulatory T-cell Expansion and Promotes NK Cell Activation. Cancer Immunol Res. 4(11):983-995 (Nov. 2016).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Sivakumar et al. Comparison of Vascular Leak Syndrome in Mice treated with IL21 or IL2. Comparative Medicine 63(1):13-21 (2013).
Spangler et al. Antibodies to Interleukin-2 Elicit Selective T Cell Subset Potentiation through Distinct Conformational Mechanism. Immunity 42:815-825 (2015).
Srivastava et al. Five- and six-membered conformationally locked 2',4'-carbocyclic ribo-thymidines: synthesis, structure, and biochemical studies. J Am Chem Soc 129(26):8362-8379 (2007).
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al. Inhibition of HIV proliferation in MT-4 cells by antisense oligonucleotide conjugated to lipophilic groups. Biochimie 75:49-54 (1993).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Takai et al. A single uridine modification at the wobble position of an artificial tRNA enhances wobbling in an *Escherichia coli* cell-free translation system. FEBS Lett 447(1):1-4 (1999).
Tapp et al. Homogeneous scoring of single-nucleotide polymorphisms: comparison of the 5'-nuclease TaqMan assay and Molecular Beacon probes. Biotechniques 28(4):732-738 (2000).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 14/910,203 Office Action dated Feb. 5, 2019.
U.S. Appl. No. 14/910,203 Office Action dated Sep. 13, 2018.
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/518,715 Office Action dated Apr. 26, 2022.
U.S. Appl. No. 16/518,715 Office Action dated Jul. 10, 2020.
U.S. Appl. No. 16/518,715 Office Action dated May 7, 2021.
U.S. Appl. No. 16/518,715 Office Action dated Oct. 14, 2021.
U.S. Appl. No. 16/518,715 Office Action dated Sep. 10, 2020.
U.S. Appl. No. 16/530,742, filed Aug. 2, 2019.
U.S. Appl. No. 16/546,097, filed Aug. 20, 2019.
U.S. Appl. No. 16/546,100, filed Aug. 20, 2019.
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
U.S. Appl. No. 16/900,154, filed Jun. 12, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Vanbrunt et al. Genetically Encoded Azide Containing Amino Acid in Mammalian Cells Enables Site-Specific Antibody—Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fc-mediated depletion of regulatory T-cells. Nat Comm 8:15373 (2017).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).

(56) References Cited

OTHER PUBLICATIONS

Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wandry et al. Probing unnatural amino acid integration into enhanced green fluorescent protein by genetic code expansion with a high-throughput screening platform. J Biol Eng. 10:11 (2016).
Wang et al. Biophysical and biochemical properties of oligodeoxynucleotides containing 4'-C- and 5'-C-substituted thymidines. Bioorg Med Chem Lett 9:885-890 (1999).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, β, and γc Receptors. Science 310:1159-63 (2005).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Yamashige et al. Highly specific unnatural base pair systems as a third base pair for PCR amplification. Nucleic Acids Res. 40:2793-2806 (2012).
Yu et al. Polymerase recognition of unnatural base pairs. Angew Chem Int Ed Engl 41(20):3841-4 (2002).
Zalevsky. Jefferies 2016 Global Healthcare Conference. PowerPoint presentation (Nov. 16, 2016).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Semisynthetic Organisms with Expanded Genetic Codes. Biochemistry 57:2177-2178 (2018).
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).

\* cited by examiner

β7

β7a

β7b

β8

β8a

β8b

β8a

TPT3^pa

TPT3^co

**Figure 14
Continued**

| | | β5a | β5b | TPT1 | FPT1 | β6b |
|---|---|---|---|---|---|---|
| Round 3 | | | | | | |
| α1 | a | 91 | 84 | | | 90 |
| | b | | | | | |
| α2 | cI | 88 | 71 | | 63 | 55 |
| | cII | 97 | 88 | | 69 | 78 |
| α6 | TOK587 | 88 | 87 | | | 84 |
| | TOK588 | | | | | |
| | TOK576 | 53 | 73 | | | 54 |
| α7 | a | | | | | 78 |
| | PhMO | | | | | 52 |
| | b | | | | | 79 |
| | PMO3 | | | | | 61 |
| α8 | FuMO1 | | | | | 85 |
| | FuMO2 | | | | | 79 |
| | TpMO1 | | | | | 77 |
| | TpMO2 | | | | | 62 |
| α9 | a | 98 | 93 | | | 96 |
| | b | 92 | 78 | | | 91 |
| | c | 96 | 94 | | 73 | 99 |
| α10 | aI | 99 | 88 | | 90 | 94 |
| | aII | 97 | 88 | | 56 | 94 |
| | NOPy | | | | | |
| | NMO | 88 | 66 | | | 96 |
| | c | 99 | 92 | 71 | 88 | 95 |
| α12 | a | 88 | 77 | | | 88 |
| | QMO | 88 | 78 | | | 88 |
| | b | 100 | 86 | | 71 | 99 |
| | TfMO | 93 | 77 | | 64 | 97 |
| | CNMO | 78 | 74 | | | 97 |

| | | β5a | β5b | FPT1 | β6b |
|---|---|---|---|---|---|
| Round 4 | | | | | |
| α1 | DMN | | | | |
| | 2MN | 93 | 76 | | 91 |
| α2 | MMO1 | | | | |
| | MM1 | 76 | 96 | | 65 |
| | DM5 | | | | |
| | DM2 | 100 | 91 | | 76 |
| α6 | TOK587 | 93 | 92 | | 93 |
| | TOK576 | | 73 | | |
| α7 | PyMO1 | | | | 77 |
| | PyMO2 | | | | 80 |
| | PMO1 | | | | 67 |
| | PMO2 | | | | 76 |
| α8 | FuMO1 | | | | 88 |
| | FuMO2 | | | | 91 |
| | TpMO1 | | | | 84 |
| α9 | FlMO | 99 | 98 | | 100 |
| | IMO | 99 | 97 | | 100 |
| | FEMO | 100 | 100 | | 100 |
| | b | 100 | 98 | | 97 |
| | c | 100 | 99 | | 100 |
| α10 | MMO2 | 99 | 88 | 70 | 91 |
| | 2OMe | 100 | 84 | 93 | 81 |
| | DMO | 98 | 88 | | 94 |
| | TMO | 96 | 76 | | 95 |
| | NOPy | | | | |
| | NMO | 84 | 76 | | 100 |
| | 5FM | 100 | 88 | 74 | 94 |
| | NaM | 99 | 96 | 100 | 100 |
| α12 | FDMO | 88 | | | 63 |
| | VMO | 99 | 76 | | 100 |
| | ZMO | 100 | 95 | | 98 |
| | CIMO | 100 | 95 | | 98 |
| | TfMO | 99 | 76 | | 100 |
| | QMO | 93 | 93 | | 94 |
| | CNMO | 88 | 63 | | 98 |

**Figure 14
Continued**

METHOD FOR THE SITE-SPECIFIC ENZYMATIC LABELLING OF NUCLEIC ACIDS IN VITRO BY INCORPORATION OF UNNATURAL NUCLEOTIDES

CROSS-REFERENCE TO RELATED APPLICATIONS

This application is a divisional of U.S. patent application Ser. No. 16/518,715, filed Jul. 22, 2019, which is a divisional of U.S. patent application Ser. No. 14/910,203, filed Feb. 4, 2016; which is a U.S. National Stage Entry of PCT/US2014/050423, filed Aug. 8, 2014; which claims the benefit of priority to U.S. Provisional Patent Application No. 61/863,649, filed Aug. 8, 2013; all of which are herein incorporated by reference in their entirety.

STATEMENT OF GOVERNMENT SUPPORT

This invention was made with government support under GM060005, awarded by the National Institutes of Health. The U.S. government has certain rights in the invention.

SEQUENCE LISTING

The instant application contains a Sequence Listing which has been submitted electronically in XML format and is hereby incorporated by reference in its entirety. Said XML copy, created on Nov. 6, 2023, is named "PAT20068-US-PCD2.xml" and is 20,275 bytes in size.

BACKGROUND

Oligonucleotides and their applications have revolutionized biotechnology. However, the oligonucleotides including both DNA and RNA each includes only the four natural nucleotides of adenosine (A), guanosine (G), cytosine (C), thymine (T) for DNA, and the four natural nucleotides of adenosine (A), guanosine (G), cytosine (C), and uridine (U) for RNA, and which significantly restricts the potential functions and applications of the oligonucleotides.

The ability to sequence-specifically synthesize/amplify oligonucleotides (DNA or RNA) with polymerases, for example by PCR or isothermal amplification systems (e.g., transcription with T7 RNA polymerase), has revolutionized biotechnology. In addition to all of the potential applications in nanotechnology, this has enabled a diverse range of new technologies such as the in vitro evolution via SELEX (Systematic Evolution of Ligands by Exponential Enrichment) of RNA and DNA aptamers and enzymes. See, for example, Oliphant A R, Brandl C J & Struhl K (1989), Defining the sequence specificity of DNA-binding proteins by selecting binding sites from random-sequence oligonucleotides: analysis of yeast GCN4 proteins, *Mol. Cell Biol.*, 9:2944-2949; Tuerk C & Gold L (1990), Systematic evolution of ligands by exponential enrichment: RNA ligands to bacteriophage T4 DNA polymerase, *Science*, 249:505-510; Ellington A D & Szostak J W (1990), In vitro selection of RNA molecules that bind specific ligands, *Nature*, 346:818-822.

Unfortunately, these applications are restricted by the limited chemical/physical diversity present in the natural genetic alphabet (the four natural nucleotides A, C, G, and T in DNA, and the four natural nucleotides A, C, G, and U in RNA). There is accordingly much interest in techniques that would enable the enzymatic synthesis/amplification of oligonucleotides site-specifically labeled with functional groups not present among the nucleotides of the natural genetic alphabet. Currently, the options available for site-specific nucleic acid derivatization include solid-support based chemical synthesis, combined chemical/enzymatic synthesis, and end-labeling procedures. End-labeling procedures are limited to the oligonucleotide termini, and chemical synthesis is limited to short oligonucleotides (<200 nucleotides for DNA and <70 nucleotides for RNA). Enzymatic functionalization is dependent upon enzymatic recognition of the modification of interest and more problematically it is not site-specific.

SUMMARY

The compositions and methods described herein are based on the expansion of the genetic alphabet in vitro, and provide site-specific incorporation of unnatural nucleotides as described herein, bearing reactive linkers adapted to react with cargo reagents comprising groups of complementary reactivity, or linkers bearing cargos bonded thereto, into any position of any DNA or RNA sequence, for example, by using standard PCR or isothermal transcription methodologies.

In various embodiments, the linkers are attached to a cargo at the nucleotide triphosphate stage, thus allowing for the direct production of the desired site-specifically labeled oligonucleotide, e.g., by automated polynucleotide synthesis machines such as phosphoroamidite polynucleotide synthesis machines.

The linkers, in other embodiments, include a reactive center (e.g., primary amine, alkyne, thiol, aldehyde, or azide), providing a reactive linker, allowing for the site-specific modification of the DNA or RNA oligonucleotide after its synthesis. This can be accomplished using a cargo reagent comprising a cargo (e.g., molecule, liposome, nanoparticle, etc.) and a group of reactivity complementary to the reactive center of the reactive linker moiety. In some embodiments, the reactive center of the linker moiety is protected with a standard protecting group. Reaction of a nucleobase disclosed herein bearing a reactive linker (after deprotection, if required), and a cargo reagent incorporating a cargo and a group of complementary reactivity to the reactive linker, serves to provide a nucleobase linked to a cargo via a coupled linker moiety.

The compositions of this disclosure, in various embodiments, enable the expansion of the limited repertoire of functionality of the four natural DNA nucleotides and of the four natural RNA nucleotides to include virtually any functionality of interest, site-specifically incorporated into a DNA or RNA oligonucleotide or into a DNA analog or an RNA analog, such as a PNA or an LNA or the like. The cargo optionally includes functionality to enable altered molecular recognition (i.e. for the development of aptamers), altered reactivity (including for catalysis), and/or probes for visualization and/or characterization (i.e. for the development of diagnostics).

Provided herein, in various embodiments, is a compound comprising a nucleobase analog of any of the following formulas β8a or β8b:

β8a

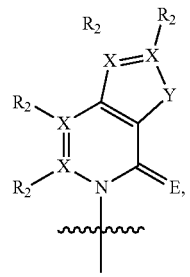

β8b

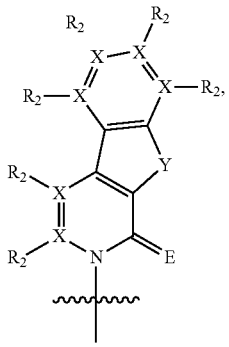

wherein each X is independently carbon or nitrogen; wherein each R₂ is optional and when present is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently sulfur, selenium or oxygen; and wherein the nucleobase analog is not 4TFP or 7TFP or a linker-derivatization thereof.

Provided herein, in various embodiments, is a compound comprising a nucleobase analog of any of the following formulas:

α14a

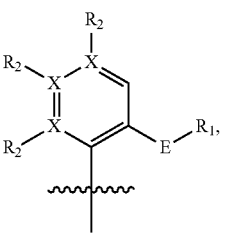

α14b

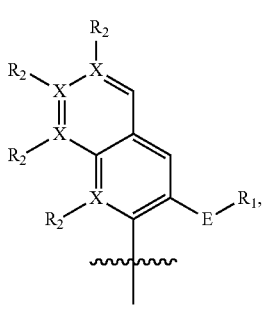

α14c

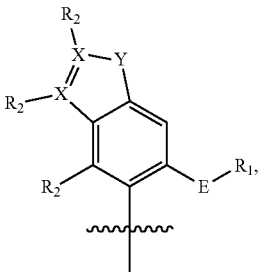

α14d

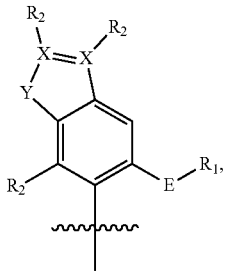

α14e

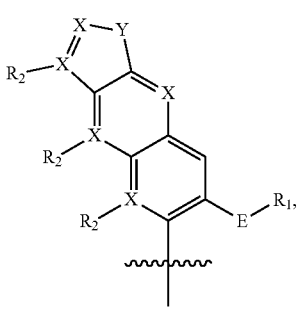

α14f

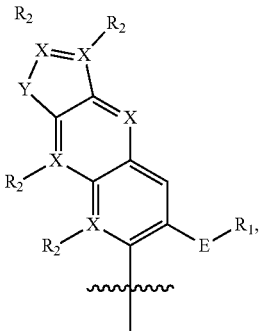

wherein each X is independently carbon or nitrogen; wherein each R₁ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each R₂ is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each Y is independently sulfur, oxygen, selenium, or secondary amine; wherein each E is independently sulfur, selenium or oxygen; and wherein the nucleobase analog is not FIMO, MIMO, FEMO, PrMO, EMO, MEMO, IMO, MMO2, DMO, NMO, 5FM, 2OMe, TMO, FDMO, VMO, ZMO, CIMO, TfMO, CNMO, NaM, or QMO.

Here and throughout, the wavy line indicates a point of attachment to a ribosyl, deoxyribosyl, or dideoxyribosyl moiety; or to an analog of a ribosyl, deoxyribosyl, or dideoxyribyl moiety, such as a locked ribose analog, a peptide group, or the like. In some embodiments, the ribosyl, deoxyribosyl, or dideoxyribosyl moiety or analog thereof is in free form, connected to a mono-phosphate, diphosphate, or triphosphate group; optionally comprising an α-thiotriphosphate, β-thiophosphate, or γ-thiophosphate group; or is included in an RNA or a DNA or in an RNA analog or a DNA analog.

In some embodiments, when referring to either a ribosyl moiety or deoxyribosyl moiety of an unnatural nucleobase provided herein X, dX or (d)X is used, for example, dTPT3 or (d)TPT3 refers to the TPT3 nucleobase bonded to any of the options at the position indicated by the wavy line. Thus, the general appellation of dX refers to compounds having ribose or deoxyribose analogs bonded thereto as indicated by the wavy line. When specifically referring to a ribosyl nucleoside, the prefix "d" is dropped, i.e., TPT3 refers to a ribosyl form. When incorporated into a triphosphate polymerase substrate, (i.e. TPT3TP, dTPT3TP), the nucleotide, or linker-derivatized variants, is considered to be incorporated into an RNA or DNA oligonucleotide using an RNA or DNA polymerase, respectively.

In some embodiments, a ribosyl, deoxyribosyl, or dideoxyribosyl analog of a nucleoside analog provided (e.g., β8a, β8b, α14a, α14b, α14c, α14d, α14e, α14f) comprises a 2' functional group. Examples of functional groups include, without limitation, methoxy, halogen, —O-allyl, —O-methoxyethyl, primary amine, —O-dinitrophenol, —O-dinitrophenyl ether, alkyl, —O-alkyl, thiol, aminoethoxymethyl, aminopropoxymethyl, aminoethyl, cyanoethyl, and guanidinoethyl groups. In some embodiments, the ribosyl, deoxyribosyl, or dideoxyribosyl analog comprises a 4'-thio substitution (e.g., the oxygen of the sugar moiety is replaced with a sulfur).

In some embodiments, an alkyl group of a nucleobase analog includes, without limitation, a methyl, ethyl, propyl, and isopropyl group. In some embodiments, a halogen group of a nucleobase analog includes, without limitation, fluorine, chlorine, bromine, and iodine.

In some embodiments, a reactive linker of a nucleobase analog comprises a functional group including, but not limited to, alkyl, alkenyl, alkynyl, phenyl, benzyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, imide, azide, azo, cyanate, isocyanate, nitrate, nitrile, isonitrile, nitrosooxy, nitro, nitroso, pyridyl, sulfhydryl, sulfide, disulfide, sulfinyl, sulfo, thiocyanate, isothiocyanante, carbonothioyl, phoshino, phosphono, phosphate, borono, boronate, borino, borinate, and a combination thereof. In some embodiments, a reactive linker of a nucleobase analog comprises an amino group, an acetylenic group, a thiol group, an aldehyde group, or an azide group.

In some embodiments, a ribosyl or deoxyribosyl moiety comprises a triphosphate or an α-thiotriphosphate group bonded to a 5'-hydroxyl thereof. In some embodiments, a ribosyl or deoxyribosyl moiety is incorporated into a RNA or DNA oligonucleotide chain, respectively, or the ribosyl or deoxyribosyl moiety or analog thereof is incorporated into an RNA or a DNA analog. The RNA analog or DNA analog, in certain embodiments, is a peptide nucleic acid (PNA) or a locked nucleic acid (LNA). The RNA analog or DNA analog, in certain embodiments, is a bicyclic derivative. Bicyclic derivatives include, without limitation, 2'-O,4'-C-ethylene-bridged nucleic acid (ENA), carbocyclic locked nucleic acid (CLNA), cyclohexene nucleic acid (CENA), and 2'-deoxy-2'-N,4'-C-ethylene-locked nucleic acid (AENA). In certain embodiments, the RNA analog or the DNA analog is an acyclic derivative. In certain embodiments, the RNA analog or the DNA analog is an unlocked nucleic acid (UNA). In certain embodiments, the RNA analog or the DNA analog comprises a pyranose ring instead of a ribose. In certain embodiments, the RNA analog or the DNA analog is an arabino nucleic acid (ANA) or a hexitol nucleic acid (HNA).

In some embodiments, a ribosyl or deoxyribosyl moiety or analog thereof is substituted with protecting and activating groups suitable for use in an automated chemical oligonucleotide synthesis machine. An example of an automated chemical oligonucleotide synthesis machine is a phosphoroamidite synthesis machine.

In some embodiments, at least one R2 of a nucleobase analog independently comprises a —CC≡CH2NHR3 group, wherein R3 is hydrogen or is an amino-protecting group. An example of an amino-protecting group is a dichloroacetyl group. In some embodiments, at least one R2 of a nucleobase analog independently comprises an acetylenic group suitable for use in a click reaction with a cargo reagent comprising a cargo and an acetylene-reactive group. In some embodiments, at least one R2 of a nucleobase analog independently comprises a thiol group suitable for use in a reaction with a cargo reagent comprising a cargo and a thiol-reactive group. In some embodiments, at least one R2 of a nucleobase analog independently comprises an aldehyde group suitable for use in a reaction with a cargo reagent comprising a cargo and an aldehyde-reactive group. In some embodiments, at least one R2 of a nucleobase analog independently comprises an azide group suitable for use in a reaction with a cargo reagent comprising a cargo and an azide-reactive group. In some embodiments, at least one R2 of a nucleobase analog independently comprises —CC≡(CH2)n-C≡CH, wherein n is 1, 2, 3, 4, 5, or 6; or R2 is —C≡C—(CH2)n1-O—(CH2)n2-C≡CH, wherein n1 and n2 are each independently 1, 2, or 3. In some embodiments, at least one R2 is independently a coupled linker bonded to a cargo by reaction of an amino group and an amino-reactive group. An example of an amino-reactive group is an acylating group or an alkylating group, or is an N-hydroxysuccinimide ester. In some embodiments, at least one R2 is independently a coupled linker bonded to a cargo by reaction of an acetylene group and an acetylene-reactive group. An example of an acetylene-reactive group is an azide group. In certain embodiments, the acetylene group and the azide group are coupled with a copper-catalyzed click reaction. In some embodiments, at least one R2 is independently a coupled linker bonded to a cargo by reaction of a thiol and a thiol-reactive group. In some embodiments, at least one R2 is independently a coupled linker bonded to a cargo by reaction of an aldehyde and an aldehyde-reactive group. In some embodiments, at least one R2 is independently a coupled linker bonded to a cargo by reaction of an azide and an azide-reactive group. An example of an azide-reactive group is a terminal alkyne or a strained cyclooctyne. In some embodiments, at least one R2 is independently hydrogen, the compound comprising an α-thiotriphosphate group, wherein a cargo reagent comprising a γ-bromo-α,β-unsaturated carbonyl, iodo, bromoacetyl, or aziridinylsulfonamide group is coupled thereto.

In some embodiments, a cargo of a nucleobase analog includes, without limitation, proteins, peptides, amino acids, oligonucleotides, small molecule drugs, aliphatic groups, compounds comprising photoreactive groups, compounds comprising chemically-reactive groups, compounds comprising catalytic groups, compounds comprising chloromethylketones, lipids, biotin, fluorescent compounds, fluorescence quenching compounds, liposomes, and nanoparticles.

Further provided herein, in various embodiments, is the nucleobase analog

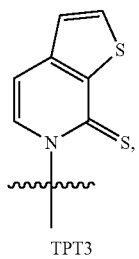

TPT3 and derivatives and analogs thereof.

Further provided herein, in various embodiments, is the nucleobase analog

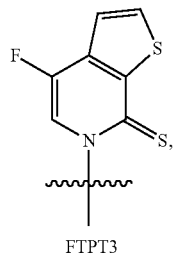

FTPT3 and derivatives and analogs thereof.

Further provided herein, in various embodiments, is the nucleobase analog

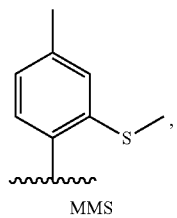 [SMILES: *c1ccc(C)cc1SC]

MMS and derivatives and analogs thereof.

Further provided herein, in various embodiments, is the nucleobase analog

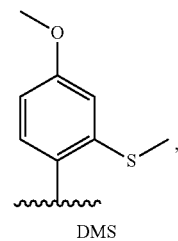 [SMILES: *c1ccc(OC)cc1SC]

DMS and derivatives and analogs thereof.

Further provided herein, in various embodiments, is the nucleobase analog

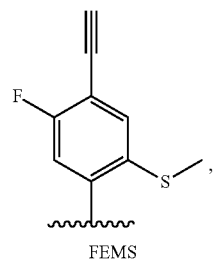 [SMILES: *c1cc(F)c(C#C)cc1SC]

FEMS and derivatives and analogs thereof.

Further provided herein, in various embodiments, is the nucleobase analog

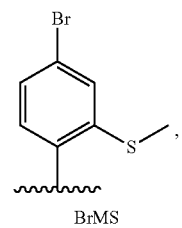 [SMILES: *c1ccc(Br)cc1SC]

BrMS and derivatives and analogs thereof.

Further provided herein, in various embodiments, is the nucleobase analog

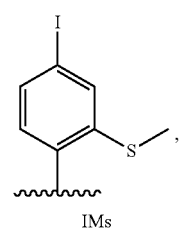 [SMILES: *c1ccc(I)cc1SC ; "IMs"]

IMs and derivatives and analogs thereof.

Provided herein, in some embodiments, are nucleobase pairs comprising a first nucleobase analog having any of the formulas β9a or β9b; and a second nucleobase analog having any of the formulas α15a or α15b:

d5SICS-dMMO2, d5SICS-dDMO, d5SICS-dNMO, d5SICS-d5FM, d5SICS-d2OMe, d5SICS-dTMO, d5SICS-dFDMO, d5SICS-dVMO, d5SICS-dZMO, d5SICS-dClMO, d5SICS-dTfMO, and d5SICS-dCNMO.

Provided herein, in some embodiments, is a nucleobase pair comprising a first nucleobase analog having the formula β9b, and a second nucleobase analog having any of the formulas α15a or α15b:

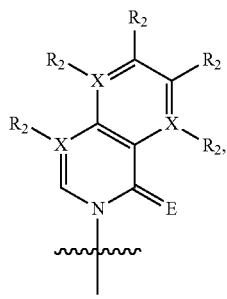

β9a

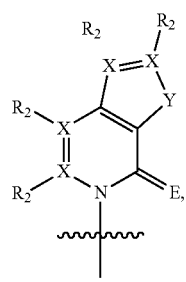

β9b

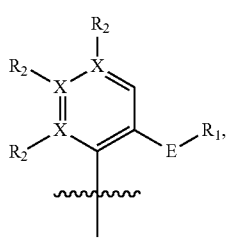

α15a

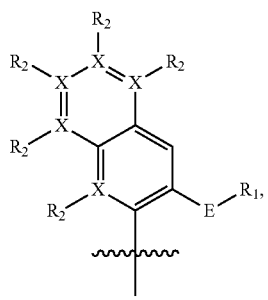

α15b

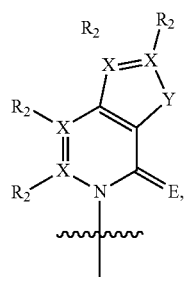

β9b

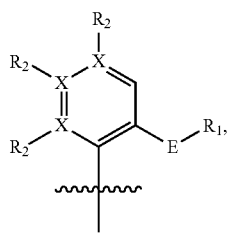

α15a

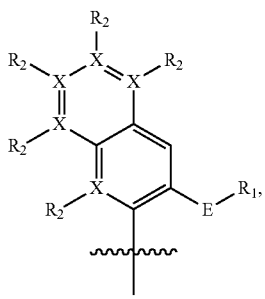

α15b wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently oxygen, sulfur or selenium; and wherein the nucleobase pair is not dICS-dMMO2, dICS-2OMe, dSICS-dMMO2, dSICS-d2OMe, dSNICS-dMMO2, dSNICS-d2OMe, d4SICS-dMMO2, d4SICS-d2OMe, d5SICS-dFIMO, d5SICS-dMIMO, d5SICS-dFEMO, d5SICS-dPrMO, d5SICS-dEMO, d5SICS-dMEMO, d5SICS-dIMO, wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; and wherein each E is independently oxygen, sulfur or selenium.

Provided herein, in some embodiments, is a nucleobase pair comprising a first nucleobase analog having any of the formulas β9a or β9b, and a second nucleobase analog having any of the formulas α16a or α16b:

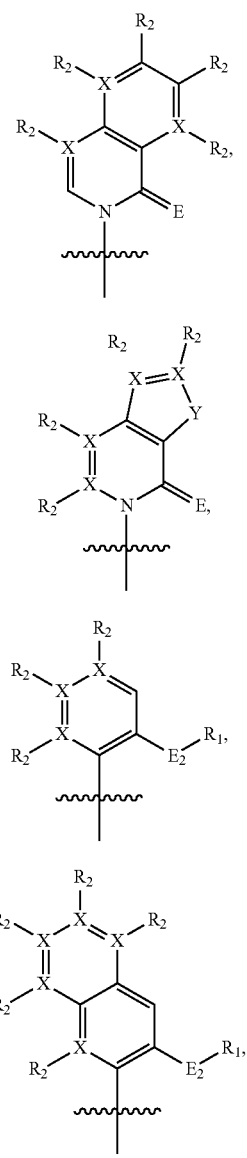

β9a

β9b

α16a

α16b wherein each X is independently carbon or nitrogen; wherein each R₁ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each R₂ is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently oxygen, sulfur or selenium; and wherein each E₂ is independently sulfur or selenium.

The wavy line indicates a point of attachment to a ribosyl, deoxyribosyl, or dideoxyribosyl moiety; or to an analog of a ribosyl, deoxyribosyl, or dideoxyribyl moiety, such as a locked ribose analog, a peptide group, or the like. In some embodiments, the ribosyl, deoxyribosyl, or dideoxyribosyl moiety or analog thereof is in free form, connected to a mono-phosphate, diphosphate, or triphosphate group; optionally comprising an α-thiotriphosphate, β-thiophosphate, or γ-thiophosphate group; or is included in an RNA or a DNA or in an RNA analog or a DNA analog.

In some embodiments, an alkynyl group is an ethynyl or a propynyl group. In some embodiments, an alkyl group is a methyl, ethyl, propyl, or isopropyl group. In some embodiments, a halogen is fluorine, chlorine, bromine, or iodine.

In some embodiments, a ribosyl, deoxyribosyl, or dideoxyribosyl analog of the nucleobase pair comprises a 2′ functional group. Exemplary functional groups include, without limitation, methoxy, halogen, —O-allyl, —O-methoxyethyl, primary amine, alkyl, —O-alkyl, thiol, —O-dinitrophenol, —O-dinitrophenyl ether, aminoethoxymethyl, aminopropoxymethyl, aminoethyl, cyanoethyl, and guanidinoethyl groups. In some embodiments, a ribosyl, deoxyribosyl, or dideoxyribosyl analog of the nucleobase pair comprises a 4′-thio substitution.

In some embodiments, a nucleobase pair comprises a nucleobase having the formula α15b. In some embodiments, a nucleobase pair comprises a nucleobase having the formula α15a.

In some embodiments, a nucleobase pair comprises a nucleobase having the formula β9b. In some embodiments, a nucleobase pair comprises a nucleobase having the formula β9b, wherein each X is carbon, Y is sulfur, each R2 is hydrogen, and E is sulfur. In some embodiments, a nucleobase pair comprises a nucleobase having the formula α15b, wherein each X is carbon, each R2 is hydrogen, R1 is a methyl group, and E is oxygen. In some embodiments, a nucleobase pair comprises a first nucleobase analog having the formula β9a and a second nucleobase analog having the formula alba. In some embodiments, a nucleobase pair comprises a first nucleobase analog having the formula β9a and a second nucleobase analog having the formula α16b. In some embodiments, a nucleobase pair comprises a first nucleobase analog having the formula β9b and a second nucleobase analog having the formula alba. In some embodiments, a nucleobase pair comprises a first nucleobase analog having the formula β9b and a second nucleobase analog having the formula α16b.

Provided herein, in certain embodiments, is a nucleobase pair comprising a first nucleobase analog having the formula β9b and a second nucleobase analog having the formula β9b:

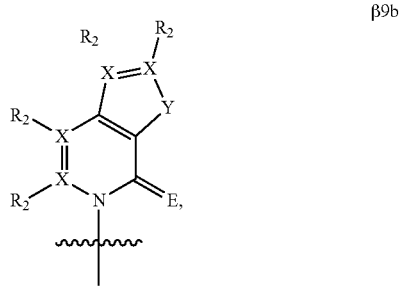

β9b wherein each X is independently carbon or nitrogen; wherein each R₂ is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; and wherein each E is independently oxygen, sulfur or selenium. In some embodiments, the nucleobase pair is a homo-nucleobase pair.

Provided herein, in certain embodiments, is a nucleobase pair comprising a first nucleobase analog having the formula α16a and a second nucleobase analog having the formula α16a:

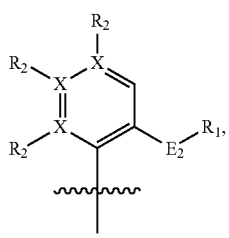

α16a wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; and wherein each $E_2$ is independently sulfur or selenium. In some embodiments, the nucleobase pair is a homo-nucleobase pair.

Provided herein, in certain embodiments, is a nucleobase pair comprising a first nucleobase analog having the formula α16b and a second nucleobase analog having the formula α16b:

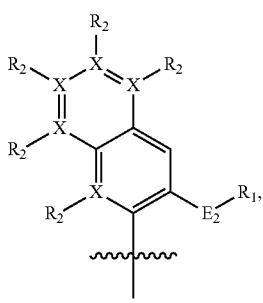

α16b wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present is independently hydrogen, alkyl, alkenyl, alkynyl, methoxy, methanethiol, methaneseleno, halogen, cyano, azide, nitro group, a reactive linker com- prising a reactive center adapted to bond to a cargo reagent comprising a cargo and a group of reactivity complementary to the reactive center, or a coupled linker to which a cargo is bonded; and wherein each $E_2$ is independently sulfur or selenium. In some embodiments, the nucleobase pair is a homo-nucleobase pair.

Provided herein, in certain embodiments, is a nucleobase pair comprising a first nucleobase analog having any of the formulas β9a, β9b, α15a, α15b, α16a, or α16b; and a second nucleobase selected from the group consisting of cytosine, guanine, adenine, thymine, uracil, 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

A base pair comprising one or more unnatural nucleobases is exemplified by the dTPT3PA-dNaM unnatural base pair (i.e. the pair formed between dTPT3PA and dNaM;

FIG. 1A and 1B). In addition, the orthogonal reactivity of the different reactive centers/linkers developed (i.e. phosphorothioates, amines, and alkynes) allows for the selective arraying of different moieties to the same oligonucleotide (DNA or RNA). Another composition is further exemplified by the dTPT3PA-dMMO2pCO unnatural base pair, wherein, in various embodiments, the alkynyl group of dMMO2pCO is used to attach one functional group via Copper(I)-catalyzed Azide-Alkyne Cycloaddition (CuAAC) and, after deprotection of dTPT3PA, the free amine is used to attach a different functional group via N-hydroxysuccinimide (NETS) coupling.

While several other unnatural base pairs have been reported and derivatized with linkers, the linker-derivatized pairs described here, dTPT3PA-dNaM, d5SICSCO-dNaM, dTPT3PA-dMMO2pCO (FIG. 2), are both more validated and are better replicated within DNA and better transcribed into RNA. In particular, dTPT3PA-dNaM, is well replicated and thus is suitable for use in practicing the methods disclosed and claimed herein.

Provided herein are unnatural base pairs comprising dTPT3, wherein dTPT3 in some instances, is linker-derivatized. Unnatural base pairs comprising dTPT3 or linker-derivatized dTPT3 (e.g., dTPT3PA) include, without limitation, dTPT3-MMS, dTPT3-DMS, dTPT3-FEMS, dTPT3-BrMS, dTPT3-IMS, dTPT3-dDMN, dTPT3-d4OMe, dTPT3-dIQ, dTPT3-d2MN, dTPT3-d3OMe, dTPT3-dQL, dTPT3-d2Np, dTPT3-dDM4, dTPT3-dDM, dTPT3-dBEN, dTPT3-d3FB, dTPT3-dMM1, dTPT3-dMMO1, dTPT3-dDM2, dTPT3-dDM5, dTPT3-d2Py, dTPT3-d5MPy, dTPT3-dEPy, dTPT3-d3MPy, dTPT3-d34DMPy, dTPT3-d45DMPy, dTPT3-d4MPy, dTPT3-d35DMPy, dTPT3-dBP, dTPT3-dBTp, dTPT3-dBF, dTPT3-dIN, dTPT3-dTp, dTPT3-dBTz, dTPT3-dMTp, dTPT3-dAM, dTPT3-dMAN, dTPT3-dDMMAN, dTPT3-dADM, dTPT3-dMMAN, dTPT3-dTOK588, dTPT3-dTOK576, dTPT3-dTOK587, dTPT3-dTOK586, dTPT3-dTOK580, dTPT3-dPhMO, dTPT3-dPyMO1, dTPT3-PyMO2, dTPT3-dPMO1, dTPT3-dPMO2, dTPT3-dPMO3, dTPT3-dFuMO1, dTPT3-dFuMO2, dTPT3-TpMO1, dTPT3-dTpMO2, dTPT3-dFIMO, dTPT3-dIMO, dTPT3-dMIMO, dTPT3-dMEMO, dTPT3-dFEMO, dTPT3-dPrMO, dTPT3-dMMO2, dTPT3-d2OMe, dTPT3-dDMO, dTPT3-dTMO, dTPT3-dNMO, dTPT3-dNOPy, dTPT3-d5FM, dTPT3-dNAM, dTPT3-dAMO1, dTPT3-dAPy, dTPT3-dAMO2, dTPT3-dMAPy, dTPT3-dAMO3, dTPT3-dDMAPy, dTPT3-dFDMO, dTPT3-dVMO, dTPT3-dQMO, dTPT3-dZMO, dTPT3-dCIMO, dTPT3-dTfMO, and dTPT3-CNMO, wherein the dTPT3 complementary base is or is not linker-derivatized (e.g. dMMO2pCO). dTPT3 is illustrated in FIG. 9 as a β6 analog. An example of a linker-derivatized dTPT3 is illustrated in FIG. 2, wherein in some instances, R is a reactive linker comprising a reactive center adapted to bond to a cargo reagent or R is a coupled linker to which a cargo is bonded. Nucleobase analogs which are complementary to dTPT3, include, without limitation, α analogs or linker-derivatized a analogs illustrated in FIGS. 8, 10, 11 and 15. In some embodiments, dTPT3 or a linker-derivatized dTPT3 is base paired with dTPT3 or a linker-derivatized dTPT3, to form a homo-nucleobase pair. In some embodiments, dTPT3 or a linker-derivatized dTPT3 is base paired with a β nucleobase, including but not limited to, any nucleobase illustrated in FIGS. 9, 12, and 13, or a derivatized nucleobase thereof. In some embodiments, a linker moiety is protected with a protecting group, e.g., dTPT3PA. In some embodiments, a linker moiety is not protected with a protecting group, e.g. dTPT3A, wherein in some instances, a protecting group was removed.

Provided herein are unnatural base pairs comprising dMMS, wherein dMMS in some instances, is linker-derivatized. Unnatural base pairs comprising dMMS or linker-derivatized dMMS (e.g., dMMSPA) include, without limitation, d7AI-dMMS, dM7AI-dMMS, dImPy-dMMS, dP7AI-dMMS, dPPP-dMMS, d8Q-dMMS, dICS-dMMS, dPICS-dMMS, dMICS-dMMS, d4MICS-dMMS, d5MICS-dMMS, dNICS-dMMS, dONICS-dMMS, d7OFP-dMMS, d7OTP-dMMS, d4OTP-dMMS, dPYR-dMMS, d4MP-dMMS, d3MP-dMMS, dPPYR-dMMS, dMOP-dMMS, d4MOP-dMMS, dSICS-dMMS, dSNICS-dMMS, d5SICS-dMMS, d4SICS-dMMS, dTPT1-dMMS, dTPT2-dMMS, dFPT1-dMMS, and dFTPT3-dMMS, wherein the dMMS complementary base is or is not linker-derivatized (e.g. pFTPT3pA). dMMS is illustrated in FIG. 11 as an α14a analog. In some embodiments, a linker-derivatized dMMS comprises a functional group R, wherein R is a reactive linker comprising a reactive center adapted to bond to a cargo reagent or R is a coupled linker to which a cargo is bonded. Nucleobase analogs which are complementary to dMMS, include, without limitation, β analogs or linker-derivatized β analogs illustrated in FIGS. 9, 12, and 13. In some embodiments, dMMS or a linker-derivatized dMMS is base paired with dMMS or a linker-derivatized dMMS, to form a homo-nucleobase pair. In some embodiments, dMMS or a linker-derivatized dMMS is base paired with an a nucleobase, including but not limited to, any nucleobase illustrated in FIGS. 8, 10, 11, and 15, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dDMS, wherein dDMS in some instances, is linker-derivatized. Unnatural base pairs comprising dDMS or linker-derivatized dDMS (e.g., dDMSPA) include, without limitation, d7AI-dDMS, dM7AI-dDMS, dImPy-dDMS, dP7AI-dDMS, dPPP-dDMS, d8Q-dDMS, dICS-dDMS, dPICS-dDMS, dMICS-dDMS, d4MICS-dDMS, d5MICS-dDMS, dNICS-dDMS, dONICS-dDMS, d7OFP-dDMS, d7OTP-dDMS, d4OTP-dDMS, dPYR-dDMS, d4MP-dDMS, d3MP-dDMS, dPPYR-dDMS, dMOP-dDMS, d4MOP-dDMS, dSICS-dDMS, dSNICS-dDMS, d5SICS-dDMS, d4SICS-dDMS, dTPT1-dDMS, dTPT2-dDMS, dFPT1-dDMS, dFTPT3-dDMS, wherein the dDMS complementary base is or is not linker-derivatized (e.g. pFTPT3pA). dDMS is illustrated in FIG. 11 as an α14a analog. In some embodiments, a linker-derivatized dDMS comprises a functional group R, wherein R is a reactive linker comprising a reactive center adapted to bond to a cargo reagent or R is a coupled linker to which a cargo is bonded. Nucleobase analogs which are complementary to dDMS, include, without limitation, β analogs or linker-derivatized β analogs illustrated in FIGS. 9, 12, and 13. In some embodiments, dDMS or a linker-derivatized dDMS is base paired with dDMS or a linker-derivatized dDMS, to form a homo-nucleobase pair. In some embodiments, dMMS or a linker-derivatized dMMS is base paired with an a nucleobase, including but not limited to, any nucleobase illustrated in FIGS. 8, 10, 11, and 15, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dFEMS, wherein dFEMS in some instances, is linker-derivatized. Unnatural base pairs comprising dFEMS or linker-derivatized dFEMS (e.g., dFEMSPA) include, without limitation, d7AI-dFEMS, dM7AI-dFEMS, dImPy-dFEMS, dP7AI-dFEMS, dPPP-dFEMS, d8Q-dFEMS, dICS-dFEMS, dPICS-dFEMS, dMICS-dFEMS, d4MICS-dFEMS, d5MICS-dFEMS, dNICS-dFEMS, dONICS-dFEMS, d7OFP-dFEMS, d7OTP-dFEMS, d4OTP-dFEMS, dPYR-dFEMS, d4MP-dFEMS, d3MP-dFEMS, dPPYR-dFEMS, dMOP-dFEMS, d4MOP-dFEMS, dSICS-dFEMS, dSNICS-dFEMS, d5SICS-dFEMS, d4SICS-dFEMS, dTPT1-dFEMS, dTPT2-dFEMS, dFPT1-dFEMS, dFTPT3-dFEMS, wherein the dFEMS complementary base is or is not linker-derivatized (e.g. pFTPT3pA). dFEMS is illustrated in FIG. 11 as an α14a analog. In some embodiments, a linker-derivatized dFEMS comprises a functional group R, wherein R is a reactive linker comprising a reactive center adapted to bond to a cargo reagent or R is a coupled linker to which a cargo is bonded. Nucleobase analogs which are complementary to dFEMS, include, without limitation, β analogs or linker-derivatized β analogs illustrated in FIGS. 9, 12, and 13. In some embodiments, dFEMS or a linker-derivatized dFEMS is base paired with dFEMS or a linker-derivatized dFEMS, to form a homo-nucleobase pair. In some embodiments, dFEMS or a linker-derivatized dFEMS is base paired with an a nucleobase, including but not limited to, any nucleobase illustrated in FIGS. 8, 10, 11, and 15, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dBrMS, wherein dBrMS in some instances, is linker-derivatized. Unnatural base pairs comprising dBrMS or linker-derivatized dBrMS (e.g., dBrMSPA) include, without limitation, d7AI-dBrMS, dM7AI-dBrMS, dImPy-dBrMS, dP7AI-dBrMS, dPPP-dBrMS, d8Q-dBrMS, dICS-dBrMS, dPICS-dBrMS, dMICS-dBrMS, d4MICS-dBrMS, d5MICS-dBrMS, dNICS-dBrMS, dONICS-dBrMS, d7OFP-dBrMS, d7OTP-dBrMS, d4OTP-dBrMS, dPYR-dBrMS, d4MP-dBrMS, d3MP-dBrMS, dPPYR-dBrMS, dMOP-dBrMS, d4MOP-dBrMS, dSICS-dBrMS, dSNICS-dBrMS, d5SICS-dBrMS, d4SICS-dBrMS, dTPT1-dBrMS, dTPT2-dBrMS, dFPT1-dBrMS, dFTPT3-dBrMS, wherein the dBrMS complementary base is or is not linker-derivatized (e.g. pFTPT3pA). dBrMS is illustrated in FIG. 11 as an α14a analog. In some embodiments, a linker-derivatized dBrMS comprises a functional group R, wherein R is a reactive linker comprising a reactive center adapted to bond to a cargo reagent or R is a coupled linker to which a cargo is bonded. Nucleobase analogs which are complementary to dBrMS, include, without limitation, β analogs or linker-derivatized β analogs illustrated in FIGS. 9, 12, and 13. In some embodiments, dBrMS or a linker-derivatized dBrMS is base paired with dBrMS or a linker-derivatized dBrMS, to form a homo-nucleobase pair. In some embodiments, dBrMS or a linker-derivatized dBrMS is base paired with an a nucleobase, including but not limited to, any nucleobase illustrated in FIGS. 8, 10, 11, and 15, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dIMS, wherein dIMS in some instances, is linker-derivatized. Unnatural base pairs comprising dIMS or linker-derivatized dIMS (e.g., dIMSPA) include, without limitation, d7AI-dIMS, dM7AI-dIMS, dImPy-dIMS, dP7AI-dIMS, dPPP-dIMS, d8Q-dIMS, dICS-dIMS, dPICS-dIMS, dMICS-dIMS, d4MICS-dIMS, d5MICS-dIMS, dNICS-dIMS, dONICS-dIMS, d7OFP-dIMS, d7OTP-dIMS, d4OTP-dIMS, dPYR-dIMS, d4MP-dIMS, d3MP-dIMS, dPPYR-dIMS, dMOP-dIMS, d4MOP-dIMS, dSICS-dIMS, dSNICS-dIMS, d5SICS-dIMS, d4SICS-dIMS, dTPT1-dIMS, dTPT2-dIMS, dFPT1-dIMS, dFTPT3-dIMS, wherein the dIMS complementary base is or is not linker-derivatized (e.g. pFTPT3pA). dIMS is illustrated in FIG. 11 as an α14a analog. In some embodiments, a linker-derivatized dIMS comprises a functional group R, wherein R is a reactive linker comprising a reactive center adapted to bond to a cargo reagent or R is a coupled linker to which a cargo is bonded. Nucleobase analogs which are complementary to dIMS, include, without limitation, β analogs or linker-derivatized β analogs illustrated in FIGS. 9, 12, and 13. In some embodiments, dIMS or a linker-derivatized dIMS is base paired with dIMS or a linker-derivatized dIMS, to form a homo-nucleobase pair. In some embodiments, dIMS or a linker-derivatized dIMS is base paired with an α nucleobase, including but not limited to, any nucleobase illustrated in FIGS. 8, 10, 11, and 15, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dICS, wherein dICS in some instances, is linker-derivatized. Unnatural base pairs comprising dICS or linker-derivatized dICS (e.g., dICSPA) include, without limitation, dICS-dFIMO, dICS-dMIMO, dICS-dFEMO, dICS-dPrMO, dICS-dEMO, dICS-dMEMO, dICS-dIMO, dICS-dDMO, dICS-dNMO, dICS-d5FM, dICS-dTMO, dICS-dFDMO, dICS-dVMO, dICS-dZMO, dICS-dCIMO, dICS-dTfMO, dICS-dCNMO, dICS-dNAM, dICS-dQMO, wherein the dICS complementary base is or is not linker-derivatized (e.g. dDMOpCO, dDMOpCC). dICS is illustrated in FIG. 9 as a β2 analog. In some embodiments, a linker-derivatized dICS comprises a functional group R, wherein R is a reactive linker comprising a reactive center adapted to bond to a cargo reagent or R is a coupled linker to which a cargo is bonded. Nucleobase analogs which are complementary to dICS, include, without limitation, α analogs or linker-derivatized α analogs illustrated in FIGS. 8, 10, 11, and 15. In some embodiments, dICS or a linker-derivatized dICS is base paired with dICS or a linker-derivatized dICS, to form a homo-nucleobase pair. In some embodiments, dICS or a linker-derivatized dICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dPICS, wherein dPICS in some instances, is linker-derivatized. Unnatural base pairs comprising dPICS or linker-derivatized dPICS (e.g., dPICSPA) include, without limitation, dPICS-dFIMO, dPICS-dMIMO, dPICS-dFEMO, dPICS-dPrMO, dPICS-dEMO, dPICS-dMEMO, dPICS-dIMO, dPICS-dMMO2, dPICS-dDMO, dPICS-dNMO, dPICS-d5FM, dPICS-d2OMe, dPICS-dTMO, dPICS-dFDMO, dPICS-dVMO, dPICS-dZMO, dPICS-dCIMO, dPICS-dTfMO, dPICS-dCNMO, dPICS-dNAM, dPICSdQMO, wherein the dPICS complementary base is or is not linker-derivatized (e.g. dDMOpCO, dDMOpCC). dPICS is illustrated in FIG. 9 as a β2 analog. In some embodiments, a linker-derivatized dPICS comprises a functional group R, wherein R is a reactive linker comprising a reactive center adapted to bond to a cargo reagent or R is a coupled linker to which a cargo is bonded. Nucleobase analogs which are complementary to dPICS, include, without limitation, α analogs or linker-derivatized α analogs illustrated in FIGS. 8, 10, 11, and 15. In some embodiments, dPICS or a linker-derivatized dPICS is base paired with dPICS or a linker-derivatized dPICS, to form a homo-nucleobase pair. In some embodiments, dPICS or a linker-derivatized dPICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dMICS, wherein dMICS in some instances, is linker-derivatized. Unnatural base pairs comprising dMICS or linker-derivatized dMICS (e.g., dMIC SPA) include, without limitation, dMICS-dFIMO, dMICS-dMIMO, dMICS-dFEMO, dMICS-dPrMO, dMICS-dEMO, dMICS-dMEMO, dMICS-dIMO, dMICS-dMMO2, dMICS-dDMO, dMICS-dNMO, dMICS-d5FM, dMICS-d2OMe, dMICS-dTMO, dMICS-dFDMO, dMICS-dVMO, dMICS-dZMO, dMICS-dCIMO, dMICS-dTfMO, dMICS-dCNMO, dMICS-dNAM, dMICS-dQMO, wherein the dMICS complementary base is or is not linker-derivatized (e.g. dDMOpCO, dDMOpCC). dMICS is illustrated in FIG. 9 as a β2 analog. In some embodiments, a linker-derivatized dMICS comprises a functional group R, wherein R is a reactive linker comprising a reactive center adapted to bond to a cargo reagent or R is a coupled linker to which a cargo is bonded. Nucleobase analogs which are complementary to dMICS, include, without limitation, α analogs or linker-derivatized α analogs illustrated in FIGS. 8, 10, 11, and 15. In some embodiments, dMICS or a linker-derivatized dMICS is base paired with dMICS or a linker-derivatized dMICS, to form a homo-nucleobase pair. In some embodiments, dMICS or a linker-derivatized dMICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising d4MICS, wherein d4MICS in some instances, is linker-derivatized. Unnatural base pairs comprising d4MICS or linker-derivatized d4MICS (e.g., d4MICSPA) include, without limitation, d4MICS-dFIMO, d4MICS-dMIMO, d4MICS-dFEMO, d4MICS-dPrMO, d4MICS-dEMO, d4MICS-dMEMO, d4MICS-dIMO, d4MICS-dMMO2, d4MICS-dDMO, d4MICS-dNMO, d4MICS-d5FM, d4MICS-d2OMe, d4MICS-dTMO, d4MICS-dFDMO, d4MICS-dVMO, d4MICS-dZMO, d4MICS-dCIMO, d4MICS-dTfMO, d4MICS-dCNMO, d4MICS-dNAM, d4MICS-dQMO, wherein the d4MICS complementary base is or is not linker-derivatized (e.g. dDMOpCO, dDMOpCC). d4MICS is illustrated in FIG. 9 as a β2 analog. In some embodiments, a linker-derivatized d4MICS comprises a functional group R, wherein R is a reactive linker comprising a reactive center adapted to bond to a cargo reagent or R is a coupled linker to which a cargo is bonded. Nucleobase analogs which are complementary to d4MICS, include, without limitation, α analogs or linker-derivatized α analogs illustrated in FIGS. 8, 10, 11, and 15. In some embodiments, d4MICS or a linker-derivatized d4MICS is base paired with d4MICS or a linker-derivatized d4MICS, to form a homo-nucleobase pair. In some embodiments, d4MICS or a linker-derivatized d4MICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising d5MICS, wherein d5MICS in some instances, is linker-derivatized. Unnatural base pairs comprising d5MICS or linker-derivatized d5MICS (e.g., d5MICSPA) include, without limitation, d5MICS-dFIMO, d5MICS-dMIMO, d5MICS-dFEMO, d5MICS-dPrMO, d5MICS-dEMO, d5MICS-dMEMO, d5MICS-dIMO, d5MICS-dMMO2, d5MICS-dDMO, d5MICS-dNMO, d5MICS-d5FM, d5MICS-d2OMe, d5MICS-dTMO, d5MICS-dFDMO, d5MICS-dVMO, d5MICS-dZMO, d5MICS-dCIMO, d5MICS-dTfMO, d5MICS-dCNMO, d5MICS-dNAM, d5MICS-dQMO, wherein the d5MICS complementary base is or is not linker-derivatized (e.g. dDMOpCO, dDMOpCC). d5MICS is illustrated in FIG. 9 as a β2 analog. In some embodiments, a linker-derivatized d5MICS comprises a functional group R, wherein R is a reactive linker comprising a reactive center adapted to bond to a cargo reagent or R is a coupled linker to which a cargo is bonded. Nucleobase analogs which are complementary to d5MICS, include, without limitation, α analogs or linker-derivatized α analogs illustrated in FIGS. 8, 10, 11, and 15. In some embodiments, d5MICS or a linker-derivatized d5MICS is base paired with d5MICS or a linker-derivatized d5MICS, to form a homo-nucleobase pair. In some embodiments, d5MICS or a linker-derivatized d5MICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dNICS, wherein dNICS in some instances, is linker-derivatized. Unnatural base pairs comprising dNICS or linker-derivatized dNICS (e.g., dNIC SPA) include, without limitation, dNICS-dFIMO, dNICS-dMIMO, dNICS-dFEMO, dNICS-dPrMO, dNICS-dEMO, dNICS-dMEMO, dNICS-dIMO, dNICS-dDMO, dNICS-dNMO, dNICS-d5FM, dNICS-dTMO, dNICS-dFDMO, dNICS-dVMO, dNICS-dZMO, dNICS-dCIMO, dNICS-MMO2, dNICS-2OMe, dNICS-dTfMO, dNICS-dCNMO, dNICS-dNAM, dNICS-dQMO, wherein the dNICS complementary base is or is not linker-derivatized (e.g. dDMOpCO, dDMOpCC). dNICS is illustrated in FIG. 9 as a β3 analog. In some embodiments, a linker-derivatized dNICS comprises a functional group R, wherein R is a reactive linker comprising a reactive center adapted to bond to a cargo reagent or R is a coupled linker to which a cargo is bonded. Nucleobase analogs which are complementary to dNICS, include, without limitation, α analogs or linker-derivatized α analogs illustrated in FIGS. 8, 10, 11, and 15. In some embodiments, dNICS or a linker-derivatized dNICS is base paired with dNICS or a linker-derivatized dNICS, to form a homo-nucleobase pair.

In some embodiments, dNICS or a linker-derivatized dNICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dONICS, wherein dONICS in some instances, is linker-derivatized. Unnatural base pairs comprising dONICS or linker-derivatized dONICS (e.g., dONICSPA) include, without limitation, dONICS-dFIMO, dONICS-dMIMO, dONICS-dFEMO, dONIC S-dPrMO, dONIC S-dEMO, dONIC S-dMEMO, dONICS-dIMO, dONICS-dDMO, dONIC S-dNMO, dONIC S-d5FM, dONICS-dTMO, dONIC S-dFDMO, dONICS-dVMO, dONICS-dZMO, dONIC S-dCIMO, dONIC S-MMO2, dONICS-2OMe, dONICS-dTfMO, dONICS-dCNMO, dONICS-dNAM, dONICS-dQMO, wherein the dONICS complementary base is or is not linker-derivatized (e.g. dDMOpCO, dDMOpCC). dONICS is illustrated in FIG. 9 as a β3 analog. In some embodiments, a linker-derivatized dONICS comprises a functional group R, wherein R is a reactive linker comprising a reactive center adapted to bond to a cargo reagent or R is a coupled linker to which a cargo is bonded. Nucleobase analogs which are complementary to dONICS, include, without limitation, α analogs or linker-derivatized α analogs illustrated in FIGS. 8, 10, 11, and 15. In some embodiments, dONICS or a linker-derivatized dONICS is base paired with dONICS or a linker-derivatized dONICS, to form a homo-nucleobase pair. In some embodiments, dONICS or a linker-derivatized dONICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dSICS, wherein dSICS in some instances, is linker-derivatized. Unnatural base pairs comprising dSICS or linker-derivatized dSICS (e.g., dSICSPA) include, without limitation, dSICS-dFIMO, dSICS-dMIMO, dSICS-dFEMO, dSICS-dPrMO, dSICS-dEMO, dSICS-dMEMO, dSICS-dIMO, dSICS-dDMO, dSICS-dNMO, dSICS-d5FM, dSICS-dTMO, dSICS-dFDMO, dSICS-dVMO, dSICS-dZMO, dSICS-dCIMO, dSICS-dTfMO, dSICS-dCNMO, dSICS-dNAM, dSICS-dQMO, wherein the dSICS complementary base is or is not linker-derivatized (e.g. dDMOpCO, dDMOpCC). dSICS is illustrated in FIG. 9 as a β5 analog. In some embodiments, a linker-derivatized dSICS comprises a functional group R, wherein R is a reactive linker comprising a reactive center adapted to bond to a cargo reagent or R is a coupled linker to which a cargo is bonded. Nucleobase analogs which are complementary to dSICS, include, without limitation, α analogs or linker-derivatized α analogs illustrated in FIGS. 8, 10, 11, and 15. In some embodiments, dSICS or a linker-derivatized dSICS is base paired with dSICS or a linker-derivatized dSICS, to form a homo-nucleobase pair. In some embodiments, dSICS or a linker-derivatized dSICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising dSNICS, wherein dSNICS in some instances, is linker-derivatized. Unnatural base pairs comprising dSNICS or linker-derivatized dSNICS (e.g., dSNICSPA) include, without limitation, dSNICS-dFIMO, dSNICS-dMIMO, dSNICS-dFEMO, dSNICS-dPrMO, dSNICS-dEMO, dSNICS-dMEMO, dSNICS-dIMO, dSNICS-dDMO, dSNICS-dNMO, dSNICS-d5FM, dSNICS-dTMO, dSNICS-dFDMO, dSNICS-dVMO, dSNICS-dZMO, dSNICS-dCIMO, dSNICS-dTfMO, dSNICS-dCNMO, dSNICS-dNAM, dSNICS-dQMO, wherein the dSNICS complementary base is or is not linker-derivatized (e.g. dDMOpCO, dDMOpCC). dSNICS is illustrated in FIG. 9 as a β5 analog. In some embodiments, a linker-derivatized dSNICS comprises a functional group R, wherein R is a reactive linker comprising a reactive center adapted to bond to a cargo reagent or R is a coupled linker to which a cargo is bonded. Nucleobase analogs which are complementary to dSNICS, include, without limitation, α analogs or linker-derivatized α analogs illustrated in FIGS. 8, 10, 11, and 15. In some embodiments, dSNICS or a linker-derivatized dSNICS is base paired with dSNICS or a linker-derivatized dSNICS, to form a homo-nucleobase pair. In some embodiments, dSNICS or a linker-derivatized dSNICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising d4SICS, wherein d4SICS in some instances, is linker-derivatized. Unnatural base pairs comprising d4SICS or linker-derivatized d4SICS (e.g., d4SICSPA) include, without limitation, d4SICS-dFIMO, d4SICS-dMIMO, d4SICS-dFEMO, d4SICS-dPrMO, d4SICS-dEMO, d4SICS-dMEMO, d4SICS-dIMO, d4SICS-dDMO, d4SICS-dNMO, d4SICS-d5FM, d4SICS-dTMO, d4SICS-dFDMO, d4SICS-dVMO, d4SICS-dZMO, d4SICS-dCIMO, d4SICS-dTfMO, d4SICS-dCNMO, d4SICS-dNAM, d4SICS-dQMO, wherein the d4SICS complementary base is or is not linker-derivatized (e.g. dDMOpCO, dDMOpCC). d4SICS is illustrated in FIG. 9 as a β5 analog. In some embodiments, a linker-derivatized d4SICS comprises a functional group R, wherein R is a reactive linker comprising a reactive center adapted to bond to a cargo reagent or R is a coupled linker to which a cargo is bonded. Nucleobase analogs which are complementary to d4SICS, include, without limitation, a analogs or linker-derivatized α analogs illustrated in FIGS. 8, 10, 11, and 15. In some embodiments, d4SICS or a linker-derivatized d4SICS is base paired with d4SICS or a linker-derivatized d4SICS, to form a homo-nucleobase pair. In some embodiments, d4SICS or a linker-derivatized d4SICS is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising d7OFP, wherein d7OFP in some instances, is linker-derivatized. Unnatural base pairs comprising d7OFP or linker-derivatized d7OFP (e.g., d7OFPPA) include, without limitation, d7OFP-dFIMO, d7OFP-dMIMO, d7OFP-dFEMO, d7OFP-dPrMO, d7OFP-dEMO, d7OFP-dMEMO, d7OFP-dIMO, d7OFP-dMMO2, d7OFP-dDMO, d7OFP-dNMO, d7OFP-d5FM, d7OFP-d2OMe, d7OFP-dTMO, d7OFP-dFDMO, d7OFP-dVMO, d7OFP-dZMO, d7OFP-dCIMO, d7OFP-dTfMO, d7OFP-dCNMO, d7OFP-dNAM, d7OFP-dQMO, wherein the d7OFP complementary base is or is not linker-derivatized (e.g. dDMOpCO, dDMOpCC). d7OFP is illustrated in FIG. 9 as a β5 analog. In some embodiments, a linker-derivatized d7OFP comprises a functional group R, wherein R is a reactive linker comprising a reactive center adapted to bond to a cargo reagent or R is a coupled linker to which a cargo is bonded. Nucleobase analogs which are complementary to d7OFP, include, without limitation, α analogs or linker-derivatized α analogs illustrated in FIGS. 8, 10, 11, and 15. In some embodiments, d7OFP or a linker-derivatized d7OFP is base paired with d7OFP or a linker-derivatized d7OFP, to form a homo-nucleobase pair. In some embodiments, d7OFP or a linker-derivatized d7OFP is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Provided herein are unnatural base pairs comprising d7OTP, wherein d7OTP in some instances, is linker-derivatized. Unnatural base pairs comprising d7OTP or linker-derivatized d7OTP (e.g., d7OTPPA) include, without limitation, d7OTP-dFIMO, d7OTP-dMIMO, d7OTP-dFEMO, d7OTP-dPrMO, d7OTP-dEMO, d7OTP-dMEMO, d7OTP-dIMO, d7OTP-dMMO2, d7OTP-dDMO, d7OTP-dNMO, d7OTP-d5FM, d7OTP-d2OMe, d7OTP-dTMO, d7OTP-dFDMO, d7OTP-dVMO, d7OTP-dZMO, d7OTP-dCIMO, d7OTP-dTfMO, d7OTP-dCNMO, d7OTP-dNAM, d7OTP-dQMO, wherein the d7OTP complementary base is or is not linker-derivatized (e.g. dDMOpCO, dDMOpCC). d7OTP is illustrated in FIG. 9 as a β5analog. In some embodiments, a linker-derivatized d7OTP comprises a functional group R, wherein R is a reactive linker comprising a reactive center adapted to bond to a cargo reagent or R is a coupled linker to which a cargo is bonded. Nucleobase analogs which are complementary to d7OTP, include, without limitation, α analogs or linker-derivatized α analogs illustrated in FIGS. 8, 10, 11, and 15. In some embodiments, d7OTP or a linker-derivatized d7OTP is base paired with d7OTP or a linker-derivatized d7OTP, to form a homo-nucleobase pair. In some embodiments, d7OTP or a linker-derivatized d7OTP is base paired with a β nucleobase, including but not limited to, any nucleobase illustrated in FIGS. 9, 12, and 13, or a derivatized nucleobase thereof. In some embodiments, a linker moiety is protected with a protecting group. In some embodiments, a linker moiety is not protected with a protecting group, wherein in some instances, a protecting group was removed.

Further provided herein, in various embodiments, is a nucleobase pair comprising a first nucleobase TPT3 and a second nucleobase MIMS. Further provided herein, in various embodiments, is a nucleobase pair comprising a first nucleobase TPT3 and a second nucleobase DMS. Further provided herein, in various embodiments, is a nucleobase pair comprising a first nucleobase TPT3 and a second nucleobase FEMS. Further provided herein, in various embodiments, is a nucleobase pair comprising a first nucleobase TPT3 and a second nucleobase BrMS. Further provided herein, in various embodiments, is a nucleobase pair comprising a first nucleobase TPT3 and a second nucleobase IMS.

Further provided herein, in various embodiments, is a nucleobase pair comprising a first nucleobase FTPT3 and a second nucleobase MMS. Further provided herein, in various embodiments, is a nucleobase pair comprising a first nucleobase FTPT3 and a second nucleobase DMS. Further provided herein, in various embodiments, is a nucleobase pair comprising a first nucleobase FTPT3 and a second nucleobase FEMS. Further provided herein, in various embodiments, is a nucleobase pair comprising a first nucleobase FTPT3 and a second nucleobase BrMS. Further provided herein, in various embodiments, is a nucleobase pair comprising a first nucleobase FTPT3 and a second nucleobase IMS.

Further provided herein, in various embodiments, is a nucleobase pair comprising a first nucleobase 5SICS and a second nucleobase MMS. Further provided herein, in various embodiments, is a nucleobase pair comprising a first nucleobase 5SICS and a second nucleobase DMS. Further provided herein, in various embodiments, is a nucleobase pair comprising a first nucleobase 5SICS and a second nucleobase FEMS. Further provided herein, in various embodiments, is a nucleobase pair comprising a first nucleobase 5SICS and a second nucleobase BrMS. Further provided herein, in various embodiments, is a nucleobase pair comprising a first nucleobase 5SICS and a second nucleobase IMS.

Further provided herein, in various embodiments, is a nucleobase pair comprising a first nucleobase SICS and a second nucleobase MIMS. Further provided herein, in various embodiments, is a nucleobase pair comprising a first nucleobase SICS and a second nucleobase DMS. Further provided herein, in various embodiments, is a nucleobase pair comprising a first nucleobase SICS and a second nucleobase FEMS. Further provided herein, in various embodiments, is a nucleobase pair comprising a first nucleobase SICS and a second nucleobase BrMS. Further provided herein, in various embodiments, is a nucleobase pair comprising a first nucleobase SICS and a second nucleobase IMS.

Further provided herein, in various embodiments, is a double stranded oligonucleotide duplex wherein a first oligonucleotide strand includes an unnatural nucleobase (e.g., nucleobase analog) disclosed herein, and a second complementary oligonucleotide strand comprising a complementary base-pairing nucleobase in a complementary base-pairing site thereof. For instance, for dTPT3, a second complementary oligonucleotide strand comprises dNaM, dDMO, or dMMO2, or a linker-derivatized analog thereof, in a complementary base-pairing site. In this way, the pairing interaction between the first oligonucleotide strand and the second oligonucleotide strand includes a specific nucleobase-pairing interaction between an unnatural nucleobase moiety provided herein and a complementary nucleobase, which can be a natural or an unnatural nucleobase.

Provided herein, in some embodiments, is a double stranded oligonucleotide duplex wherein a first oligonucleotide strand comprises a compound having the formula β8a or β8b, and a second complementary oligonucleotide strand comprises a complementary base-pairing nucleobase in a complementary base-pairing site thereof. In some embodiments, the complementary base-pairing nucleobase is a compound having the formula α14a, α14b, α14c, α14d, α14e, or α14f. In some embodiments, the complementary base-pairing nucleobase includes, without limitation, cytosine, guanine, adenine, thymine, uracil, 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azocytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetyl cytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosyl queosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

Provided herein, in some embodiments, is a double stranded oligonucleotide duplex wherein a first oligonucleotide strand comprises a compound having the formula α14a, α14b, α14c, α14d, α14e, or α14f, and a second complementary oligonucleotide strand comprises a complementary base-pairing nucleobase in a complementary base-pairing site thereof. In some embodiments, the complementary base-pairing nucleobase is a compound having the formula β8a or β8b. In some embodiments, the complementary base-pairing nucleobase includes, without limitation, cytosine, guanine, adenine, thymine, uracil, 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

In some embodiments, at least one R2 of a nucleobase in a double stranded oligonucleotide duplex is a coupled linker bonded with a cargo. In some embodiments, the cargo is a reporter group, protein, or compound comprising catalytic functionality.

In some embodiments, a first oligonucleotide strand comprising a nucleobase analog disclosed herein is prepared by synthesis with a nucleobase comprising a reactive linker, followed by coupling of the cargo reagent with the first oligonucleotide strand, or wherein the first oligonucleotide strand is prepared by synthesis with a nucleobase comprising a coupled linker bonded to a cargo.

In some embodiments, a double stranded oligonucleotide duplex has a first strand comprising dTPT3 or a derivative thereof, and a second strand comprising dNaM, dDMO, or dMMO2 or a derivative thereof in a complementary base-pairing site thereof.

Further provided herein, in various embodiments, is a method of carrying out a site-specific functionalization of a double stranded oligonucleotide duplex, comprising: incorporating an unnatural nucleobase comprising a reactive linker comprising a reactive center, the nucleobase having any of the following formulas α14a, α14b, α14c, α14d, α14e, α14f, β8a, β8b, β9a, β9b, α15a, α15b, α16a, or α16b, into a first oligonucleotide strand; then, synthesizing a second strand complementary to the first strand, the second strand comprising a nucleobase complementary to the unnatural nucleobase at a site-specific complementary position therein, under conditions such that the first strand and the second strand form a double stranded oligonucleotide duplex; then, contacting the double stranded oligonucleotide duplex incorporating the unnatural nucleobase comprising the reactive linker moiety with a cargo reagent comprising a cargo and a group of complementary reactivity, under conditions suitable for reaction of the reactive linker and the group of complementary reactivity to occur to yield a coupled linker; to provide the functionalized double stranded oligonucleotide duplex with the cargo bonded thereto via a coupled linker.

Further provided herein, in various embodiments, is a method of carrying out a site-specific functionalization of a double stranded oligonucleotide duplex, comprising: incorporating an unnatural nucleobase comprising a reactive linker comprising a reactive center, the nucleobase being selected from the group consisting of d5SICSCO, d5SICSCC, dDMOCO, dDMOCC, dMMO2pCO, dMMO2pCC, dTPT3, dTPT3A, dTPT3PA, dTPT3CO, and dTPT3CC, into a first oligonucleotide strand; then, synthesizing a second strand complementary to the first strand, the second strand comprising a nucleobase complementary to the unnatural nucleobase at a site-specific complementary position therein, under conditions such that the first strand and the second strand form a double stranded oligonucleotide duplex; then, contacting the double stranded oligonucleotide duplex incorporating the unnatural nucleobase comprising the reactive linker moiety with a cargo reagent comprising a cargo and a group of complementary reactivity, under conditions suitable for reaction of the reactive linker and the group of complementary reactivity to occur to yield a coupled linker; to provide the functionalized double stranded oligonucleotide duplex with the cargo bonded thereto via a coupled linker.

In an embodiment, the linker is bonded with a cargo after the corresponding 5' triphosphate is incorporated into a DNA or RNA oligonucleotide using a DNA or RNA polymerase (after deprotection, if required). In another embodiment, a second oligonucleotide is synthesized that is complementary to the first strand, the second strand containing an unnatural nucleotide at a position complementary to the unnatural nucleotide of the first strand; then, reacting the resulting double stranded oligonucleotide with a cargo-bearing reagent that reacts selectively with the reactive center of the reactive linker provides a functionalized double stranded oligonucleotide (e.g. DNA/DNA, DNA/RNA, or RNA/RNA) bearing a cargo.

Further provided herein, in various embodiments, are structures comprising the formula: N1-Zx-N2, wherein N1 is a nucleotide or analog thereof, or terminal phosphate group; wherein N2 is a nucleotide or analog thereof, or terminal hydroxyl group; wherein Z is a compound of having any of the formulas α14a, α14b, α14c, α14d, α14e, α14f, β8a, β8b, β9a, β9b, α15a, α15b, α16a, or α16b; and wherein x is an integer from 1 to 20. In some embodiments, the structure is an oligonucleotide. In some embodiments, the oligonucleotide is a ribonucleic acid or a deoxyribonucleic acid. In some embodiments, the oligonucleotide is an aptamer or nucleic acid based sensor. In some embodiments, the oligonucleotide is a molecular beacon. In some embodiments, the oligonucleotide is an RNA analog or DNA analog.

Further provided herein, in various embodiments, is a method for identifying a nucleic acid aptamer comprising at least one compound provided herein (e.g. α14a, α14b, α14c, α14d, α14e, α14f, β8a, β8b, β9a, β9b, α15a, α15b, α16a, α16b), as having an enhanced desired property with respect to a target molecule, the method comprising: a) preparing a candidate mixture of single-stranded nucleic acid aptamers, wherein each nucleic acid aptamer of the candidate mixture of aptamers comprises at least one compound provided herein (e.g. α14a, α14b, α14c, α14d, α14e, α14f, β8a, β8b, β9a, β9b, α15a, α15b, α16a, α16b); then, b) contacting the candidate mixture with the target molecule under conditions suitable for binding to the target molecule to occur; then, c) partitioning the one or more nucleic acid aptamer having the desired property with respect to the target molecule from among the aptamers of the candidate mixture; and then, d) amplifying the one or more nucleic acid aptamer with the desired property, in vitro, to yield the one or more nucleic acid aptamers, having an enhanced desired property with respect to the target molecule. In some embodiments, the method further comprises step e) repeating steps c) and d). In some embodiments, the single-stranded nucleic acids aptamers are selected from the group consisting of single-stranded DNA and single-stranded RNA. In some embodiments, the desired property is a binding affinity for a target. In some embodiments, the desired property is a target binding induced activity. In some embodiments, the desired property is a catalytic activity. In some embodiments, the desired property is an inhibition activity, an activation activity, or a modification of an inhibition activity or an activation activity. In some embodiments, the desired property is a structure switching activity or a modification of a structure switching activity. In some embodiments, the desired property is a cooperative activity. In some embodiments, the desired activity is an enhanced cellular update efficacy.

Further provided herein, in certain embodiments, is an aptamer comprising a compound having any of the following formulas: α14a, α14b, α14c, α14d, α14e, α14f, β8a, β8b, β9a, β9b, α15a, α15b, α16a, α16b.

DETAILED DESCRIPTION

Figure 1:
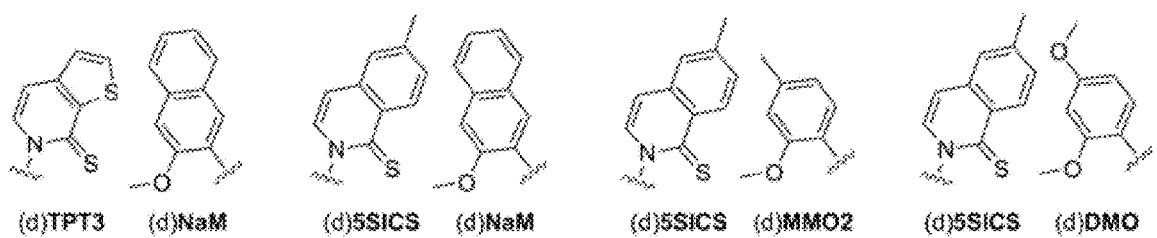
FIG. 1 illustrates the pairing of dTPT3-dNaM, d5SICS-dNaM, d5SICS-dMMO2, d5SICS-dDMO in DNA or RNA.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. In some embodiments, a nucleotide analog is an unnatural nucleotide. In some embodiments, a nucleoside analog is an unnatural nucleoside. A related chemical structure that is readily derived synthetically from a parent chemical structure is referred to as a "derivative."

Accordingly, a "DNA analog" or an "RNA analog", as the terms are used herein, refer to DNA or RNA-like polymers such as peptide nucleic acids (PNA), locked nucleic acids (LNA), phosphorothioates, and the like, which are well-known in the art. DNA and RNA analogs, as well as DNA and RNA, can be synthesized in automated synthesizers, e.g., using phosphoroamidite chemistry or other chemical approaches adapted for synthesizer use.

DNA includes, but is not limited to, cDNA and genomic DNA. DNA may be attached, by covalent or non-covalent means, to another biomolecule, including, but not limited to, RNA and peptide. RNA includes coding RNA, e.g. messenger RNA (mRNA). In some embodiments, RNA is rRNA, RNAi, snoRNA, microRNA, siRNA, snRNA, exRNA, piRNA, long ncRNA, or any combination or hybrid thereof. In some instances, RNA is a component of a ribozyme. DNA and RNA can be in any form, including, but not limited to, linear, circular, supercoiled, single-stranded, and double-stranded.

The term "amino protecting group" or "amino-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, NY, (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. Protecting groups also include methyl carbamate, 9-fluorenylmethyl carbamate, 2,2,2-trichloroethyl carbamate, t-butyl carbamate, 2-(trimethylsilyl)ethyl carbamate, allyl carbamate, benzyl carbamate, m-nitrophenyl carbamate, trifluoroacetamide, benzylamine, allylamine, and tritylamine. Protecting groups also include, formamides, acetamides, trifluoroacetamides, p-toluenesulfonyl, trifluoromethanesulfonyl, trimethylsilylethanesulfonamide, and tert-butylfulfonyl. It is well within the skill of the ordinary artisan to select and use the appropriate amino protecting group for the synthetic task at hand.

DNA and RNA analogs include PNA (peptide nucleic acid) and LNA (locked nucleic acid) analogs.

A peptide nucleic acid (PNA) is a synthetic DNA/RNA analog wherein a peptide-like backbone replaces the sugar-phosphate backbone of DNA or RNA. PNA oligomers show higher binding strength and greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. See also Nielsen P E, Egholm M, Berg R H, Buchardt O (December 1991). "Sequence-selective recognition of DNA by strand displacement with a thymine-substituted polyamide", *Science* 254 (5037): 1497-500. doi: 10.1126/science.1962210. PMID 1962210; and, Egholm M, Buchardt O, Christensen L, Behrens C, Freier S M, Driver D A, Berg R H, Kim S K, Norden B, and Nielsen P E (1993), "PNA Hybridizes to Complementary Oligonucleotides Obeying the Watson-Crick Hydrogen Bonding Rules". *Nature* 365 (6446): 566-8. doi:10.1038/365566a0. PMID 7692304

A locked nucleic acid (LNA) is a modified RNA nucleotide, wherein the ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers can be synthesized chemically and are commercially available. The locked ribose conformation enhances base stacking and backbone pre-organization. See, for example, Kaur, H; Arora, A; Wengel, J; Maiti, S (2006), "Thermodynamic, Counterion, and Hydration Effects for the Incorporation of Locked Nucleic Acid Nucleotides into DNA Duplexes", *Biochemistry* 45 (23): 7347-55. doi: 10.1021/bi060307w. PMID 16752924; Owczarzy R.; You Y., Groth C. L., Tataurov A. V. (2011), "Stability and mismatch discrimination of locked nucleic acid-DNA duplexes.", *Biochem.* 50 (43): 9352-9367. doi:10.1021/bi200904e. PMC 3201676. PMID 21928795; Alexei A. Koshkin; Sanjay K. Singh, Poul Nielsen, Vivek K. Rajwanshi, Ravindra Kumar, Michael Meldgaard, Carl Erik Olsen, Jesper Wengel (1998), "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", *Tetrahedron* 54 (14): 3607-30. doi:10.1016/S0040-4020(98)00094-5; and, Satoshi Obika; Daishu Nanbu, Yoshiyuki Hari, Ken-ichiro Morio, Yasuko In, Toshimasa Ishida, Takeshi Imanishi (1997), "Synthesis of 2'-O,4'-C-methyleneuridine and -cytidine. Novel bicyclic nucleosides having a fixed C3'-endo sugar puckering", *Tetrahedron Lett.* 38 (50): 8735-8. doi:10.1016/S0040-4039(97)10322-7.

A molecular beacon or molecular beacon probe is an oligonucleotide hybridization probe that can detect the presence of a specific nucleic acid sequence in a homogenous solution. Molecular beacons are hairpin shaped molecules with an internally quenched fluorophore whose fluorescence is restored when they bind to a target nucleic acid sequence. See, for example, Tyagi S, Kramer F R (1996), "Molecular beacons: probes that fluoresce upon hybridization", *Nat Biotechnol.* 14 (3): 303-8. PMID 9630890; Täpp I, Malmberg L, Rennel E, Wik M, Syvänen A C (2000 April), "Homogeneous scoring of single-nucleotide polymorphisms: comparison of the 5'-nuclease TaqMan assay and Molecular Beacon probes", *Biotechniques* 28 (4): 732-8. PMID 10769752; and, Akimitsu Okamoto (2011), "ECHO probes: a concept of fluorescence control for practical nucleic acid sensing", *Chem. Soc. Rev.* 40: 5815-5828.

In some embodiments, a nucleobase is generally the heterocyclic base portion of a nucleoside. Nucleobases may be naturally occurring, may be modified, may bear no similarity to natural bases, and may be synthesized, e.g., by organic synthesis. In certain embodiments, a nucleobase comprises any atom or group of atoms capable of interacting with a base of another nucleic acid with or without the use of hydrogen bonds. In certain embodiments, an unnatural nucleobase is not derived from a natural nucleobase. It should be noted that unnatural nucleobases do not necessarily possess basic properties, however, are referred to as nucleobases for simplicity. In some embodiments, when referring to a nucleobase, a "(d)" indicates that the nucleobase can be attached to a deoxyribose or a ribose.

In some embodiments, a nucleoside is a compound comprising a nucleobase moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides include nucleosides comprising any variety of substituents. A nucleoside can be a glycoside compound formed through glycosidic linking between a nucleic acid base and a reducing group of a sugar.

In some embodiments, a nucleotide is a compound in which the sugar moiety of a nucleoside forms an ester with phosphoric acid, more preferably a mono-, di- or tri-phosphate ester. The sugar moiety of such a nucleoside or nucleotide may be ribofuranosyl, 2'-deoxyribofuranosyl, or 2'-substituted ribofuranosyl having a substituent at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a member constituting RNA. A deoxyribonucleotide whose sugar moiety is deoxyribofuranosyl can be used as a member constituting DNA. A nucleotide can be a nucleoside further comprising a phosphate linking group. Nucleotides may include nucleosides containing a phosphate moiety.

A class of unnatural base pairs, exemplified by d5SICS-dNaM and d5SICS-dMMO2 (FIG. 1), has been developed and shown by us to be replicated (including via PCR) and transcribed by a wide range of natural polymerases with efficiencies and fidelities approaching those of a natural base pair (See Malyshev, D. A.; Seo, Y. J.; Ordoukhanian, P.; Romesberg, F. E., PCR with an Expanded Genetic Alphabet. J. Am. Chem. Soc. 2009. 131 (41), 14620-14621; Seo, Y. J.; Matsuda, S.; Romesberg, F. E., Transcription of an Expanded Genetic Alphabet. J. Am. Chem. Soc. 2009, 131 (14), 5046-5047; Lavergne T.; Degardin M.; Malyshev D. A.; Quach H. T.; Dhami K.; Ordoukhanian P.; Romesberg, F. E., Expanding the scope of replicable unnatural DNA: Stepwise optimization of a predominantly hydrophobic base pair. J. Am. Chem. Soc. 2013, 135, 5408-5419; Seo, Y. J., Malyshev D. A., Lavergne T., Ordoukhanian P., and Romesberg, F. E., J. Am. Chem. Soc. 2011, 133, 19878). These unnatural base pairs are formed between nucleotide analogs bearing unnatural, predominantly hydrophobic nucleobases. The base pairs are shown in FIG. 1, with each unnatural nucleotide being incorporated into oligonucleotides at complementary (i.e. paring) positions; the nucleobases are understood to be bonded at the position indicated by the wavy line to the 1'-position of a ribosyl or 2'-deoxyribosyl moiety, which is itself incorporated into RNA or DNA by phosphate or phosphorothioate groups bonding the 3' and 5' hydroxyl groups of the ribosyl or deoxyribosyl groups, respectively, as it is in the case with fully natural nucleic acids. The base pairing thus takes place as part of a complementary base paired structure as is well-known in the formation of oligonucleotide duplex structures. Provided herein, in various embodiments, is an unnatural nucleobase dTPT3 and its linker-derivatized variants, which are thought to pair with unnatural nucleobases dNaM, dMMO2, and dDMO (or their linker-derivatized variants) in a similar fashion.

Figure 2:
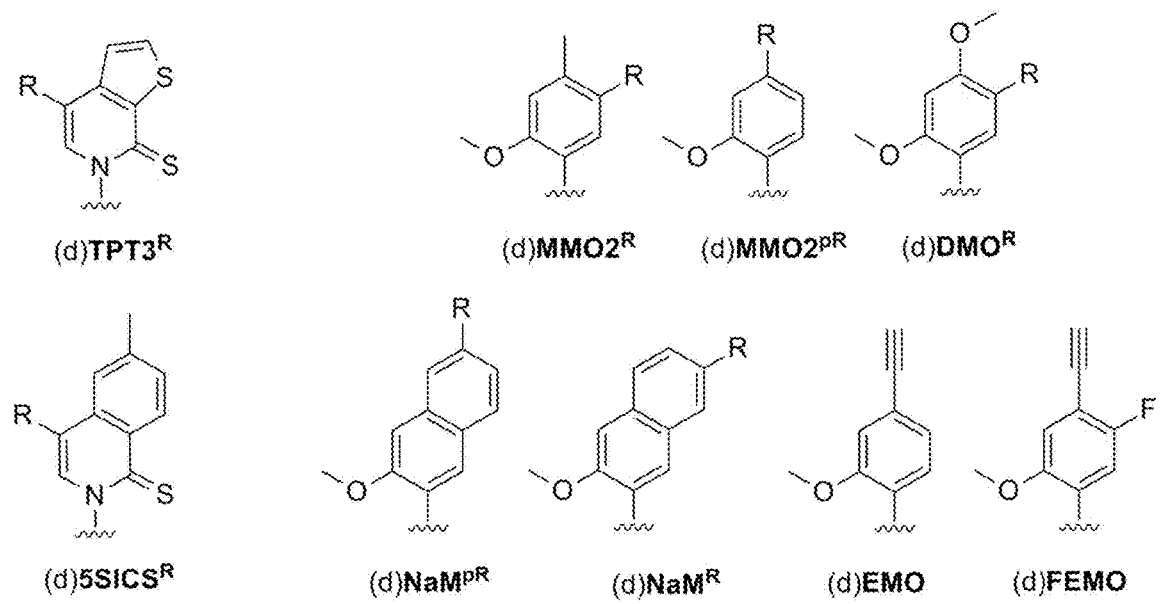
FIG. 2 illustrates the linker-derivatized nucleotides dTPT3R, d5SICSR, dMMO2R, dMMO2pR, dDMOR, dNaMpR, dNaMpR, dFEMO and dEMO, where R=3-aminopropyn-1-yl (denoted as A, e.g. dTPT3A); R=dichloroacetyl-3-aminopropyn-1-yl (denoted as PA); R=4-oxahepta-1,6-diyn-1-yl (denoted as CO); R=hepta-1,6-diyn-1-yl (denoted as CC).

We have demonstrated that the unnatural nucleotides dTPT3 and dTPT3$^{PA}$ are efficiently incorporated into DNA by DNA polymerases opposite dNaM (FIG. 2). Both dTPT3 and dTPT3$^{PA}$ (PA=dichloroacetyl-3-aminopropyn-1-yl) as well as other linker-derivatized variants of dTPT3 (FIG. 3) including, when R=3-aminopropyn-1-yl (dTPT3$^A$), R=4-oxahepat-1,6-diyn-1-yl (dTPT$^{CO}$), or R=hepta-1,6-diyn-1-yl (dTPT$^{CC}$)) are also expected to pair with dNaM, dDMO or dMMO2, or linker-derivatized analogs thereof. Incorporation rates of dTPT3 and linker-derivatized variants thereof, opposite dNAM approach those of a natural base pair. Additional unnatural base pairs identified with efficient incorporation rates include dTPT3-dFEMO, dTPT3-dFIMO, dTPT3-dIMO, dFTPT3-dNaM, dFTPT3-dFEMO, dFTPT3-dFIMO, and dFTPT3-dIMO.

Figure 9:
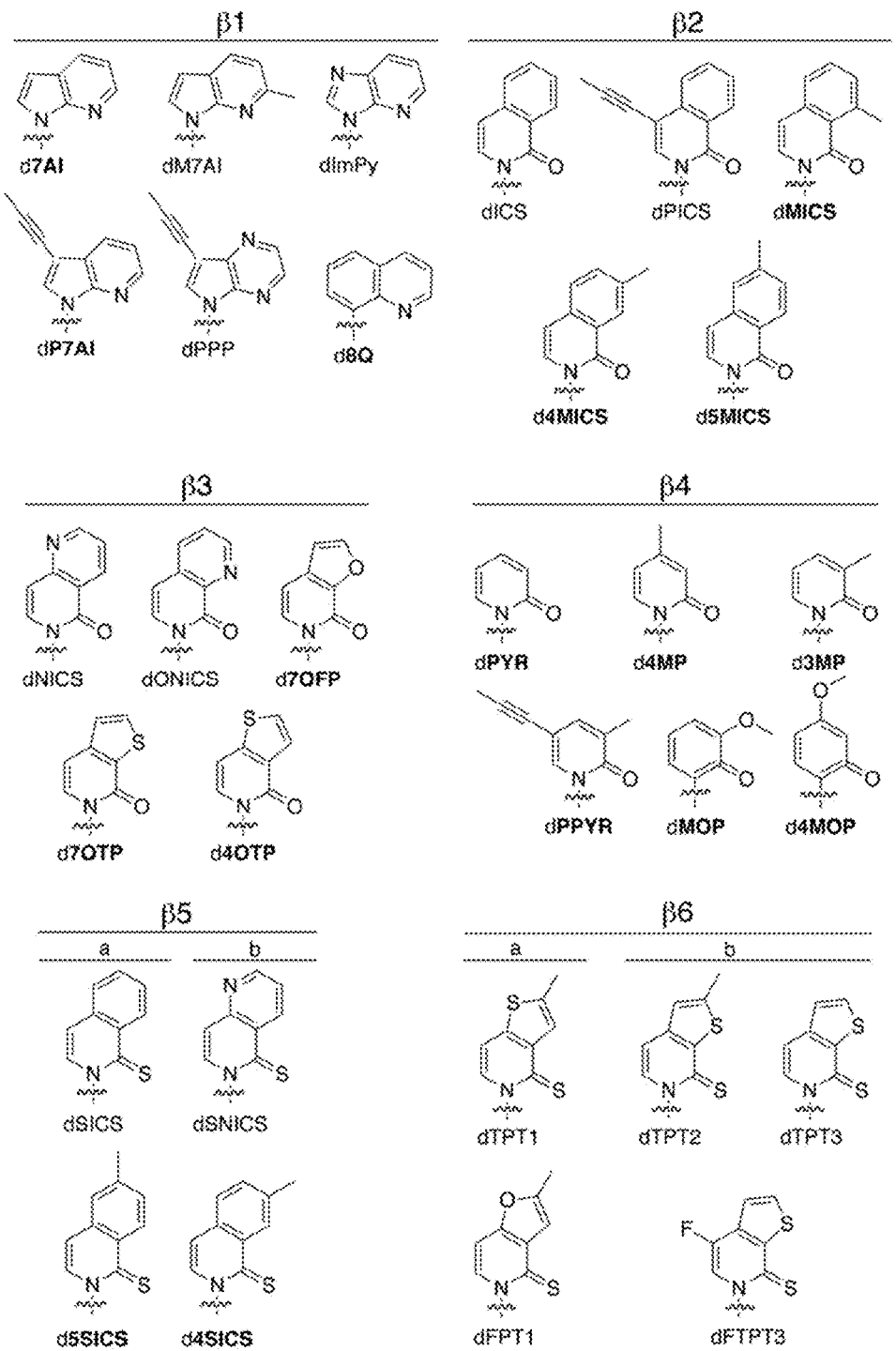
FIG. 9 illustrates 6 groupings of β nucleobase analogs, β1-β6.
Figure 10:
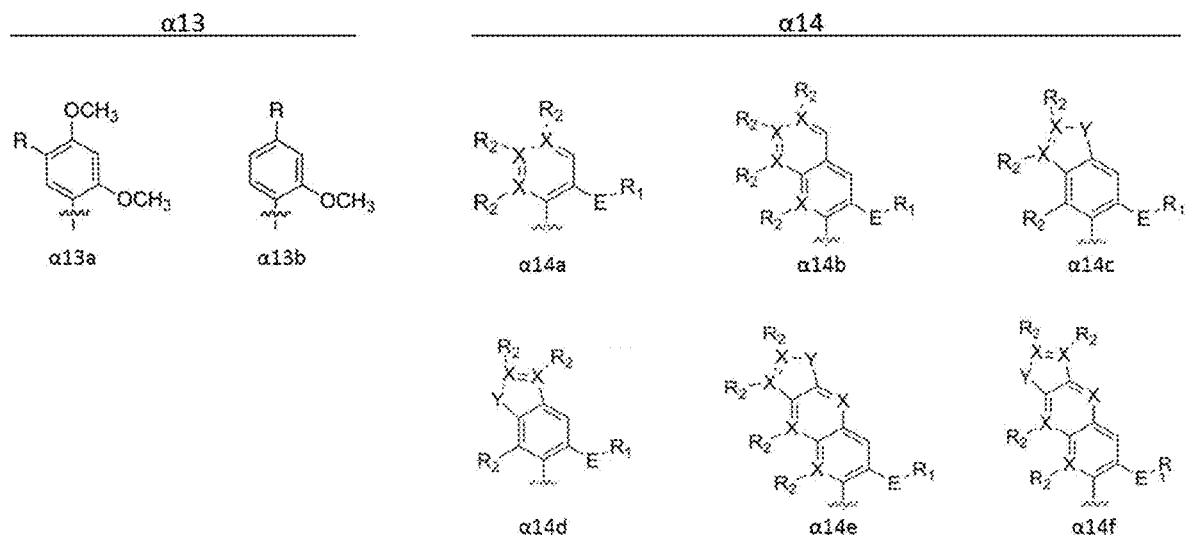
FIG. 10 illustrates 2 groupings of a nucleobase analogs, α13 and α14; wherein each X is independently carbon or nitrogen; wherein each R1 is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each R2 is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each Y is independently sulfur, oxygen, selenium, or secondary amine; wherein each E is independently sulfur, selenium or oxygen.
Figure 11:
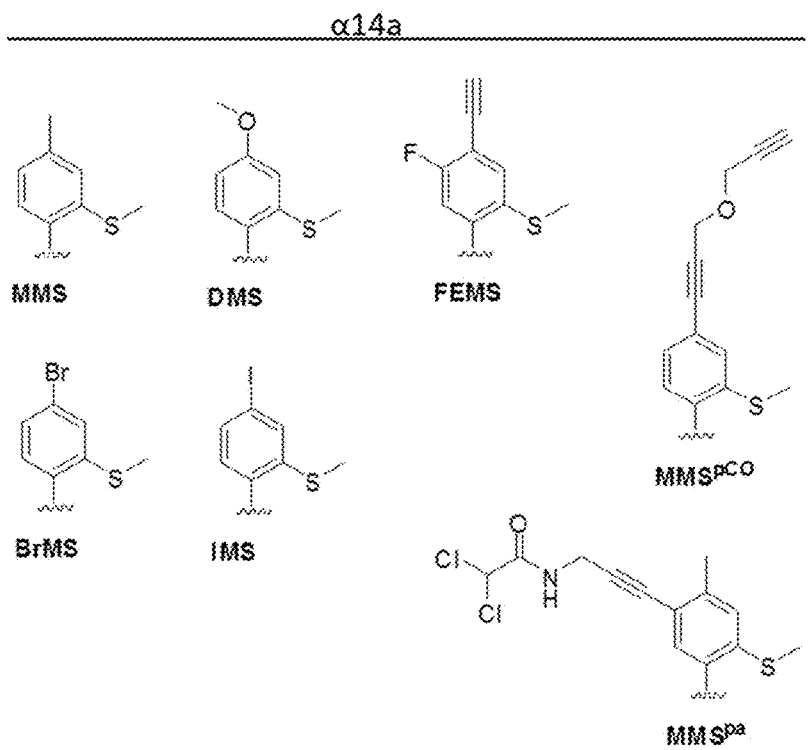
FIG. 11 illustrates examples of α14a nucleobase analogs, including linker-derivatized nucleobase analogs, MMSpCO and MMSPA.
Figure 12:
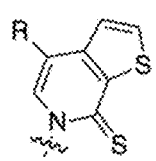
FIG. 12 illustrates 2 groupings of β nucleobase analogs, β7 and β8; wherein each X is independently carbon or nitrogen; wherein each R2 is optional and when present is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently sulfur, selenium or oxygen; and wherein R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded.
Figure 12:
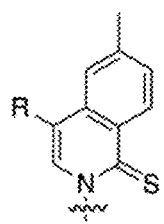
Figure 12:
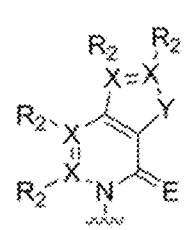
Figure 12:
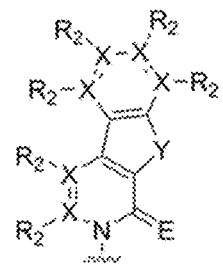
Figure 13:
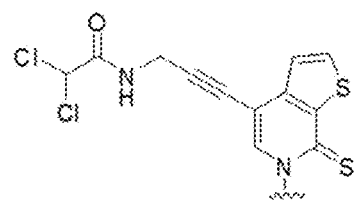
FIG. 13 illustrates examples of β8 linker-derivatized nucleobase analogs.
Figure 13:
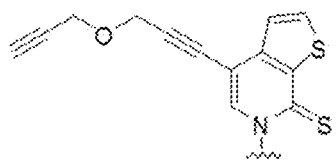

Further provided herein, in various embodiments, are unnatural nucleotides with nucleobase analogs including, α analogs (e.g., any one of FIGS. 8, 10, 11, 15 and derivatives thereof); β analogs (e.g., any one of FIGS. 9, 12, 13, 16 and derivatives thereof); d5SICS$^{CO}$, d5SICS$^{CC}$, dDMO$^{CO}$, dDMO$^{CC}$, dMMO2$^{PCO}$, dMMO2$^{PCC}$, dTPT3, dTPT3$^{PA}$, dTPT3$^A$, dTPT3$^{CO}$, dTPT3$^{CC}$, and ribosyl forms thereof, and analogs thereof (See FIG. 2); in the form of nucleosides, nucleoside 5' triphosphates, and analogs thereof (e.g., ribosyl and 2'-deoxyribosyl), nucleotides and analogs thereof (e.g., ribosyl and 2'-deoxyribosyl, phosphate and phosphorothioate), including nucleotide reagents derived there from for use in RNA/DNA synthesis (DMT-protected phosphoramidites) and for use in enzymatic incorporation into oligonucleotides as by PCR or T7 RNA polymerase-mediate transcription, and incorporated into nucleic acids (oligonucleotides) such as DNA and RNA. The compounds comprising the unnatural nucleobase analogs can also be incorporated into DNA analogs or into RNA analogs, such as PNA, LNA, and other like polynucleotide-analogous polymers. Exemplary nucleobase analogs provided herein include β8 analogs comprising the formulas β8a and β8b, as shown in FIG. 12, wherein each X is independently carbon or nitrogen; wherein each $R_2$ is optional and when present is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently sulfur, selenium or oxygen; and wherein R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded. Examples of β8 analogs include dTPT3 and linker-derivatized analogs thereof. Exemplary nucleobase analogs provided herein include α14 analogs comprising the formulas α14a-α14f, as shown in FIG. 10, wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each Y is independently sulfur, oxygen, selenium, or secondary amine; wherein each E is independently sulfur, selenium or oxygen. Examples of α14 analogs include dMMS, dDMS, dFEMS, dBrMS, dIMS, and linker-derivatized analogs thereof.

Further provided herein, in various embodiments, are unnatural base pairs comprising any one α analog or derivative thereof disclosed herein, and any one β analog or derivative thereof disclosed herein. Derivatives include, but are not limited to, atom substitutions and additions of linker moieties. Linker moieties may be attached to the analogs during synthesis or after nucleobase incorporation into a nucleic acid. Exemplary unnatural base pairs include, but are not limited to, dTPT3-dNaM, dTPT3-dFEMO, dTPT3-dFIMO, dTPT3-dIMO, dFTPT3-dNaM, dFTPT3-dFEMO, dFTPT3-dFIMO, dFTPT3-dIMO. Unnatural base pairs include, but are not limited to, dTPT3-MMS, dTPT3-DMS, dTPT3-FEMS, dTPT3-BrMS, dTPT3-IMS, dTPT3-dDMN, dTPT3-d4OMe, dTPT3-dIQ, dTPT3-d2MN, dTPT3-d3OMe, dTPT3-dQL, dTPT3-d2Np, dTPT3-dDM4, dTPT3-dDM, dTPT3-dBEN, dTPT3-d3FB, dTPT3-dMM1, dTPT3-dMMO1, dTPT3-dDM2, dTPT3-dDM5, dTPT3-d2Py, dTPT3-d5MPy, dTPT3-dEPy, dTPT3-d3MPy, dTPT3-d34DMPy, dTPT3-d45DMPy, dTPT3-d4MPy, dTPT3-d35DMPy, dTPT3-dBP, dTPT3-dBTp, dTPT3-dBF, dTPT3-dIN, dTPT3-dTp, dTPT3-dBTz, dTPT3-dMTp, dTPT3-dAM, dTPT3-dMAN, dTPT3-dDMMAN, dTPT3-dADM, dTPT3-dM MAN, dTPT3-dTOK588, dTPT3-dTOK576, dTPT3-dTOK587, dTPT3-dTOK586, dTPT3-dTOK580, dTPT3-dPhMO, dTPT3-dPyMOl, dTPT3-PyMO2, dTPT3-dPMO1, dTPT3-dPMO2, dTPT3-dPMO3, dTPT3-dFuMO1, dTPT3-dFuMO2, dTPT3-TpMO1, dTPT3-dTpMO2, dTPT3-dFIMO, dTPT3-dIMO, dTPT3-dMIMO, dTPT3-dMEMO, dTPT3-dFEMO, dTPT3-dPrMO, dTPT3-dMMO2, dTPT3-d2OMe, dTPT3-dDMO, dTPT3-dTMO, dTPT3-dNMO, dTPT3-dNOPy, dTPT3-d5FM, dTPT3-dNAM, dTPT3-dAMO1, dTPT3-dAPy, dTPT3-dAMO2, dTPT3-dMAPy, dTPT3-dAMO3, dTPT3-dDMAPy, dTPT3-dFDMO, dTPT3-dVMO, dTPT3-dQMO, dTPT3-dZMO, dTPT3-dCIMO, dTPT3-dTfMO, dTPT3-CNMO, d7AI-dMMS, dM7AI-dMMS, dImPy-dMMS, dP7AI-dMMS, dPPP-dMMS, d8Q-dMMS, dICS-dMMS, dPICS-dMMS, dMICS-dMMS, d4MICS-dMMS, d5MICS-dMMS, dNICS-dMMS, dONICS-dMMS, d7OFP-dMMS, d7OTP-dMMS, d4OTP-dMMS, dPYR-dMMS, d4MP-dMMS, d3MP-dMMS, dPPYR-dMMS, dMOP-dMMS, d4MOP-dMMS, dSICS-dMMS, dSNICS-dMMS, d5SICS-dMMS, d4SICS-dMMS, dTPT1-dMMS, dTPT2-dMMS, dFPT1-dMMS, dFTPT3-dMMS, d7AI-dDMS, dM7AI-dDMS, dImPy-dDMS, dP7AI-dDMS, dPPP-dDMS, d8Q-dDMS, dICS-dDMS, dPICS-dDMS, dMICS-dDMS, d4MICS-dDMS, d5MICS-dDMS, dNICS-dDMS, dONICS-dDMS, d7OFP-dDMS, d7OTP-dDMS, d4OTP-dDMS, dPYR-dDMS, d4MP-dDMS, d3MP-dDMS, dPPYR-dDMS, dMOP-dDMS, d4MOP-dDMS, dSICS-dDMS, dSNICS-dDMS, d5SICS-dDMS, d4SICS-dDMS, dTPT1-dDMS, dTPT2-dDMS, dFPT1-dDMS, dFTPT3-dDMS, d7AI-dFEMS, dM7AI-dFEMS, dImPy-dFEMS, dP7AI-dFEMS, dPPP-dFEMS, d8Q-dFEMS, dICS-dFEMS, dPICS-dFEMS, dMICS-dFEMS, d4MICS-dFEMS, d5MICS-dFEMS, dNICS-dFEMS, dONICS-dFEMS, d7OFP-dFEMS, d7OTP-dFEMS, d4OTP-dFEMS, dPYR-dFEMS, d4MP-dFEMS, d3MP-dFEMS, dPPYR-dFEMS, dMOP-dFEMS, d4MOP-dFEMS, dSICS-dFEMS, dSNICS-dFEMS, d5SICS-dFEMS, d4SICS-dFEMS, dTPT1-dFEMS, dTPT2-dFEMS, dFPT1-dFEMS, dFTPT3-dFEMS, d7AI-dBrMS, dM7AI-dBrMS, dImPy-dBrMS, dP7AI-dBrMS, dPPP-dBrMS, d8Q-dBrMS, dICS-dBrMS, dPICS-dBrMS, dMICS-dBrMS, d4MICS-dBrMS, d5MICS-dBrMS, dNICS-dBrMS, dONICS-dBrMS, d7OFP-dBrMS, d7OTP-dBrMS, d4OTP-dBrMS, dPYR-dBrMS, d4MP-dBrMS, d3MP-dBrMS, dPPYR-dBrMS, dMOP-dBrMS, d4MOP-dBrMS, dSICS-dBrMS, dSNICS-dBrMS, d5SICS-dBrMS, d4SICS-dBrMS, dTPT1-dBrMS, dTPT2-dBrMS, dFPT1-dBrMS, dFTPT3-dBrMS, d7AI-dIMS, dM7AI-dIMS, dImPy-dIMS, dP7AI-dIMS, dPPP-dIMS, d8Q-dIMS, dICS-dIMS, dPICS-dIMS, dMICS-dIMS, d4MICS-dIMS, d5MICS-dIMS, dNICS-dIMS, dONICS-dIMS, d7OFP-dIMS, d7OTP-dIMS, d4OTP-dIMS, dPYR-dIMS, d4MP-dIMS, d3MP-dIMS, dPPYR-dIMS, dMOP-dIMS, d4MOP-dIMS, dSICS-dIMS, dSNICS-dIMS, d5SICS-dIMS, d4SICS-dIMS, dTPT1-dIMS, dTPT2-dIMS, dFPT1-dIMS, and dFTPT3-dIMS; wherein one or two unnatural nucleobases of the unnatural base pair may be derivatized with a linker. Exemplary unnatural base pairs of this disclosure further include any pair described in Example 1. Exemplary β analogs include those which are presented in FIGS. 9, 12, and 13. Exemplary β nucleobase analogs include β8 analogs comprising the formulas β8a and β8b, as shown in FIG. 12, wherein each X is independently carbon or nitrogen; wherein each $R_2$ is optional and when present is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently sulfur, selenium or oxygen; and wherein R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded. Examples of α analogs include dTPT3, d5SICS, dFTPT3 and derivatives or analogs thereof. Exemplary a analogs include those which are presented in FIGS. 8, 10, and 11. Exemplary α analogs include α14 analogs comprising the formulas α14a-α14f, as shown in FIG. 10, wherein each X is independently carbon or nitrogen; wherein each $R_1$ is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each $R_2$ is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each R is optional and when present, is independently hydrogen, alkyl, alkenyl, alkynyl, methoxy, methanethiol, methaneseleno, halogen, cyano, azide group, a reactive linker comprising a reactive center adapted to bond to a cargo reagent comprising a cargo and a group of reactivity complementary to the reactive center, coupled linker to which a cargo is bonded; wherein each Y is independently sulfur, oxygen, selenium, or secondary amine; wherein each E is independently sulfur, selenium or oxygen. Examples of α analogs include dMMS, dDMS, dBrMS, dIMS, dFEMS, dNAM, dMMO2, dDMO, dEMO, dFEMO, and derivatives or analogs thereof. In some embodiments, an unnatural base pair includes an α analog and a natural base. In some embodiments, an unnatural base pair includes a β analog and a natural base. Further provided herein, in some aspects, are unnatural base pairs comprising the same two unnatural nucleoside analogs or derivatives thereof.

An unnatural base pair, in various aspects, comprises one unnatural nucleobase disclosed herein (e.g. α analog or derivative thereof, β analog or derivative thereof) and another unnatural nucleobase including, but not limited to, 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. The α analogs of the unnatural base pair include, without limitation, dMMS, dDMS, dBrMS, dIMS, dFEMS, dNAM, dMMO2, dDMO, dEMO, dFEMO, and derivatives or analogs thereof. The β analogs of the unnatural base pair include, without limitation, dTPT3, d5SICS, and dFTPT3.

In some embodiments, the unnatural nucleobases and unnatural base pairs disclosed herein have efficient incorporation and extension with natural polymerases. In some embodiments, the unnatural nucleobases and unnatural base pairs disclosed herein have efficient incorporation and extension with modified polymerases. The effect of an unnatural nucleobase or unnatural nucleobase derivative on polymerase recognition is assessed, in exemplary embodiments, by determining the steady-state efficiency (e.g., second order rate constant $k_{cat}/K_M$) with which the polymerase synthesizes an unnatural base pair, by insertion of the unnatural nucleotide opposite its complementary base in a template, and extends the resulting unnatural primer terminus, by insertion of the next correct natural nucleotide. Corresponding rates of synthesis and extension for mispairs with natural nucleotides may also be measured to determine fidelity. In some embodiments, polymerases do not need to be modified to improve incorporation or extension rates. The embodiments and examples disclosed herein may be performed with any known polymerase. Polymerases include naturally-occurring polymerases and any modified variations thereof, including, but not limited to, mutants, recombinants, fusions, genetic modifications, chemical modifications, synthetics, and analogs. Naturally-occurring polymerases and modified variations thereof are not limited to polymerases which retain the ability to catalyze a polymerization reaction. In some instances, the naturally-occurring and/or modified variations thereof retain the ability to catalyze a polymerization reaction. Mutant polymerases include polymerases wherein one or more amino acids are replaced with other amino acids (naturally or non-naturally occurring), and polymerases having one or more amino acid insertions or deletions. In some embodiments a polymerase refers to fusion proteins comprising at least two portions linked to each other, for example, where one portion comprises a peptide that can catalyze the polymerization of nucleotides into a nucleic acid strand is linked to another portion that comprises a second moiety, such as, a reporter enzyme or a processivity-modifying domain. One exemplary embodiment of such a polymerase is T7 DNA polymerase, which comprises a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\sigma$, $\lambda$, $\mu$, $\iota$, and $\kappa$, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Archaeal DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (*D. tok* Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

In some embodiments, a polymerase has a specificity for an unnatural nucleotide comprising an a or β nucleobase analog that is at least about 10%, 20%, 30%, 40%, 50%, 60%, 70%, 80%, 90%, 95%, 97%, 98%, 99%, 99.5%, 99.99% of the specificity of the polymerase toward a natural nucleotide. In some embodiments, a polymerase has a specificity for an unnatural nucleotide comprising an a or β nucleobase analog and a modified sugar that is at least about 10%, 20%, 30%, 40%, 50%, 60%, 70%, 80%, 90%, 95%, 97%, 98%, 99%, 99.5%, 99.99% of the specificity of the polymerase toward a natural nucleotide and/or the unnatural nucleotide without the modified sugar. In some embodiments, a polymerase has a specificity for an unnatural nucleotide comprising a linker-derivatized α or β nucleobase analog that is at least about 10%, 20%, 30%, 40%, 50%, 60%, 70%, 80%, 90%, 95%, 97%, 98%, 99%, 99.5%, 99.99% the specificity of the polymerase toward a natural nucleotide and/or the unnatural nucleotide without the linker. In some embodiments, the unnatural nucleobase is dTPT3. In some embodiments, the unnatural nucleobase is dMMS. In some embodiments, the unnatural nucleobase is dDMS. In some embodiments, the unnatural nucleobase is dBrMS. In some embodiments, the unnatural nucleobase is IMS. In some embodiments, the unnatural nucleobase is dFEMS. In some embodiments, the unnatural nucleobase is MMS$^{PCO}$. In some embodiments, the unnatural nucleobase is dMMS$^{PA}$. In some embodiments, the unnatural nucleobase is dFTPT3. In some embodiments, the unnatural nucleobase is dTPT$^{PA}$. In some embodiments, the unnatural nucleobase is dTPT3$^{CO}$. In some embodiments, the unnatural nucleobase comprises the formula α14a or a derivative or analog thereof. In some embodiments, the unnatural nucleobase comprises the formula α14b or a derivative or analog thereof. In some embodiments, the unnatural nucleobase comprises the formula α14c or a derivative or analog thereof. In some embodiments, the unnatural nucleobase comprises the formula α14d or a derivative or analog thereof. In some embodiments, the unnatural nucleobase comprises the formula α14e or a derivative or analog thereof. In some embodiments, the unnatural nucleobase comprises the formula α14f or a derivative or analog thereof. In some embodiments, the unnatural nucleobase comprises the formula β8a or a derivative or analog thereof. In some embodiments, the unnatural nucleobase comprises the formula β8b or a derivative or analog thereof.

Polymerases can be characterized according to their fidelity when used with a particular natural and/or unnatural nucleotide or collections of natural and/or unnatural nucleotides, wherein the unnatural nucleotide comprises an α or β nucleobase analog disclosed herein. In various embodiments, fidelity generally refers to the accuracy with which a polymerase incorporates correct nucleotides into a growing oligonucleotide when making a copy of an oligonucleotide template. Polymerase fidelity can be measured as the ratio of correct to incorrect natural and unnatural nucleotide incorporations when the natural and unnatural nucleotides are present, e.g., at equal concentrations, to compete for strand synthesis at the same site in the polymerase-strand-template nucleic acid binary complex. DNA polymerase fidelity can be calculated as the ratio of $(k_{cat}/K_M)$ for the natural and unnatural nucleotide and $(k_{cat}/K_M)$ for the incorrect natural and unnatural nucleotide; where $k_{cat}$ and $K_M$ are Michaelis-Menten parameters in steady state enzyme kinetics. In some embodiments, a polymerase has a fidelity value of at least about 100, 1000, 10,000, 100,000, or $1\times10^6$, with or without a proofreading activity. In some embodiments, a polymerase has a fidelity value of at least about 100, 1000, 10,000, 100,000, or $1\times10^6$ for unnatural nucleotide incorporation. In some embodiments, the unnatural nucleotide is dTPT3TP or a derivative thereof, and its corresponding nucleobase on the template oligonucleotide is dNAM or a derivative thereof. In some embodiments, the unnatural nucleotide is dNaMTP or a derivative thereof, and its corresponding nucleobase on the template oligonucleotide is dTPT3 or a derivative thereof. In some embodiments, the unnatural nucleotide comprises β8a or a derivative thereof, and its corresponding nucleobase on the template oligonucleotide comprises α14a or a derivative thereof. In some embodiments, the unnatural nucleotide comprises β8a or a derivative thereof, and its corresponding nucleobase on the template oligonucleotide comprises α14b or a derivative thereof. In some embodiments, the unnatural nucleotide comprises β8a or a derivative thereof, and its corresponding nucleobase on the template oligonucleotide comprises α14c or a derivative thereof. In some embodiments, the unnatural nucleotide comprises β8a or a derivative thereof, and its corresponding nucleobase on the template oligonucleotide comprises α14d or a derivative thereof. In some embodiments, the unnatural nucleotide comprises β8a or a derivative thereof, and its corresponding nucleobase on the template oligonucleotide comprises α14e or a derivative thereof. In some embodiments, the unnatural nucleotide comprises β8a or a derivative thereof, and its corresponding nucleobase on the template oligonucleotide comprises α14f or a derivative thereof. In some embodiments, the unnatural nucleotide comprises β8b or a derivative thereof, and its corresponding nucleobase on the template oligonucleotide comprises α14a or a derivative thereof. In some embodiments, the unnatural nucleotide comprises β8b or a derivative thereof, and its corresponding nucleobase on the template oligonucleotide comprises α14b or a derivative thereof. In some embodiments, the unnatural nucleotide comprises β8b or a derivative thereof, and its corresponding nucleobase on the template oligonucleotide comprises α14c or a derivative thereof. In some embodiments, the unnatural nucleotide comprises β8b or a derivative thereof, and its corresponding nucleobase on the template oligonucleotide comprises α14d or a derivative thereof. In some embodiments, the unnatural nucleotide comprises β8e or a derivative thereof, and its corresponding nucleobase on the template oligonucleotide comprises α14e or a derivative thereof. In some embodiments, the unnatural nucleotide comprises β8f or a derivative thereof, and its corresponding nucleobase on the template oligonucleotide comprises α14f or a derivative thereof.

The unnatural base pairs exemplified herein, in some embodiments, are synthesized/amplified with natural base pair-like efficiency and fidelity. Unnatural base pairs comprise, in various embodiments, any a nucleobase analog or derivative thereof, and/or any β nucleobase analog or derivative thereof. Examples of β analogs include dTPT3, d5SICS, dFTPT3 and derivatives or analogs thereof. Examples of α analogs include dMMS, dDMS, dBrMS, dIMS, dFEMS, dNAM, dMMO2, dDMO, dEMO, dFEMO, and derivatives or analogs thereof. In some embodiments, an unnatural base pair is efficiently amplified in a variety of different sequence contexts, including GC- and AT-rich sequences, randomized sequences, and sequences comprising multiple unnatural nucleobase pairs, with greater than 90%, 91%, 92%, 93%, 94%, 95%, 96%, 97%, 97%, 98%, 99%, 99.1%, 99.2%, 99.3%, 99.4%, 99.5%, 99.6%, 99.7%, 99.85, 99.9 or higher fidelity per doubling. For example, an unnatural nucleobase pair comprising one or more unnatural nucleobases has a synthesis efficiency and/or fidelity that is at least 60%, 65%, 70%, 75%, 80% 85%, 86%, 87%, 88%, 89%, 90%, 91%, 92%, 93%, 94%, 95%, 96%, 97%, 98%, or 99% similar to an amplification efficiency and/or fidelity of a natural base pair. As another example, an unnatural nucleobase pair comprising one or more unnatural nucleobases has a synthesis efficiency and/or fidelity that is at most 15%, 14%, 13%, 12%, 11%, 10%, 9%, 8%, 7%, 6%, 5%, 4%, 3%, 2%, 1%, or 0.5% less efficient and/or accurate than that of a natural base pair. In some embodiments, an unnatural nucleobase pair is transcribed with good efficiency and selectivity in both strand contexts (e.g., dX must template YTP insertion and dY must template XTP insertion). In some embodiments, relative to the rate at which a fully natural sequence is transcribed, the incorporation of an unnatural nucleotide does not reduce the rate of full-length transcription. In some embodiments, relative to the rate at which a fully natural sequence is transcribed, the incorporation of an unnatural nucleotide reduces the rate of full-length transcription by a factor less than 2, 3, 4, 5, 6, 7, 8, 9, 10, 11, 12, 13, 14, 15, 16, 17, 18, 19, 20, 25, 30, 35, or 40. In some embodiments, the unnatural base pair comprises dTPT3 or a derivative or analog thereof, and dNaM or a derivative or analog thereof. In some embodiments, the unnatural base pair comprises dTPT3 or a derivative or analog thereof, and dNaM or a derivative or analog thereof. In some embodiments, the unnatural base pair comprises dTPT3 or a derivative or analog thereof, and dNaM or a derivative or analog thereof. In some embodiments, the unnatural base pair comprises dTPT3 or a derivative or analog thereof, and dNaM or a derivative or analog thereof. In some embodiments, the unnatural base pair comprises dTPT3 or a derivative or analog thereof, and dNaM or a derivative or analog thereof. In some embodiments, the unnatural base pair comprises β8a or a derivative or analog thereof, and α14a or a derivative or analog thereof. In some embodiments, the unnatural base pair comprises β8a or a derivative or analog thereof, and α14b or a derivative or analog thereof. In some embodiments, the unnatural base pair comprises β8a or a derivative or analog thereof, and α14c or a derivative or analog thereof. In some embodiments, the unnatural base pair comprises β8a or a derivative or analog thereof, and α14d or a derivative or analog thereof. In some embodiments, the unnatural base pair comprises β8a or a derivative or analog thereof, and α14e or a derivative or analog thereof. In some embodiments, the unnatural base pair comprises β8a or a derivative or analog thereof, and α14f or a derivative or analog thereof. In some embodiments, the unnatural base pair comprises β8b or a derivative or analog thereof, and α14a or a derivative or analog thereof. In some embodiments, the unnatural base pair comprises β8b or a derivative or analog thereof, and α14b or a derivative or analog thereof. In some embodiments, the unnatural base pair comprises β8b or a derivative or analog thereof, and α14c or a derivative or analog thereof. In some embodiments, the unnatural base pair comprises β8b or a derivative or analog thereof, and α14d or a derivative or analog thereof. In some embodiments, the unnatural base pair comprises β8b or a derivative or analog thereof, and α14e or a derivative or analog thereof. In some embodiments, the unnatural base pair comprises β8b or a derivative or analog thereof, and α14f or a derivative or analog thereof.

Further provided herein, in various embodiments, are unnatural base pairs comprising one or more unnatural nucleobases (e.g. α nucleobase, β nucleobase, or α nucleobase and β nucleobase), wherein one or two nucleobases comprise a linker. A linker comprises a reactive center. Exemplary reactive centers include, but are not limited to, alkyl, alkenyl, alkynyl, phenyl, benzyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, imide, azide, azo, cyanate, isocyanate, nitrate, nitrile, isonitrile, nitrosooxy, nitro, nitroso, pyridyl, sulfhydryl, sulfide, disulfide, sulfinyl, sulfo, thiocyanate, isothiocyanante, carbonothioyl, phoshino, phosphono, phosphate, borono, boronate, borino, borinate, and a combination thereof. An example of a linker-derivatized nucleobase is TPT3$^R$ shown in FIG. 2, wherein the superscript R indicates the linker. In some embodiments, a linker is modified with a protecting group, for example, TPT3$^{PA}$, where the linker is a protected propargyl linker.

In some embodiments, a nucleobase analog provided herein comprises an amino-functional linker or a protected amino-functional linker (e.g., dX$^{PA}$). In certain embodiments, the amino-functional linker is 3-aminopropyn-1-yl. In some embodiments, a nucleobase analog provided herein comprises an alkyne-azide ether linker for derivatization via click chemistry or a protected alkyne-azide ether linker for derivatization via click chemistry. In certain embodiments, the alkyne-azide ether linker is 4-oxahepat-1,6-diyn-1-yl. In some embodiments, a nucleobase analog provided herein comprises an alkyne-azide trimethylene linker for derivatization via click chemistry or a protected alkyne-azide trimethylene linker for derivatization via click chemistry. In certain embodiments, the alkyne-azide trimethylene linker is hepta-1,6-diyn-1-yl. In some embodiments, X is a β nucleoside analog having any of the formulas from FIGS. 9, 12, 13, and 16. In some embodiments, X is ICS, PICS, MICS, 4MICS, 5MICS, NICS, ONICS, SICS, SNICS, 5SICS, 4SICS, 7OFP, 7OTP, TPT2, TPT3, or FTPT3. In some embodiments, X is an α nucleoside analog having any of the formulas from FIGS. 8, 10, 11, and 15. In some embodiments, X is FIMO, MIMO, FEMO, PrMO, EMO, MEMO, IMO, MMO2, DMO, NMO, SFM, 2OMe, TMO, FDMO, VMO, ZMO, CIMO, TfMO, CNMO, MMS, DMS, BrMS, IMS, FEMS, NAM, or QMO.

In some embodiments, a linker is a propinyl linker, such as those used with natural nucleotides. These linkers comprise propargyl amines, with the amine serving as a reactive site to attach other functionalities.

In various embodiments, a linker-derivatized nucleobase comprises a spacer. An exemplary spacer is acetamido-hexanamide. A spacer may be hydrophilic. A spacer may connect a linker to a functional group. Spacers include, but are not limited to, Spacer C3 (3-carbon spacer), Spacer C6 (6-carbon spacer), photo-cleavable spacer, hexanediol spacer, Spacer 9 (triethylene glycol spacer), Spacer C12 (12-carbon spacer), Spacer 18 (18-atom hexa-ethyleneglycol spacer), and 1',2'-Dideoxyribose spacer.

An unnatural nucleobase pair comprising one or two linker-derivatized nucleobases, in some instances, is amplified with an efficiency and fidelity that is similar to that of a natural base pair or a non-linker derivatized unnatural base pair. For example, an unnatural nucleobase pair comprising one or two linker-derivatized unnatural nucleobases has a synthesis efficiency and/or fidelity that has at least 60%, 65%, 70%, 75%, 80% 85%, 86%, 87%, 88%, 89%, 90%, 91%, 92%, 93%, 94%, 95%, 96%, 97%, 98%, or 99% similar to a synthesis efficiency and/or fidelity of a natural base pair or a non-linker derivatized unnatural base pair. As another example, an unnatural nucleobase pair comprising one or two linker-derivatized unnatural nucleobases has a synthesis efficiency and/or fidelity that is at most 15%, 14%, 13%, 12%, 11%, 10%, 9%, 8%, 7%, 6%, 5%, 4%, 3%, 2%, 1%, or 0.5% less efficient and/or accurate than that of a natural base pair or a non-linker derivatized unnatural base pair. In some embodiments, an unnatural nucleobase pair comprises dTPT3$^{PA}$. In some embodiments, an unnatural nucleobase pair comprises dTPT3$^{CO}$. In some embodiments, an unnatural nucleobase pair comprises dMMS$^{PCO}$. In some embodiments, an unnatural nucleobase pair comprises dMMS$^{PA}$. In some embodiments, an unnatural nucleobase pair comprises dNaM$^R$. In some embodiments, an unnatural nucleobase pair comprises dMMO2$^R$. In some embodiments, an unnatural nucleobase pair comprises dDMO$^R$. In some embodiments, an unnatural nucleobase pair comprises d5SICS$^R$. In some embodiments, an unnatural nucleobase pair comprises dMMS$^R$. In some embodiments, an unnatural nucleobase pair comprises dDMS$^R$. In some embodiments, an unnatural nucleobase pair comprises dFEMS$^R$. In some embodiments, an unnatural nucleobase pair comprises dBrMS$^R$. In some embodiments, an unnatural nucleobase pair comprises dIMS$^R$.

In some embodiments, a linker-derivatized unnatural nucleobase has an increased insertion efficiency during oligonucleotide synthesis, as compared to the same unnatural nucleobase which does not comprise a linker. In some embodiments, a linker-derivatized unnatural nucleobase has a decreased insertion efficiency during oligonucleotide synthesis, as compared to the same unnatural nucleobase which does not comprise a linker. In some instances, a linker-derivatized unnatural nucleobase has about the same insertion efficiency during oligonucleotide synthesis, as compared to the same unnatural nucleobase which does not comprise a linker. In some embodiments, a protected linker-derivatized unnatural nucleobase has an increased insertion efficiency during oligonucleotide synthesis, as compared to the same unnatural nucleobase which does not comprise a protected linker. In some embodiments, a protected linker-derivatized unnatural nucleobase has a decreased insertion efficiency during oligonucleotide synthesis, as compared to the same unnatural nucleobase which does not comprise a protected linker. In some instances, a protected linker-derivatized unnatural nucleobase has about the same efficiency during oligonucleotide synthesis, as compared to the same unnatural nucleobase which does not comprise a protected linker.

Exemplary methods for analyzing unnatural base pair synthesis efficiency (insertion of an unnatural nucleobase opposite its partner in a template) and extension (continued primer elongation) are provided herein. One or both of the nucleobases in an unnatural base pair, in various embodiments, may be a linker-derivatized unnatural nucleobase. One method uses a presteady-state assay. The assay is based on determining, under a fixed set of conditions, the amount of a primer (e.g. 23-mer) that is extended by addition of the unnatural nucleotide opposite its complementary nucleotide in a template (e.g., 45-mer) by a polymerase (e.g., the Klenow fragment of E. coli DNA polymerase I). In this assay, the efficiency of unnatural base pair synthesis is characterized by measuring the percent incorporation (% inc) at a given concentration of the unnatural and next correct triphosphate, for example using a ratio such as [24-mer+25-mer][23-mer+24-mer+25-mer]. In this assay, the efficiency of extension is characterized by measuring the percent extension (% ext) at a given concentration of the next correct nucleotide and saturating concentrations of unnatural nucleotide, for example using a ratio [25-mer]/[24-mer+25-mer]. Results from an exemplary presteady-state assay are shown in Table 1, wherein the unnatural triphosphate is 5SICS, FPT1, TPT1, TPT2, TPT3, FTPT3, TPT3$^{PA}$, or 5SICS$^{PA}$. In some embodiments, the percent incorporation of an unnatural nucleobase is at least 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In some embodiments, the percent extension of a next correct nucleotide following insertion of an unnatural nucleobase is at least 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90% or greater. In some embodiments, synthesis efficiency is increased by derivatizing the unnatural nucleobase. For example, by the addition of a linker, a protected linker, and/or a linker conjugated to a cargo molecule. As another example, derivatization includes atom substitutions, additions, or deletions. In some embodiments, percent extension is increased by derivatizing the unnatural nucleobase. Derivatization of an unnatural nucleobase, in some instances, increases by at least 1-2 orders of magnitude the efficiency of insertion of the nucleotide complementary to the base pair in the template. This increase in efficiency may be due to an increase $k_{cat}$ and a decreased $K_M$.

TABLE 1

Presteady-state kinetics.

| dXTP | % Incorporation[a] | % Extension[b] |
|---|---|---|
| 5SICS | 57.0 ± 0.2 | 15.1 ± 1.1 |
| FPT1 | 7.2 ± 0.2 | 32.0 ± 1.5 |
| TPT1 | 28.7 ± 0.5 | 8.8 ± 0.2 |
| TPT2 | 65.7 ± 0.5 | 34.5 ± 0.5 |
| TPT3 | 72.3 ± 0.5 | 49.8 ± 1.3 |
| FTPT3 | 66.3 ± 0.5 | 33.8 ± 0.2 |
| TPT3$^{PA}$ | 68.3 ± 0.4 | 31.5 ± 0.7 |
| 5SICS$^{PA}$ | 7.0 ± 0.2 | 5.5 ± 0.1 |

[a]Incorporation assay conditions: 40 nM unnatural triphosphate, 2 μM dCTP, 10 s.
[b]Extension assay conditions: 10 μM unnatural triphosphate, 2 μM dCTP, 10 s. dXTPs are paired with dNaM.

Further provided herein are replication evaluation methods. In one method, a template nucleic acid duplex comprising an unnatural base pair (e.g., dTPT3-dNaM or analogs thereof), is amplified by PCR. In one example, a set of PCR reactions employs 48 cycles with OneTaq polymerase. In another example, a set of PCR reactions employs 20 cycles of amplification with exonuclease-negative Taq. Efficiency is determined by monitoring the amplification level. Fidelity, generally defined as unnatural base pair extension per doubling, is determined from the percentage of the amplified DNA that retains the unnatural base pair. The percentage of amplified DNA that retains the unnatural base pair may be determined from the relative peak intensities of a sequencing chromatogram. In some embodiments, the fidelity of unnatural base pair replication is at least 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98% or 99.99%. Replication of an unnatural base pair may proceed with little or no sequence bias, wherein little sequence bias indicates that an unfavorable sequence decreases fidelity by less than 1%. Exemplary fidelities are described in Example 1 and shown in Tables 4, 5, and 6.

Further provided herein, in various embodiments, are oligonucleotides, including single-stranded and double-stranded (e.g., duplex) DNA and/or RNA, comprising one or more unnatural nucleobases described herein (e.g, any a nucleobase or analog or derivative thereof and/or any β nucleobase or analog or derivative thereof). The nucleobase may be any a nucleobase or β nucleobase described herein, including those in FIGS. 2, 8, 9, 10, 11, 12, 13, 15, and 16. A double-stranded oligonucleotide includes a DNA-DNA duplex, DNA-RNA hybrid duplex, and RNA-RNA duplex. In some embodiments, the oligonucleotide comprises a linker-derivatized nucleobase.

In some embodiments, an oligonucleotide comprises 1, 2, 3, 4, 5, 6, 7, 8, 9, 10, 11, 12, 13, 14, 15, 20, 25, 30, 35, 40, 45, 50 or more unnatural nucleobases. In some embodiments, the percentage of unnatural nucleobases in an oligonucleotide is between about 0% and about 1%, between about 0% and about 2%, between about 0% and about 3%, between about 0% and about 4%, between about 0% and about 5%, between about 0% and about 10%, between about 1% and about 10%, between about 1% and about 15%, between about 1% and about 20%, between about 5% and about 10%, between about 5% and about 20%, between about 10% and about 30%, between about 1% and about 50%, or between about 1% and about 100%.

Examples of oligonucleotides comprising one or more unnatural nucleobases include, but are not limited to, DNA aptamers and RNA aptamers. DNA and RNA aptamers include, but are not limited to, primers and molecular beacons. A DNA aptamer may include a barcode.

In some embodiments, an oligonucleotide comprises dTPT3 or a derivative or analog thereof. In some embodiments, an oligonucleotide comprises d5SICS or a derivative or analog thereof. In some embodiments, an oligonucleotide comprises dNaM or a derivative or analog thereof. In some embodiments, an oligonucleotide comprises dMMS or a derivative or analog thereof. In some embodiments, an oligonucleotide comprises dDMS or a derivative or analog thereof. In some embodiments, an oligonucleotide comprises dFEMS or a derivative or analog thereof. In some embodiments, an oligonucleotide comprises dBrMS or a derivative or analog thereof. In some embodiments, an oligonucleotide comprises dIMS or a derivative or analog thereof. In some embodiments, an oligonucleotide comprises β8a or a derivative or analog thereof. In some embodiments, an oligonucleotide comprises β8b or a derivative or analog thereof. In some embodiments, an oligonucleotide comprises α14a or a derivative or analog thereof. In some embodiments, an oligonucleotide comprises α14b or a derivative or analog thereof. In some embodiments, an oligonucleotide comprises α14c or a derivative or analog thereof. In some embodiments, an oligonucleotide comprises α14d or a derivative or analog thereof. In some embodiments, an oligonucleotide comprises α14e or a derivative or analog thereof. In some embodiments, an oligonucleotide comprises α14f or a derivative or analog thereof.

In some embodiments, an oligonucleotide comprises dTPT3 or a derivative or analog thereof, and dNaM or a derivative or analog thereof. In some embodiments, an oligonucleotide comprises a dTPT3-dNaM base pair. In some embodiments, an oligonucleotide comprises one or more base pairs selected from dTPT3-dFEMO, dTPT3-dFIMO, dTPT3-dIMO, dFTPT3-dNaM, dFTPT3-dFEMO, dFTPT3-dFIMO, and dFTPT3-dIMO. In some embodiments, an oligonucleotide comprises one or more base pairs selected from dTPT3-MMS, dTPT3-DMS, dTPT3-FEMS, dTPT3-BrMS, dTPT3-IMS, dTPT3-dDMN, dTPT3-d4OMe, dTPT3-dIQ, dTPT3-d2MN, dTPT3-d3OMe, dTPT3-dQL, dTPT3-d2Np, dTPT3-dDM4, dTPT3-dDM, dTPT3-dBEN, dTPT3-d3FB, dTPT3-dMM1, dTPT3-dMMO1, dTPT3-dDM2, dTPT3-dDM5, dTPT3-d2Py, dTPT3-d5MPy, dTPT3-dEPy, dTPT3-d3MPy, dTPT3-d34DMPy, dTPT3-d45DMPy, dTPT3-d4MPy, dTPT3-d35DMPy, dTPT3-dBP, dTPT3-dBTp, dTPT3-dBF, dTPT3-dIN, dTPT3-dTp, dTPT3-dBTz, dTPT3-dMTp, dTPT3-dAM, dTPT3-dMAN, dTPT3-dDMMAN, dTPT3-dADM, dTPT3-dMMAN, dTPT3-dTOK588, dTPT3-dTOK576, dTPT3-dTOK587, dTPT3-dTOK586, dTPT3-dTOK580, dTPT3-dPhMO, dTPT3-dPyMO1, dTPT3-PyMO2, dTPT3-dPMO1, dTPT3-dPMO2, dTPT3-dPMO3, dTPT3-dFuMO1, dTPT3-dFuMO2, dTPT3-TpMO1, dTPT3- dTpMO2, dTPT3-dFIMO, dTPT3-dIMO, dTPT3-dMIMO, dTPT3-dMEMO, dTPT3-dFEMO, dTPT3-dPrMO, dTPT3-dMMO2, dTPT3-d2OMe, dTPT3-dDMO, dTPT3-dTMO, dTPT3-dNMO, dTPT3-dNOPy, dTPT3-d5FM, dTPT3-dNAM, dTPT3-dAMO1, dTPT3-dAPy, dTPT3-dAMO2, dTPT3-dMAPy, dTPT3-dAMO3, dTPT3-dDMAPy, dTPT3-dFDMO, dTPT3-dVMO, dTPT3-dQMO, dTPT3-dZMO, dTPT3-dCIMO, dTPT3-dTfMO, dTPT3-CNMO, d7AI-dMMS, dM7AI-dMMS, dImPy-dMMS, dP7AI-dMMS, dPPP-dMMS, d8Q-dMMS, dICS-dMMS, dPICS-dMMS, dMICS-dMMS, d4MICS-dMIMS, d5MICS-dMMS, dNICS-dMMS, dONICS-dMIMS, d7OFP-dMMS, d7OTP-dMMS, d4OTP-dMMS, dPYR-dMMS, d4MP-dMMS, d3MP-dMMS, dPPYR-dMMS, dMOP-dMMS, d4MOP-dMMS, dSIC5-dMIMS, dSNICS-dMMS, d5SICS-dMMS, d4SICS-dMMS, dTPT1-dMMS, dTPT2-dMMS, dFPT1-dMIMS, dFTPT3-dMMS, d7AI-dDMS, dM7AI-dDMS, dImPy-dDMS, dP7AI-dDMS, dPPP-dDMS, d8Q-dDMS, dICS-dDMS, dPICS-dDMS, dMICS-dDMS, d4MICS-dDMS, d5MICS-dDMS, dNICS-dDMS, dONICS-dDMS, d7OFP-dDMS, d7OTP-dDMS, d4OTP-dDMS, dPYR-dDMS, d4MP-dDMS, d3MP-dDMS, dPPYR-dDMS, dMOP-dDMS, d4MOP-dDMS, dSICS-dDMS, dSNICS-dDMS, d5SICS-dDMS, d4SICS-dDMS, dTPT1-dDMS, dTPT2-dDMS, dFPT1-dDMS, dFTPT3-dDMS, d7AI-dFEMS, dM7AI-dFEMS, dImPy-dFEMS, dP7AI-dFEMS, dPPP-dFEMS, d8Q-dFEMS, dICS-dFEMS, dPICS-dFEMS, dMICS-dFEMS, d4MICS-dFEMS, d5MICS-dFEMS, dNICS-dFEMS, dONICS-dFEMS, d7OFP-dFEMS, d7OTP-dFEMS, d4OTP-dFEMS, dPYR-dFEMS, d4MP-dFEMS, d3MP-dFEMS, dPPYR-dFEMS, dMOP-dFEMS, d4MOP-dFEMS, dSICS-dFEMS, dSNICS-dFEMS, d5SICS-dFEMS, d4SICS-dFEMS, dTPT1-dFEMS, dTPT2-dFEMS, dFPT1-dFEMS, dFTPT3-dFEMS, d7AI-dBrMS, dM7AI-dBrMS, dImPy-dBrMS, dP7AI-dBrMS, dPPP-dBrMS, d8Q-dBrMS, dICS-dBrMS, dPICS-dBrMS, dMICS-dBrMS, d4MICS-dBrMS, d5MICS-dBrMS, dNICS-dBrMS, dONICS-dBrMS, d7OFP-dBrMS, d7OTP-dBrMS, d4OTP-dBrMS, dPYR-dBrMS, d4MP-dBrMS, d3MP-dBrMS, dPPYR-dBrMS, dMOP-dBrMS, d4MOP-dBrMS, dSICS-dBrMS, dSNICS-dBrMS, d5SICS-dBrMS, d4SICS-dBrMS, dTPT1-dBrMS, dTPT2-dBrMS, dFPT1-dBrMS, dFTPT3-dBrMS, d7AI-dIMS, dM7AI-dIMS, dImPy-dIMS, dP7AI-dIMS, dPPP-dIMS, d8Q-dIMS, dICS-dIMS, dPICS-dIMS, dMICS-dIMS, d4MICS-dIMS, d5MICS-dIMS, dNICS-dIMS, dONICS-dIMS, d7OFP-dIMS, d7OTP-dIMS, d4OTP-dIMS, dPYR-dIMS, d4MP-dIMS, d3MP-dIMS, dPPYR-dIMS, dMOP-dIMS, d4MOP-dIMS, dSICS-dIMS, dSNICS-dIMS, d5SICS-dIMS, d4SICS-dIMS, dTPT1-dIMS, dTPT2-dIMS, dFPT1-dIMS, dFTPT3-dIMS; wherein one or two unnatural nucleobases of the unnatural base pair may be derivatized with a linker.

An oligonucleotide comprising an unnatural nucleobase disclosed herein may further comprise one or more additional unnatural bases, including, but not limited to, 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-aminopropyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl aminomethyluracil, 5-methoxy aminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

An oligonucleotide comprising an unnatural nucleobase disclosed herein, may further comprise an unnatural sugar moiety, including, but not limited to, a modification at the 2' position: OH; substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2F; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-OCH3, 2'—O(CH2)2OCH3 wherein the alkyl, alkenyl and alkynyl may be substituted or substituted C1-C10, alkyl, C2-C10 alkenyl, C2-C10 alkynyl, —O[(CH2)n O]mCH3, —O(CH2)nOCH3, —O(CH2)n NH2, —O(CH2)n CH3, —O(CH2)n-ONH2, and —O(CH2)nON[(CH2)n CH3)]2, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some embodiments, the oligonucleotide comprising an unnatural nucleobase disclosed herein, further comprises an unnatural backbone. An unnatural backbone includes, but is not limited to, phosphorothioate, chiral phosphorothioate, phosphorodithioate, phosphotriester, aminoalkylphosphotriester, C1-C10 phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

Methods for determining the stability of oligonucleotide duplexes comprising unnatural base pairs (with or without linkers) include thermodynamic analysis by circular dichroism (CD) measurements and UV melting experiments. In some embodiments, DNA duplex stability studies are employed to facilitate the selection of a suitable unnatural nucleotide base pair, unnatural nucleobase, or unnatural nucleobase derivatives or substitutions. Suitably selected unnatural base pairs include those which increase oligonucleotide hybridization fidelity at other positions within the duplex. Suitably selected unnatural base pairs include those which increase oligonucleotide duplex stability. Suitably selected nucleobases may be used to optimize oligonucleotides for biotechnological or therapeutic applications where high fidelity hybridization and discrimination is critical. In some instances, an unnatural base pair is at least 90%, 91%, 92%, 93%, 94%, 95%, 96%, 97%, 98%, 99% or more, as stable as a natural base pair in an oligonucleotide duplex. In some instances, the Tm of a duplex comprising one or more unnatural base pairs is less than 10° C., 9° C., 8° C., 7° C., 6° C., 5° C., 4.5° C., 4° C., 3.5° C., 3° C., 2.9° C., 2.8° C., 2.7° C., 2.6° C., 2.5° C., 2.4° C., 2.3° C., 2.2° C., 2.1° C., 2° C., 1.9° C., 1.8° C., 1.7° C., 1.6° C., 1.5° C., 1.4° C., 1.3° C., 1.2° C., 1.1° C., 1° C., 0.9° C., 0.8° C., 0.7° C., 0.6° C., 0.5° C., 0.4° C., 0.3° C., 0.2° C., 0.1° C. below the Tm of the same duplex wherein the one or more unnatural nucleobases are replaced with one or more natural nucleobases. In some embodiments, the presence of an unnatural base pair in an oligonucleotide duplex does not significantly perturb duplex structure.

In some embodiments, an oligonucleotide comprising a linker-derivatized nucleobase allows for the site-specific modification of that DNA or RNA during or after enzymatic synthesis. An unnatural nucleotide disclosed herein (e.g. a nucleotide comprising an unnatural α a or β nucleobase analog), in some instances, is modified with a linker that enables the attachment of different functional groups (e.g., cargo) without ablating polymerase recognition. Site specific functionalities include, but are not limited to fluorophores, NMR handles for characterization (e.g., F19), IR probes (e.g., azido and cyano groups), biotin (e.g. to facilitate identification and/or purification), affinity tags, liposomes, and nanoparticles. In one embodiment, a linker provides bioconjugation via cross-coupling (e.g., iodo group). In one embodiment, a linker provides a handle for bioconjugation via click chemistry (e.g., azido and alkyne substituents). In one embodiment, an oligonucleotide comprising a linker-derivatized nucleobase is useful as a primer and/or molecular beacon.

Further provided herein, in various embodiments, is the use of any nucleoside analogs disclosed herein (α or β), or analogs or derivatives thereof, in site-specific cleavage or functionalization of an oligonucleotide. In some embodiments, a nucleoside analog comprises one or more linkers configured for site-specific modification. Examples of nucleotide analogs comprising a linker moiety include, but are not limited to, d5SICSCO, d5SICSCC, dDMOCO, dDMOCC, dMMO2pCO, dMMO2pCC, dTPT3, dTPT3A, dTPT3PA, dTPT3CO, dMMSpCO, dMMSPA, and dTPT3CC, or ribosyl forms thereof, or analogs thereof. Provided herein, in various embodiments, are compositions of matter per se of the functionalized oligonucleotides, methods of preparation of the functionalized oligonucleotides, and methods of use of the functionalized oligonucleotides. Various embodiments provide dTPT3, dTPT3PA, dTPT3A, dTPT3CO, and dTPT3CC, or other linker-derivatized analogs of dTPT3, incorporated into oligonucleotides and the further reaction or derivatization of these unnatural nucleobase analogs incorporated in a oligonucleotide with various reagents for selective reaction with the unnatural nucleobase analogs in a oligonucleotide wherein the naturally occurring nucleobases (A, T, G, C, U) do not react with these reagents to any appreciable extent. The dTPT3-based family of linker-bearing unnatural nucleotides is especially central, as we have found that they are more efficiently replicated by DNA polymerases than are base pairs that include d5SICS or its linker-derivatized variants, which will significantly facilitate many of the potential applications. In some embodiments, the percent incorporation of an unnatural nucleotide comprising a linker into an oligonucleotide is at least 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In some embodiments, the percent extension of a next correct nucleotide into an oligonucleotide, wherein the next correct nucleotide follows incorporation of an unnatural nucleotide comprising a linker, is at least 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90% or greater. In some embodiments, the addition of a site-specific functionality decreases the percent incorporation of an unnatural nucleotide into an oligonucleotide by at most about 50%, 45%, 40%, 35%, 30%, 25%, 20%, 15%, 14%, 13%, 12%, 11%, 10%, 9%, 8%, 7%, 6%, 5%, 4%, 3%, 2%, or 1%. In some embodiments, the fidelity of a linker-derivatized unnatural nucleotide is at least 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98% or 99.99%. Accordingly, in various embodiments, provided herein are methods for using the linker-derivatized unnatural nucleotides to produce DNA or RNA that is site-specifically modified with another molecule of interest. In some embodiments, site-specific inclusion of different functionalities occurs either pre- or post-amplification. In some embodiments, site-specific functionalization is employed for SELEX applications.

An exemplary strategy to produce DNA or RNA that is site-specifically modified with another molecule of interest is referred to as the phosphorothioate strategy (FIG. 3), which relies on the site-specific incorporation of a phosphorothioate group into an DNA or RNA via a ribo or deoxyribo α-thiotriphosphate of one of the unnatural nucleosides from FIG. 1 or 2. After incorporation into DNA or RNA, the phosphorothioate may be used to couple reagents that bear γ-bromo-α,β-unsaturated carbonyl-, iodo (or bromo)acetyl-, or aziridinylsulfonamide moieties to produce site-specifically functionalized DNA or RNA. Alternatively, after incorporation into DNA or RNA, the phosphorothioate may be used to site-specifically cleave the DNA or RNA using iodine in an alkaline solution or iodoethanol, respectively. Thus, the phosphorothioate strategy provides site-specific modification of the nucleic acid backbone, and provides for a method of site-specific cleavage of the oligonucleotide chain.

Figure 4:
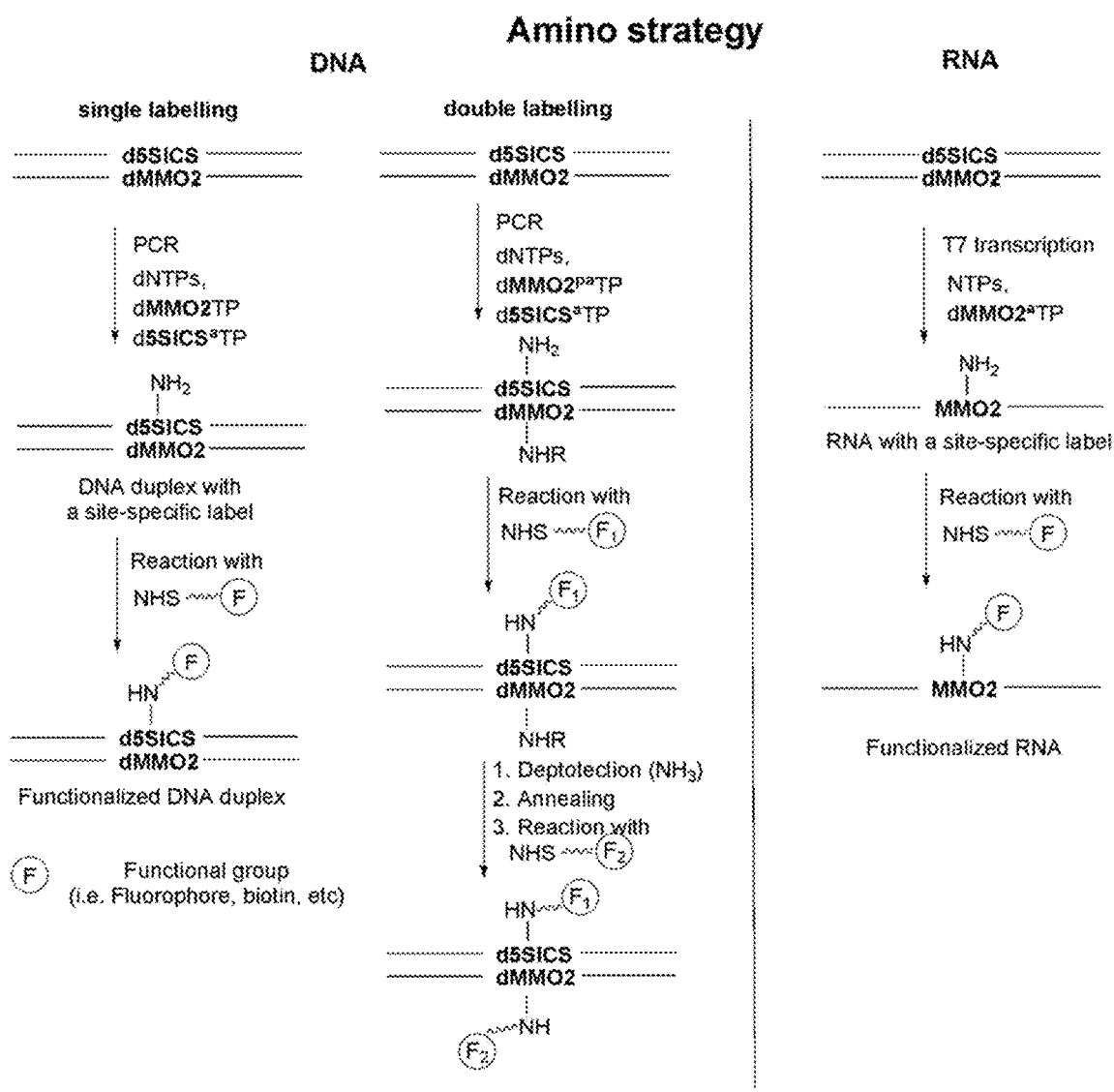
FIG. 4 shows an overview of the amino-based post-synthesis site-specific labeling strategy. The linker-modified nucleotides can also be directly incorporated into the template DNA using standard solid phase synthesis of oligonucleotides and the corresponding phosphoroamidites.

Another strategy to produce DNA or RNA that is site-specifically modified with another molecule or interest, referred to as the linker strategy (FIGS. 4 and 5), makes use of the derivatization of an unnatural nucleobases with a linker (FIG. 2) that may be used to attach functional groups of interest, either before polymerization (via PCR or T7 RNA polymerase-mediated transcription using an appropriate functionalized nucleobase triphosphate reagent that is incorporated into the DNA or RNA chain being synthesized), or by reaction of the linker of the unnatural nucleobase after incorporation into the oligonucleotide chain with an appropriate functionalization reagent, e.g., an NHS containing reagent also comprising the desired functional group, wherein the NHS reacts with the free amino group of an amino-functionalized unnatural nucleobase such as d5SICS$^A$, dMMO2$^A$, or dTPT3$^A$. FIG. 4 also shows the amino functionalization linker strategy using d5SICS$^A$ and dMMO2$^{PA}$ that allows site-specific double labeling of duplex DNA.

For example, functionalization can be accomplished after incorporation into the oligonucleotide of the unnatural nucleobase with the linker bearing a primary amino group (e.g., dTPT3$^A$). More specifically, the functionalization can be carried out via reaction of the primary amino (e.g., propargylamino group) and a cargo-bearing reagent including an N-hydroxysuccinimide (NETS) ester (FIG. 4). The analogs developed for this application include d5SICS$^A$, d5SICS$^{PA}$, dMMO2$^A$, dMMO2$^{PA}$, dTPT3$^{PA}$, and dTPT3$^A$ (recall that "A" refers to the nucleotide with a propargyl amine and "PA" refers to the same linker with a protecting group, see FIG. 2 and its caption). The use of dTPT3$^{PA}$, bearing a protected primary propargylamino group, and dTPT3$^A$, bearing the primary propargylamino group, for sequence-specific functionalization of oligonucleotides, is disclosed and claimed herein.

Figure 5:
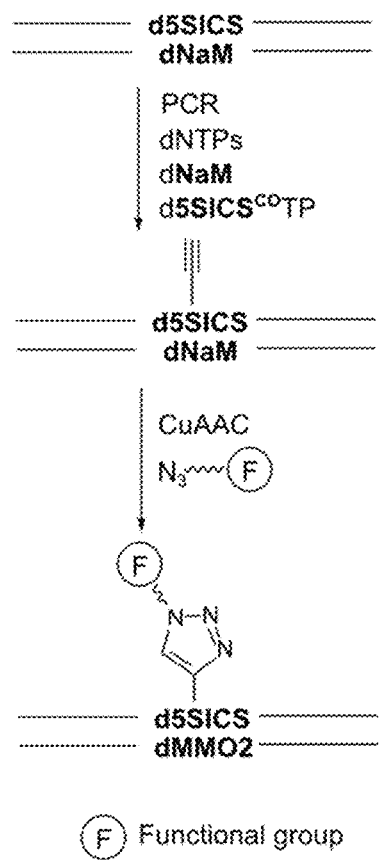
FIG. 5 shows an overview of the click chemistry-based post-synthesis site-specific labeling strategy. The linker-modified nucleotides can also be directly incorporated into the template DNA using standard solid phase synthesis of oligonucleotides and the corresponding phosphoroamidites.

The site-specific functionalization of a oligonucleotide can also be accomplished using the Copper(I)-catalyzed Azide-Alkyne Cycloaddition (CuAAC) (i.e. "Click chemistry" linker strategy; FIG. 5), and for these applications d5SICS$^{CO}$, d5SICS$^{CC}$, dDMO$^{CO}$, dDMO$^{CC}$, dMMO2P$^{CO}$, dMMO2P$^{CC}$, dTPT3$^{CO}$ and dTPT3$^{CC}$ (FIG. 2), may be used. In each case, the ribosyltriphosphates of the unnatural nucleobases can be employed for transcription to produce site-specifically labeled RNA, and the deoxyribosyltriphosphates of the unnatural nucleobases can be used, e.g., in PCR, to produce site-specifically labeled DNA. The unnatural nucleobases comprising an acetylenic (alkynyl) linker group suitable for use in CuAAC conjugation, d5SICS$^{CO}$, d5SICS$^{CC}$, dDMO$^{CO}$, dDMO$^{CC}$, dMMO2P$^{CO}$, dMMO2P$^{CC}$, dTPT3$^{CO}$ and dTPT3$^{CC}$, methods of their preparation, and methods of their use in preparing such site-specifically labeled oligonucleotides, are disclosed and claimed herein.

Figure 3:
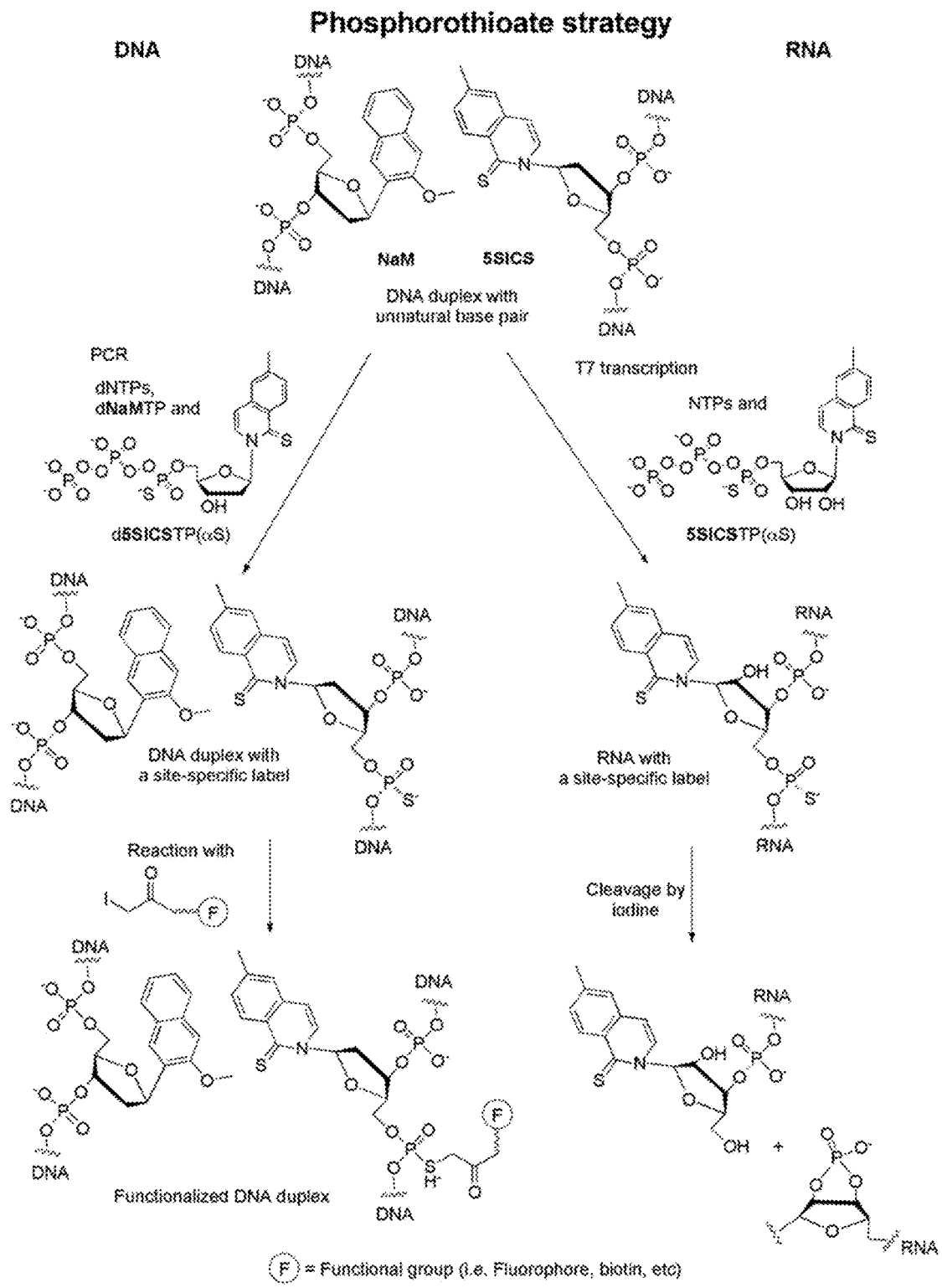
FIG. 3 shows an overview of the phosphorothioate-based post-synthesis site-specific labeling strategy.

Demonstration of general phosphorothioate strategy (FIG. 3). To demonstrate the feasibility of our system, we have prepared the α-thiotriphosphate of the unnatural nucleotide, d5SICS (d5SICS-αS), and incorporated it into DNA opposite its cognate unnatural nucleotide dNaM, using standard PCR. The amplification efficiency and fidelity of incorporation of d(5SICS-αS)TP is greater than 99% and virtually identical to results obtained with d5SICS. To functionalize this unnatural base pair, we reacted the site-specifically incorporated phosphorothioate bond with iodoacetyl-PEG$_2$-biotin to label the DNA duplex with the biotin functionality.[8] To characterize this site-specific adduct, we incubated it in the presence of streptavidin and then quantified the functionalization by gel shift assay. We were able to convert 60-70% of the phosphorothioate bond to the functionalized derivative, which is a standard efficiency (70%) for labeling protocols previously reported in literature (See Fidanza, J. A.; Ozaki, H.; McLaughlin, L. W., Site-specific labeling of DNA sequences containing phosphorothioate diesters. *J. Am. Chem. Soc.* 2002, 114 (14), 5509-5517). These conjugated derivatives show high stability under conditions typical for heat denaturation of DNA duplexes, i.e. at 50° C. overnight within the range of pH 6.0-8.3 (<10% decomposition), as well as for at 95° C. for 3 minutes at pH 8.3 (<5% decomposition). We envision that the phosphorothioate strategy can be equally well employed with other unnatural base pairs, including d5SICS-dMMO2 and d5SICS-dNaM.

Provided herein, in various embodiments, is a phosphorothioate strategy using an unnatural base pair dTPT3-dNaM, dTPT3-dMMO2, or dTPT3-dDMO, and linker-derivatized variants thereof.

The phosphorothioate and linker-based strategies are not mutually exclusive and when combined should allow for a given site to be simultaneously modified with up to three different functional groups, one attached to a first nucleobase of a nucleobase pair, a second attached to a second nucleobase of a nucleobase pair, and a third attached to the backbone immediately 5' to an unnatural nucleotide.

Demonstration of linker strategy with primary amine (FIG. 4). To further demonstrate the feasibility of our system, we have synthesized and characterized the amino- and protected amino-linker derivatized variants of d5SICS and dMMO2 (FIG. 2). When paired in DNA opposite their cognate unnatural partners, we showed that each was well amplified by PCR and transcribed into RNA. Coupling of DNA containing dMMO2$^A$ or d5SICS$^A$ prepared by PCR amplification with NETS-ester biotin proceeds with 55% and 70% efficiency, respectively.

Figure 7:
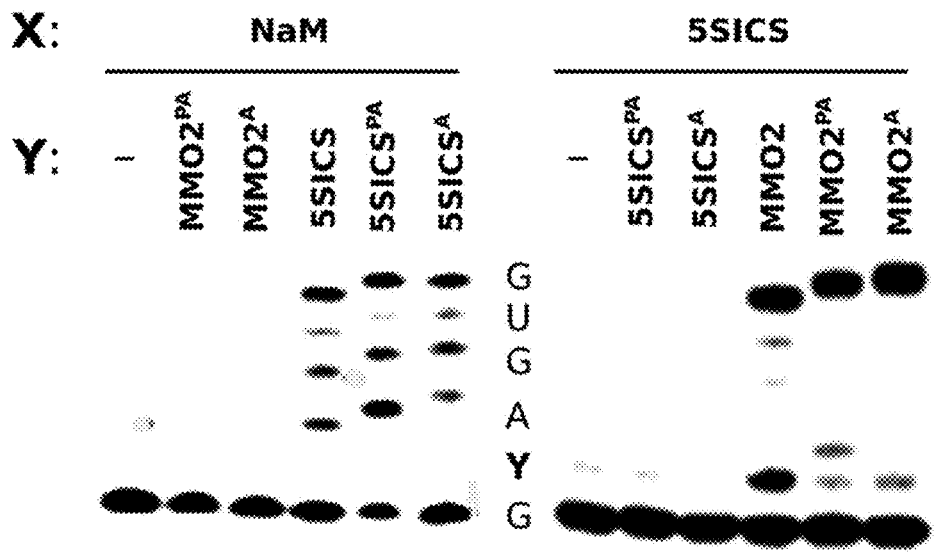
FIG. 7 shows gel electrophoresis data confirming the full-length transcription of RNA containing linker-derivatized analogs of 5SICS or MMO2. Sequences disclosed as SEQ ID NOS: 14-16, respectively, in order of appearance.

We have shown that the ribonucleotide triphosphates of SSICS$^{PA}$, SSICS$^A$, MMO2$^{PA}$ or MMO2$^A$, are transcribed into RNA by T7 RNA polymerase with high efficiency and fidelity (FIG. 7).

Provided herein, in various embodiments, is the site-specific modification of DNA or RNA using dTPT3$^L$-dNaM, dTPT3$^L$-dMMO2, or dTPT3$^L$-(d)DMO (where R is a linker, e.g. R=H for dTPT3, R=3-aminopropyn-1-yl for dTPT3$^A$, R=dichloroacetyl-3-aminopropyn-1-yl for dTPT3$^{PA}$, R=4-oxahepat-1,6-diyn-1-yl for dTPT3$^{CO}$, R=hepta-1,6-diyn-1-yl for dTPT3$^{CC}$).

Demonstration of general linker strategy with alkynes (FIG. 5). To further demonstrate the feasibility of our system, we have synthesized and characterized the alkynyl functionalized variants of d5SICS, dDMO, and dMMO2, including d5SICS$^{CO}$, d5SICS$^{CC}$, dDMO$^{CO}$, dDMO$^{CC}$, dMMO2P$^{CO}$, dMMO2$^{PCC}$ (FIG. 2) each of these alkyne-functionalized unnatural nucleotide should be efficiently PCR amplified when present in DNA. Once amplified, the DNA containing, for example, the d5SICS$^{CO}$-dNaM base pair, may be efficiently site-specifically modified with small molecules or one or more proteins possessing azide groups using Click chemistry, e.g., copper-catalyzed click reactions. We have also demonstrated the utility of dEMO, and dFEMO (FIG. 2) for incorporation into oligonucleotides and the use of these functionalized oligonucleotides in click chemistry reactions with azides to functionalize the oligonucleotides in a site-specific manner.

Figure 6:
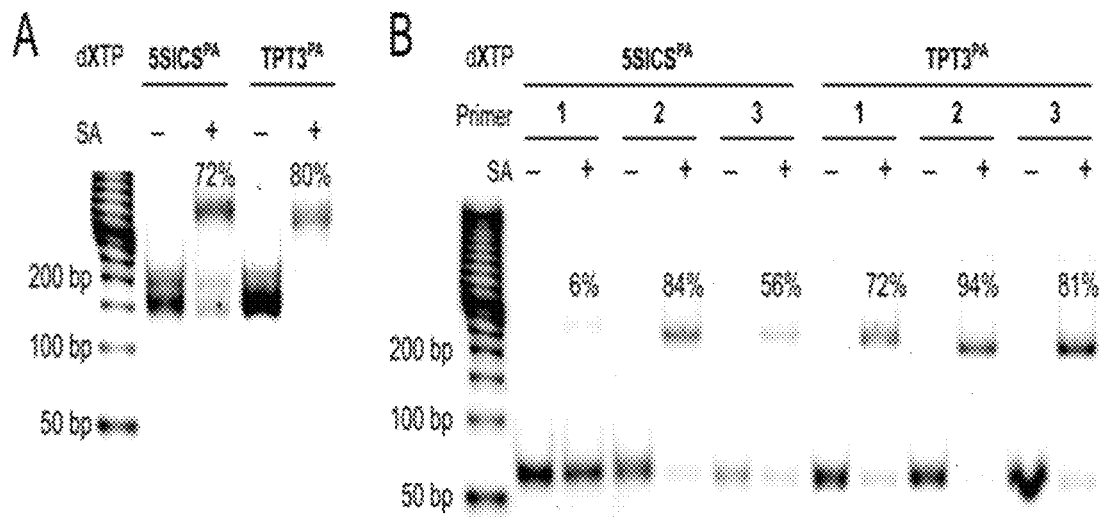
FIG. 6 shows representative data illustrating the post-amplification labeling of DNA analyzed via streptavidin (SA) gel shift. The faster migrating band corresponds to dsDNA, while the slower migrating band corresponds to the 1:1 complex between dsDNA and streptavidin. (A) The labeling efficiency is 72% with d5SICSPA-dNaM and 80% with dTPT3PA-dNaM. (B) The labeling efficiency is 6%, 84%, and 56% with d5SICSPA-dNaM at the first (primer 1: unnatural base pair at position 1), ninth (primer 2: unnatural base pair at position eleven), and eleventh (primer 3: unnatural base pair at position nine) position. The corresponding labeling efficiencies with dTPT3PA-dNaM are 72%, 94%, and 81%.

Demonstration of linker strategy with dTPT3$^{PA}$ (FIG. 6). Addition of a linker to the d5SICS and dMMO2 scaffolds significantly reduces the efficiency with which the unnatural nucleotides are enzymatically incorporated in DNA, which is expected to limit their practical applications. However, we have found that the dTPT3 scaffold is much more tolerant to linker addition (FIG. 6). For example, dTPT3$^{PA}$TP is incorporated into a primer opposite dNaM in a temple by DNA polymerases with virtually the same efficiency and fidelity as a natural base pair. Accordingly, provided herein, in various embodiments, is the use of unnatural nucleobases based on the dTPT3 scaffold, including dTPT3$^{PA}$ (protected amino-functional linker), dTPT3$^A$ (amino-functional linker), and dTPT3$^{CO}$ (alkyne-azide ether linker for derivatization via click chemistry), and dTPT3$^{CC}$ (alkyne-azide trimethylene linker for derivatization via click chemistry) in the synthesis of site-specific functionalized oligonucleotides.

Scheme 1 illustrates examples of dTPT3 with different linkers that could be used to site-specifically modify DNA or RNA.

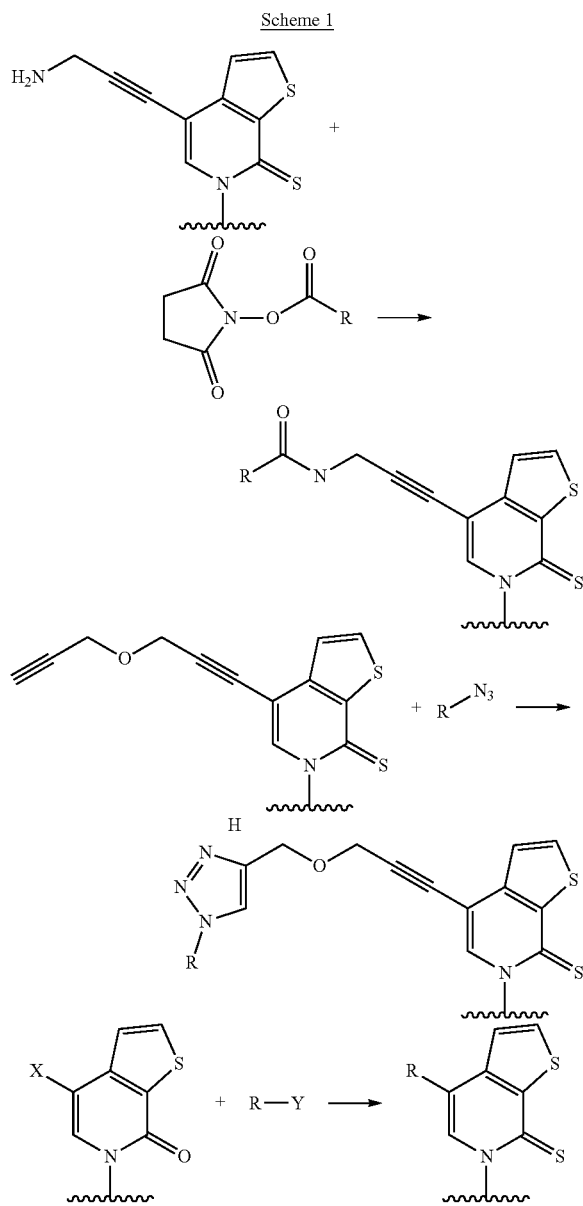

Scheme 1

For clarity only the dTPT3 scaffold nucleobase moieties are shown, but it is understood that they are used as nucleotides. The functionalization reactions can be carried out either prior to or after incorporation of the unnatural nucleobases into a oligonucleotide. Scheme 1, top reaction, illustrates the use of dTPT3$^A$ comprising a primary amine-bearing linker that is acylated using an activated ester to form an amide, wherein the R group comprises the cargo. The middle reaction of Scheme 1 illustrates the use of dTPT3$^{CO}$ (dTPT3$^{CC}$ could also be used) comprising an alkynyl-bearing linker reacted with an azide to yield a triazole via Click chemistry, wherein the R group of the triazole that is formed comprises the cargo. The bottom reaction illustrates the most general case for a dTPT3 scaffold derivative bearing a linker group R$_1$ with a reactive moiety that can selectively form a covalent bond with a R$_2$ group that includes a reactive moiety complementary to the reactive moiety of the linker, for example, thiol-maleimide, hydrazine-aldehyde, etc.

In one embodiment, a linker comprising an azide reactive group is useful for attaching an aklyne comprising cargo through a click reaction. In one embodiment, a linker comprising a thiol group can form reversible disulfide bonds or irreversible bonds with a variety of cargo accepting groups, including, but not limited to, maleimide, bromide, iodide, sulphonyl derivatives, active esters and isothiocyanate derivatives. In one embodiment, a linker comprising an azide group is reactive with a cargo molecule comprising a phosphine group.

In one embodiment, an oligonucleotide comprising one or more linker-derivatized unnatural nucleobases is configured for use as a molecular beacon. The fluorophore of the molecular beacon is a cargo molecule attached to a reactive center of the linker-derivatized unnatural nucleobase. Exemplary fluorophore cargo molecules include, but are not limited to, 6-FAM, Fluorescein, Cy3™, JOE (6-carboxy-4', 5'-dichloro-2',7'-dimethoxyfluorescein), Cy5™, TAMRA, MAX, TET™, ROX (carboxy-X-rhodamine), TYE™ 563, Hexachlorofluorescein, TEX 615, TYE™ 665, TYE 705, Alexa Fluor® 488, Alexa Fluor® 532, Alexa Fluor® 546, Alexa Fluor® 594, Alexa Fluor® 647, Alexa Fluor® 660, Alexa Fluor® 750, IRDye® 800CW, ATTO™ 488, ATTO™ 532, ATTO™ 550, ATTO™ 565, ATTO™ Rho101, ATTO™ 590, ATTO™ 633, ATTO™ 647N, Rhodamine Green™-X, Rhodamine Red™-X, 5-TAMRA™, Texas Red®-X, Lightcycler® 640, and Dy 750.

An unnatural base pair, in some embodiments, allows for the site-specific inclusion of different functionalities into DNA for Systematic Evolution of Ligands by Exponential Enrichment (SELEX) applications, including the generation of DNA and/or RNA aptamers. DNA and RNA aptamers have a variety of targets, including nucleic acids, small molecules, peptides, carbohydrates, and cells. SELEX includes the creation of a library of nucleic acid molecules, contacting the library with target molecules to select nucleic acid molecules which bind to the target molecules, and amplifying library members which bound to target molecules. Additional rounds of selection and amplification continue until sufficient aptamers are recovered. An aptamer, in one aspect, includes any unnatural base disclosed herein. In some embodiments, a SELEX experiment, wherein library components comprise unnatural nucleobases, generates an aptamer affinity against a target molecule in 1, 2, 3, 4, 5, 6, 7, 8, 9, 10 or fewer rounds of selection than a library which does not comprise unnatural nucleobases. In some embodiments, an aptamer comprising one or more unnatural nucleobases has a greater affinity for a target molecule than an aptamer containing only natural nucleobases. The addition of one or more unnatural nucleobases in a SELEX library increases the chemical and structural diversity of the resulting DNA or RNA aptamers. In some embodiments, an unnatural aptamer has at least a nanomolar affinity against its target molecule. In some embodiments, an unnatural aptamer has at least a picomolar affinity against its target molecule. For example, an unnatural aptamer has an affinity for its target molecule which is between 1 and 1,000 pM. In some embodiments, an unnatural aptamer has at least a femtomolar affinity for its target molecule. For example, an unnatural aptamer has an affinity for its target molecule which is between 1 and 1,000 fM. An unnatural aptamer selected using SELEX may comprise 1, 2, 3, 4, 5, 6, 7, 8, 9, 10, 15, 20 or more unnatural nucleobases. In some embodiments, an unnatural aptamer comprises dTPT3 or a derivative or analog thereof. In some embodiments, an unnatural aptamer comprises a nucleobase having the formula α14a or a derivative or analog thereof. In some embodiments, an unnatural aptamer comprises a nucleobase having the formula α14b or a derivative or analog thereof. In some embodiments, an unnatural aptamer comprises a nucleobase having the formula α14c or a derivative or analog thereof. In some embodiments, an unnatural aptamer comprises a nucleobase having the formula α14d or a derivative or analog thereof. In some embodiments, an unnatural aptamer comprises a nucleobase having the formula α14e or a derivative or analog thereof. In some embodiments, an unnatural aptamer comprises a nucleobase having the formula α14f or a derivative or analog thereof. In some embodiments, an unnatural aptamer comprises a nucleobase having the formula β8a or a derivative or analog thereof. In some embodiments, an unnatural aptamer comprises a nucleobase having the formula β8b or a derivative or analog thereof.

Various combinations of the components set forth above in regard to exemplary reaction mixtures and reaction methods can be provided in a kit form. Such a kit can include individual components that are separated from each other, for example, being carried in separate vessels or packages. A kit can include one or more sub-combinations of the components set forth herein, the one or more sub-combinations being separated from other components of the kit. The sub-combinations can be combinable to create a reaction mixture set forth herein (or combined to perform a reaction set forth herein). In particular embodiments, a sub-combination of components that is present in an individual vessel or package is insufficient to perform a reaction set forth herein.

However, the kit as a whole can include a collection of vessels or packages the contents of which can be combined to perform a reaction set forth herein.

A kit can include a suitable packaging material to house the contents of the kit. The packaging material can be constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of conjugating a cargo molecule to a linker moiety of an unnatural nucleobase in an oligonucleotide.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

In one embodiment, a kit provides one or more unnatural nucleobases or derivatives thereof and reagents configured for performing site-specific functionalization using the one or more unnatural nucleobases or derivatives thereof.

EXAMPLES

Currently, the free nucleosides and phosphoramidites of d5SICS and dNaM are commercially available from Berry and Associates (Dexter, MI).

Example 1. PCR-Based Screen to Identify Unnatural Base Pairs

The triphosphates of the α6 group were prepared from the previously reported nucleosides (Kubelka, T., Slavetinska, L., Eigner, V. and Hocek, M. Synthesis of 2,6-disubstituted pyridin-3-yl C-2'-deoxyribonucleosides through chemoselective transformations of bromo-chloropyridine C-nucleosides. Org. Biomol. Chem., 11, 4702-4718) according to Ludwig, J. and Eckstein, F. Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one. J. Org. Chem., 54, 631-635. The purity of all other triphosphates was confirmed by MALDI-TOF and UV-VIS. Taq and OneTaq DNA polymerases were purchased from New England Biolabs (Ipswich, MA). A mixture of dNTPs was purchased from Fermentas (Glen Burnie, MD). SYBR Green I Nucleic Acid Gel Stain (10, 000×) was purchased from Life Technologies (Carlsbad, CA). The synthesis of the DNA templates, D8 (Malyshev, D. A., Dhami, K., Quach, H. T., Lavergne, T., Ordoukhanian, P., Torkamani, A. and Romesberg, F. E. Efficient and sequence-independent replication of DNA containing a third base pair establishes a functional six-letter genetic alphabet. Proc. Natl. Acad. Sci. USA, 109, 12005-12010), used for screening rounds 1-5, and D6 (Malyshev, D. A., Seo, Y. J., Ordoukhanian, P. and Romesberg, F. E. PCR with an expanded genetic alphabet. J. Am. Chem. Soc., 131, 14620-14621), used for all other amplifications, was described previously. Sanger sequencing was carried out as described previously (Malyshev, D. A., Dhami, K., Quach, H. T., Lavergne, T., Ordoukhanian, P., Torkamani, A. and Romesberg, F. E. Efficient and sequence-independent replication of DNA containing a third base pair establishes a functional six-letter genetic alphabet. Proc. Natl. Acad. Sci. USA, 109, 12005-12010). Raw Sanger sequencing traces were used to determine the percent retention of the unnatural base pairs, which was converted to fidelity per doubling, as described (Malyshev, D. A., Dhami, K., Quach, H. T., Lavergne, T., Ordoukhanian, P., Torkamani, A. and Romesberg, F. E. Efficient and sequence-independent replication of DNA containing a third base pair establishes a functional six-letter genetic alphabet. Proc. Natl. Acad. Sci. USA, 109, 12005-12010; Malyshev, D. A., Seo, Y. J., Ordoukhanian, P. and Romesberg, F. E. PCR with an expanded genetic alphabet. J. Am. Chem. Soc., 131, 14620-14621).

All PCR amplifications were performed in a CFX Connect Real-Time PCR Detection System (Bio-Rad), in a total volume of 25 µL using the following conditions: 1× OneTaq reaction buffer, 0.5× Sybr Green I, MgSO4 adjusted to 4.0 mM, 0.2 mM of each dNTP, 50 µM of each unnatural triphosphate, 1 mM of Primer1 and Primer2 (See Table 2), and 0.02 U/μl of the DNA polymerase. Other conditions specific for each round of screening are described in Table 3. Amplified products were purified using DNA Clean and Concentrator-5 spin columns from Zymo Research (Irvine, CA). After purification, the PCR products were sequenced on a 3730 DNA Analyzer (Applied Biosystems) to determine the retention of the unnatural base pair as described below. Fidelity was characterized from unnatural base pair (UBP) retention as determined by sequencing with Primer1 on a 3730 DNA Analyzer (Applied Biosystems).

TABLE 2

DNA sequences.

| Name | Sequence (5' to 3') | Remarks |
|---|---|---|
| Primer1 | CACACAGGAAACAGCTATGAC (SEQ ID NO: 1) | Primers for PCR |
| Primer2 | GAAATTAATACGACTCACTATAGG (SEQ ID NO: 2) | |
| Primer1-poly-dT | TTTTTTTTTTTTTTTTTTTTTTTT TTTTTTTTTTTTTTTTTTTTTTTT TTTTTTCACACAGGAAACAGCTATGAC (SEQ ID NO: 3) | Primers for Sanger sequencing |
| Primer2-poly-dT | TTTTTTTTTTTTTTTTTTTTTTTT TTTTTTTTTTTTTTTTTTTTTTTT TTTTTTTT GAAATTAATACGACTCACTATAGG (SEQ ID NO: 4) | |
| D8 | CACACAGGAAACAGCTATGACCCGGGT TATTACATGCGCTAGCACTTGGAATTC ACAATACT NaM TCTTTAAGGAAACC ATAGTAAATCTCCTTCTTAAAGTTAA GCTTAAC CCTATAGTGAGTCGTATTAATTTC (SEQ ID NO: 5) | |
| D6 | CACACAGGAAACAGCTATGACCCGGGT TATTACATGCGCTAGCACTTGGAATTC ACCAGACGNNN NaM NNNCGGGACCC ATAGTAAATCTCCTTCTTAAAGTTAAG CTTAAC CCTATAGTGAGTCGTATTAATTTC (SEQ ID NO: 6) | N = randomized natural nucleotide | agarose gels, followed by single band excision and subsequent clean up using the Zymo Research Zymoclean Gel DNA Recovery Kit. After elution with 20 μl of water, the DNA concentration was measured using fluorescent dye binding (Quant-iT dsDNA HS Assay kit, Life Technologies), and purified amplicons were sequenced in triplicate with both Primer1 and Primer2 to determine UBP retention and thus amplification fidelity. Amplification of DNA containing the pairs involving analogs of group α6 was performed with OneTaq polymerase under the following thermal cycling conditions: initial denaturation at 96° C. for 1 min; 16 cycles of 96° C. for 10 s, 60° C. for 15 s, 68° C. for 1 min. Fidelity was determined by sequencing amplicons in the Primer1 direction in triplicate. Amplification of DNA containing the UBPs formed between dTPT3 and d2MN or dDM2 was performed using OneTaq or Taq polymerases for 16 cycles under the following thermal cycling conditions: 1) OneTaq: initial denaturation at 96° C. for 1 min, 96° C. for 10 s, 60° C. for 15 s, 68° C. for 1 min; or 2) Taq: initial denaturation at 96° C. for 1 min, 96° C. for 5 s, 60° C. for 5 s, 68° C. for 10 s. Fidelity was determined by sequencing amplicons in the Primer1 direction in triplicate.

Figure 8:
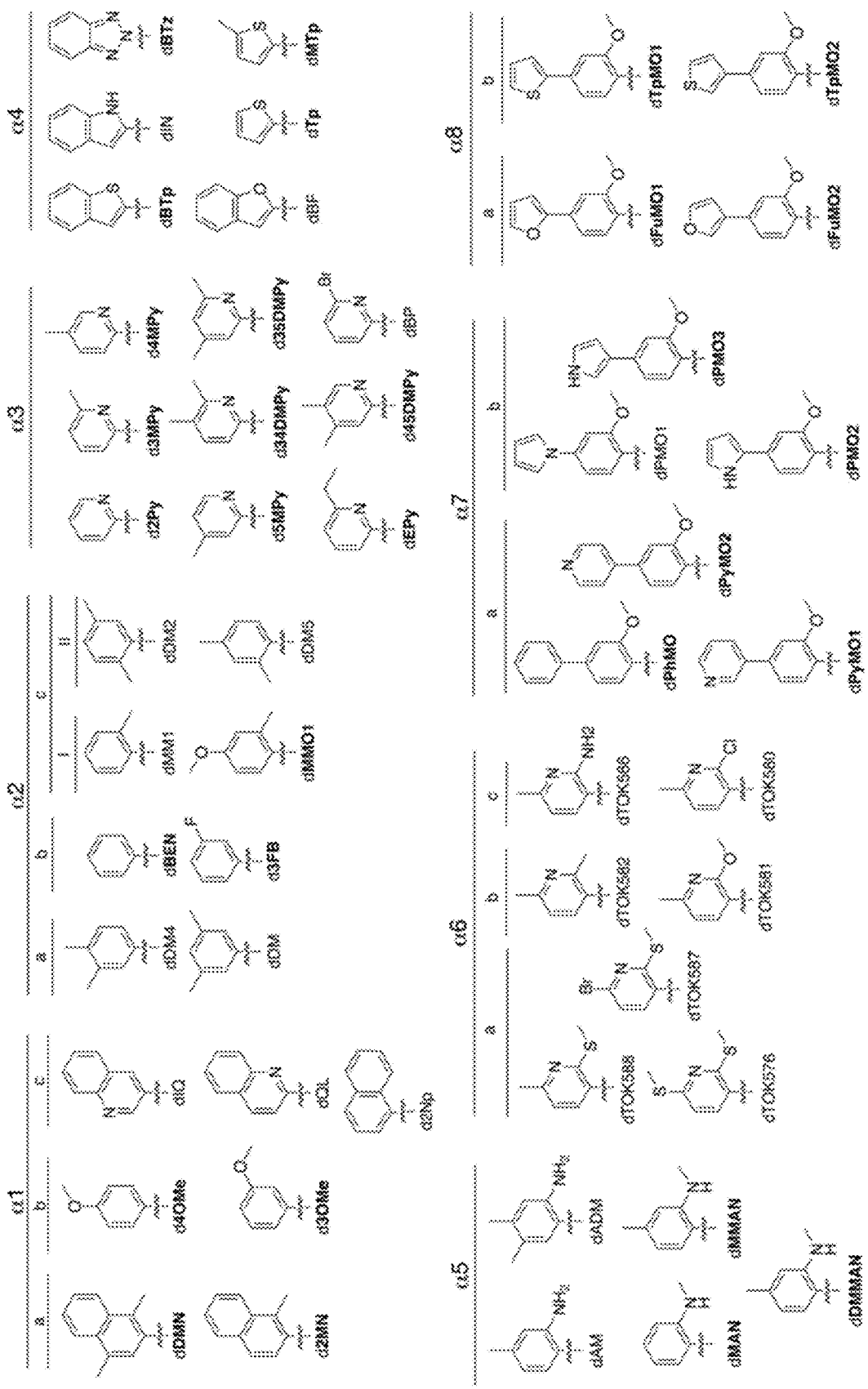
FIG. 8 illustrates 12 groupings of α nucleobase analogs, α1-α12.
Figure 8:
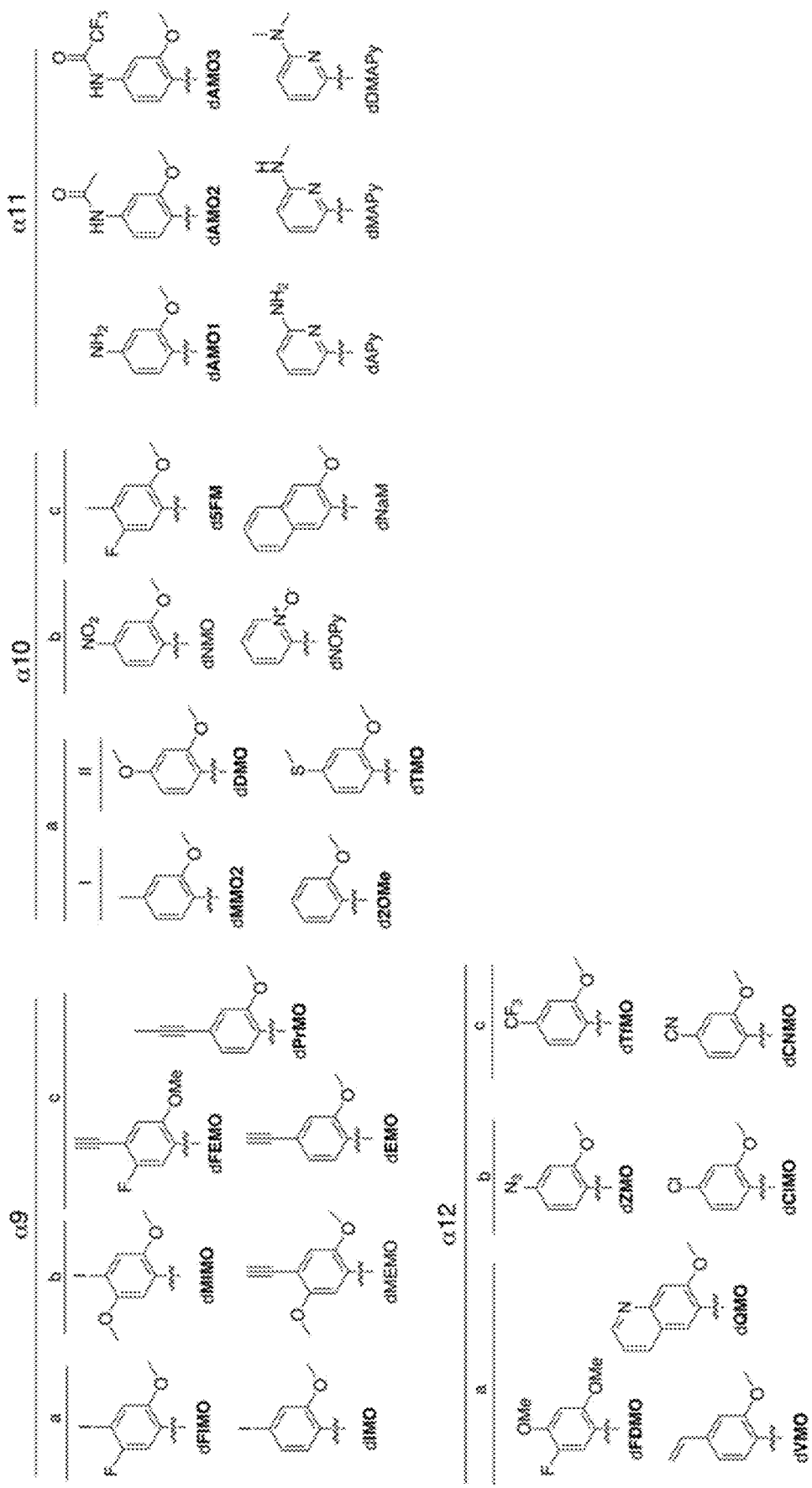

Results. To screen for well replicated UBPs, unnatural deoxynucleoside triphosphates were grouped for analysis into either dMMO2/dNaM- or d5SICS/dTPT3-like analogs, although the distinction is not completely clear in all cases. In total, 80 dMMO2/dNaM analogs were grouped into twelve "α groups" (α1-α12; FIG. 8), and 31 d5SICS/dTPT3 analogs were grouped into six "β groups" (β1-β6; FIG. 9). Note that the group designations used here should not be confused with anomer designation (all analogs examined are β glycosides). In addition, to increase the structure-activity relationship (SAR) content of the screen, seven previously reported nucleoside analogs (dTOK576—dTOK588) with substituted pyridyl nucleobases (Kubelka, T., Slavetinska, L., Eigner, V. and Hocekm M. Synthesis of 2,6-disubstituted pyridin-3-yl C-2'-deoxyribonucleosides through chemoselective transformations of bromo-chloropyridine C-nucleosides. *Org. Biomol. Chem.*, 11, 4702-4718) were phosphorylated and included as group α6. For screening, a 134-mer single-stranded DNA template containing a centrally located dNaM (referred to as D8) was PCR amplified in the presence of the natural triphosphates (200 μM each), all pairwise

TABLE 3

PCR conditions for each consecutive round of the PCR screen.

| Reaction Components | Rounds 1-4 | Round 5 | Round 6 | Final PCR characterization | |
|---|---|---|---|---|---|
| Buffer | 1× OneTaq | 1× OneTaq | 1× OneTaq | 1× OneTaq | 1× OneTaq |
| Enzyme | OneTaq | Taq | OneTaq or Taq | Taq | OneTaq |
| Template | D8$^a$ (0.1 ng) | D8$^a$ (0.1 ng) | D6$^a$ (0.01 ng) | D6$^a$ (0.01 ng) | D6$^a$ (0.01 ng) |
| | | | Thermal conditions | | |
| Initial denaturing | 96° C., 60 s | 96° C., 60 s | 96° C., 60 s | 96° C., 60 s | 96° C., 60 s |
| Denaturing | 96° C., 10 s | 96° C., 10 s | 96° C., 5 s | 96° C., 5 s | 96° C., 10 s |
| Annealing | 60° C., 15 s | 60° C., 15 s | 60° C., 5 s | 60° C., 5 s | 60° C., 5 s |
| Extension | 68° C., 60 s | 68° C., 60 s | 68° C., 10 s | 68° C., 10 s | 68° C., 30 s |
| # of cycles | 16 | 16 | 24 | 16 + 16 + 20 $^b$ | 16 + 16 + 20 $^b$ |

$^a$See Table 2 for sequences of the templates and primers.
$^b$ Initial amount of template was 0.01 ng. PCR mixture was amplified over 16 cycles, diluted 40,000-fold and amplified over another 16 cycles. The dilution/amplification step was repeated resulting in 52 total cycles of amplification.

Figure 14:
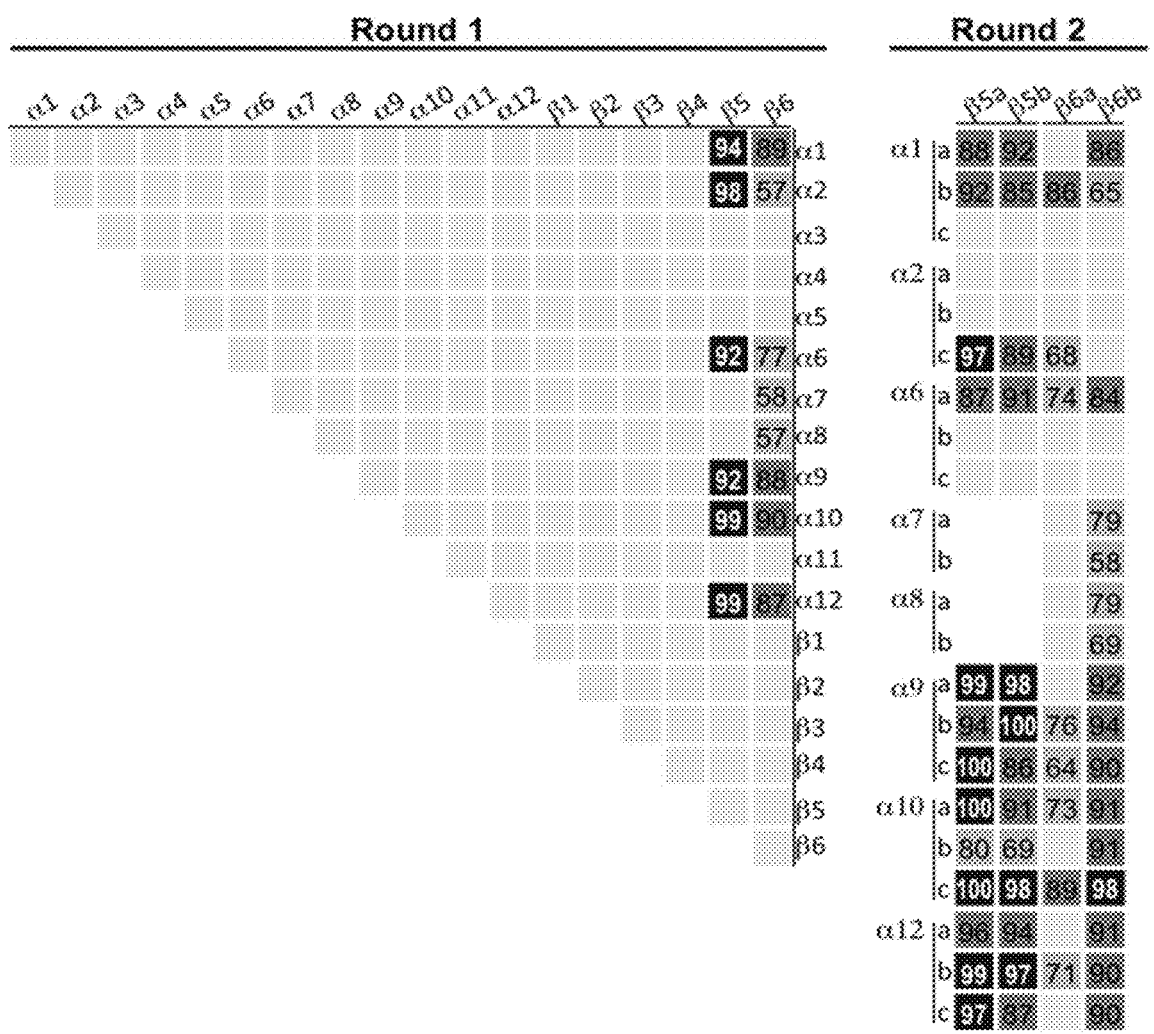
FIG. 14 shows percentages of unnatural base pairs retained in DNA after amplification during 6 rounds of screenings.
Figure 15:
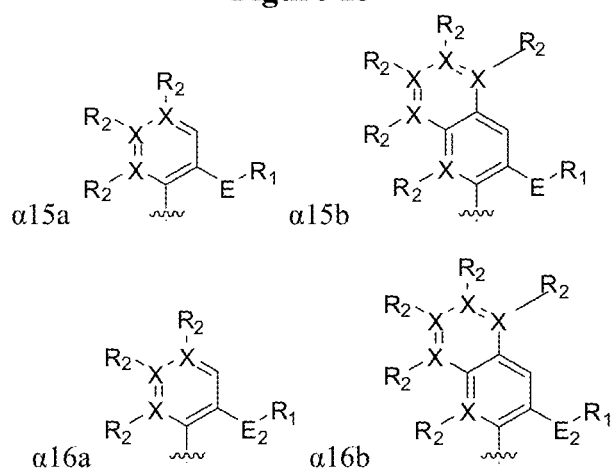
FIG. 15 illustrates a nucleobase analogs, α15a, α15b, α16a, and α16b; wherein each X is independently carbon or nitrogen; wherein each R1 is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each R2 is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently oxygen, sulfur or selenium; and wherein each E2 is independently sulfur or selenium.
Figure 16:
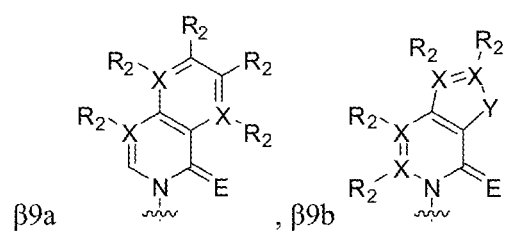
FIG. 16 illustrates β nucleobase analogs, β9a and β9b; and wherein each X is independently carbon or nitrogen; wherein each R1 is independently hydrogen, alkyl group, a reactive linker comprising a reactive center adapted to bond to a cargo reagent comprising a cargo and a group of reactivity complementary to the reactive center, or a coupled linker to which a cargo is bonded; wherein each R2 is optional and when present is independently hydrogen, alkyl, alkenyl, alkynyl, methoxy, methanethiol, methaneseleno, halogen, cyano, azide, nitro group, a reactive linker comprising a reactive center adapted to bond to a cargo reagent comprising a cargo and a group of reactivity complementary to the reactive center, or a coupled linker to which a cargo is bonded; wherein each Y is independently sulfur, oxygen, selenium, or secondary amine; wherein each E is independently oxygen, sulfur or selenium.

Specific PCR assay conditions. PCR with the most promising UBPs was carried out with the conditions as described in Table 3. PCR products were further purified on 2% combinations of an α and a β triphosphate group shown in FIGS. 8 and 9 (50 μM each), and 0.02 U/μL DNA polymerase. During the first round of PCR, dNaM templates the incorporation of an α analog and is then replaced by a β analog when the original strand is copied in the second round, with the resulting UBP amplified in subsequent rounds. The amplification product of each reaction was analyzed by Sanger sequencing. The presence of an unnatural nucleotide results in the abrupt termination of the sequencing chromatogram, allowing the level of UBP retention to be quantified by the amount of read through. The percentage of UBP retained in the DNA after amplification during each round of screening is shown in FIG. 14.

The first round of screening employed 0.1 ng of template and 16 cycles of amplification under relatively permissive conditions that included OneTaq polymerase and a 1 min extension time. For this example, OneTaq is considered permissive because it is a mixture of Taq (a family A polymerase) and Deep Vent (a family B polymerase), with the latter possessing exonucleotidic proofreading that allows for the excision of an incorrectly incorporated triphosphate. Under these conditions, only the pairs involving group β5 or β6 showed high retention.

The combinations of β5 or β6 and the α groups that showed the highest retention were progressed to a second round of screening, wherein they were divided into smaller groups (denoted by a, b, or c; FIGS. 8 and 9). High retention (≥97%) was observed with β5a and α2c, α9a, α9c, α10a, α10c, α12b, or α12c; with β5b and α9a, α9b, α10c, or α12b; and with β6b and α10c. Moderate retention (84-96%) was observed with β5a and α1a, α1b, α6a, α9b, α10b, or α12a; β5b and α1a, α1b, α2c, α6a, α9c, α10a, α12a, or α12c; β6a and α1b or α10c; and β6b and α1a, α6a, α9a-c, α10a, α10b, or α12a-c.

For a third round of screening, α analogs were analyzed in groups of only one to three compounds, and group β6a was subdivided into its two constituent triphosphates, dTPT1TP and dFPT1TP. The highest retention (≥90%) was observed with β5a and α1a, α2cII, α9a-c, α10aI, α10aII, α10c, α12b, or dTfMOTP; β5b and α9a, α9c, or α10c; dFPT1TP and α10aI; and β6b and α1a, α9a-c, α10aI, α10aII, α10c, α12b, dNMOTP, dTfMOTP, or dCNMOTP. Only slightly less retention (80-89%) was seen with β5a and α2cI, α12a, dNMOTP, dQMOTP, or dTOK587TP; β5b and α1a, α2cII, α10aI, α10aII, α12b, or dTOK587TP; dFPT1TP and α10c; and β6b and α12a, dQMOTP, dFuMO1TP, or dTOK587TP.

For a fourth round of screening, all of the α derivatives from FIG. 9 were analyzed as individual triphosphates, with the exception of α9b and α9c, which remained grouped. The highest retention (≥91%) was observed with β5a and α9b, α9c, dFIMOTP, dIMOTP, dFEMOTP, dMMO2TP, d2OMeTP, dDMOTP, d5FMTP, dNaMTP, dVMOTP, dZMOTP, dClMOTP, dTfMOTP, dQMOTP, d2MNTP, dDM2TP, or dTOK587TP; β5b and α9b, α9c, dFIMOTP, dIMOTP, dFEMOTP, dNaMTP, dZMOTP, dClMOTP, dQMOTP, dMM1TP, dDM2TP, or dTOK587TP; β6 analog dFPT1TP and α analogs d2OMeTP or dNaMTP; and β6b and α9b, α9c, dFIMOTP, dIMOTP, dFEMOTP, dMMO2TP, dDMOTP, dTMOTP, dNMOTP, d5FMTP, dNaMTP, dVMOTP, dZMOTP, dClMOTP, dTfMOTP, dQMOTP, dCNMOTP, d2MNTP, dTOK587TP, or dFuMO2TP.

To increase the stringency of the screen, a fifth round was performed with Taq polymerase instead of OneTaq, as it lacks exonuclease proofreading activity and thus increases the sensitivity to mispair synthesis. This round also separated all remaining α and β groups into individual triphosphates. The highest retention (≥90%) was seen with dSICSTP and dNaMTP; dSNICSTP and dNaMTP; dTPT2TP and dFDMOTP; dTPT3TP and dFIMOTP, dIMOTP, dNaMTP; and dFTPT3TP and dFIMOTP, dIMOTP, dFEMOTP, dNMOTP, dNaMTP, dClMOTP, dTfMOTP, or dCNMOTP.

To better differentiate between the UBPs, we progressed the sixty-two most promising candidate UBPs to a sixth round of screening in which the template concentration was decreased 10-fold (to 10 pg) to allow for greater amplification, and thereby afford greater discrimination, and the template was changed to D6 (Malyshev, D. A., Seo, Y. J., Ordoukhanian, P. and Romesberg, F. E. PCR with an expanded genetic alphabet. *J. Am. Chem. Soc.*, 131, 14620-14621), where the three flanking nucleotides on either side of the unnatural nucleotide are randomized among the natural nucleotides. Moreover, the denaturation and annealing steps were decreased to 5 s each, and the extension time was decreased to 10 s. Under these conditions, we explored amplification either with OneTaq or with Taq alone. The results with OneTaq showed the highest retention (>95%) with dSICSTP and dNaMTP; dSNICSTP and dFEMOTP; dTPT3TP and dFIMOTP, dIMOTP, dFEMOTP, dZMOTP, or dNaMTP; and dFTPT3TP and dIMOTP or dFEMOTP. Moderate retention (86%-94%) was observed with dSICSTP and dFEMOTP or dDM2TP; d5SICSTP and dNaMTP; dSNICSTP or dIMOTP; dTPT2TP and dNaMTP; dTPT3TP and dNMOTP, dClMOTP, dQMOTP, dCNMOTP or d2MNTP; and dFTPT3TP and dFIMOTP, dNaMTP, dZMOTP, dClMOTP, dTfMOTP, or dCNMOTP. While retention during Taq-mediated amplification was in general reduced relative to that with OneTaq, the general trends were similar. The highest retention (>96%) was observed with dTPT3TP and dFIMOTP or dIMOTP, and with dFTPT3TP and dFIMOTP. Only slightly lower retention (89%-94%) was observed with dTPT3TP and dFEMOTP, dNaMTP, or dCNMOTP; and dFTPT3TP and dIMOTP, dFEMOTP, dNaMTP, dClMOTP, dCNMOTP, or d2MNTP.

Amplification with the most promising combinations of triphosphates, dTPT3TP or dFTPT3TP and dFIMOTP, dIMOTP, dFEMOTP, or dNaMTP, was then performed over 52 cycles with Taq and a 10 s extension time, to explore particularly stringent conditions, or with OneTaq and a 30 s extension time, to explore more practical conditions (Table 4). Both amplified strands were sequenced in triplicate to determine UBP retention with high accuracy. With Taq, dTPT3-dNaM, dTPT3-dFIMO, dFTPT3-dNaM, and dFTPT3-dFIMO showed the highest retention, while the pairs involving dIMO and dFEMO showed somewhat less retention. With OneTaq, dTPT3-dNaM and dFTPT3-dNaM showed the highest retention, followed closely by dFTPT3-dFIMO and dTPT3-dFIMO.

TABLE 4

| dβTP | dαTP | Amplification, ×10$^{12}$ | Retention, % | Fidelity per Doubling, % |
|---|---|---|---|---|
| | | Taq, 10 s Extension | | |
| TPT3 | FIMO | 8.5 | 84 ± 3 | 99.60 ± 0.09 |
| | IMO | 6.3 | 81 ± 5 | 99.50 ± 0.15 |
| | FEMO | 5.0 | 79 ± 3 | 99.44 ± 0.09 |
| | NaM | 5.8 | 86.5 ± 0.5 | 99.66 ± 0.01 |
| FTPT3 | FIMO | 4.8 | 84 ± 3 | 99.60 ± 0.09 |
| | IMO | 5.6 | 82 ± 5 | 99.54 ± 0.13 |
| | FEMO | 5.7 | 81 ± 4 | 99.51 ± 0.11 |
| | NaM | 3.7 | 91 ± 6 | 99.76 ± 0.15 |
| 5SICS | NaM | 9.3 | <50[b] | <85[b] |

TABLE 4-continued

| dβTP | dαTP | Amplification, ×10$^{12}$ | Retention, % | Fidelity per Doubling, % |
|---|---|---|---|---|
| | | OneTaq, 1 min Extension | | |
| TPT3 | FIMO | 8.7 | 84.7 ± 1.1 | 99.61 ± 0.03 |
| | IMO | 9.4 | 82.9 ± 1.7 | 99.56 ± 0.05 |
| | FEMO | 10.4 | 82.2 ± 1.0 | 99.55 ± 0.03 |
| | NaM | 8.3 | 91.2 ± 1.3 | 99.79 ± 0.03 |
| FTPT3 | FIMO | 8.2 | 86 ± 3 | 99.65 ± 0.08 |
| | IMO | 7.1 | 76.8 ± 1.6 | 99.38 ± 0.05 |
| | FEMO | 6.3 | 72.4 ± 1.4 | 99.24 ± 0.04 |
| | NaM | 7.0 | 90 ± 2 | 99.76 ± 0.06 |
| 5SICS | NaM | 8.1 | 77.1 ± 0.7 | 99.00 ± 0.02 |

[a] Retention and fidelity determined as described in Example 1.
[b] UBP retention below 50%, and fidelity is thus estimated to be <85%.

The screening data suggest that several pairs formed between dTPT3 and the previously unexamined pyridine-based derivatives of α6 were reasonably well replicated. Thus, we examined in triplicate the amplification of DNA containing these UBPs using OneTaq and 16 amplification cycles with 1 min extension times (Table 5). The pairs formed between dTPT3 and dTOK580, dTOK582, or dTOK586 were poorly replicated. However, the pairs formed between dTPT3 and dTOK588, dTOK581, dTOK576, and dTOK587 were amplified with a retention of 62%, 65%, 85%, and 94%, respectively.

TABLE 5

Amplification and fidelity data of dTPT3 against pyridine-based derivatives from group α6; DM5, MMO2, DMO, and NaM were also characterized for scaffold comparison.

| dβTP | dαTP | Amplification | Retention, % | Fidelity, % |
|---|---|---|---|---|
| TPT3 | TOK576 | 780 | 85.20 ± 1.12 | 98.35 ± 0.14 |
| TPT3 | TOK580 | 1056 | <50 [b] | <85 [b] |
| TPT3 | TOK581 | 1034 | 65.07 ± 0.15 | 95.80 ± 0.02 |
| TPT3 | TOK582 | 1240 | <50 [b] | <85 [b] |
| TPT3 | TOK586 | 948 | <50 [b] | <85 [b] |
| TPT3 | TOK587 | 818 | 93.81 ± 1.35 | 99.34 ± 0.15 |
| TPT3 | TOK588 | 666 | 61.98 ± 7.09 | 94.99 ± 1.13 |
| TPT3 | DM5 | —[a] | —[a] | —[a] |
| TPT3 | MMO2 | 1096 | 90.95 ± 3.63 | 99.06 ± 0.40 |
| TPT3 | DMO | 864 | 84.02 ± 1.92 | 98.23 ± 0.23 |
| TPT3 | NaM | 1004 | 99.23 ± 1.12 | 99.92 ± 0.11 |

[a] No amplification was detected for this sample.
[b] Unnatural base pair retention was below 50% and fidelity is thus estimated less than 85%.

Finally, the screening data suggested that the pairs formed between dTPT3 and d2MN or dDM2 are reasonably well replicated, despite neither d2MN nor dDM2 possessing a putatively essential ortho H-bond acceptor. Thus, these pairs were further examined via 16 cycles of amplification with OneTaq or Taq alone, and with extension times of either 1 min or 10 s (Table 6). With Taq alone, only poor retention was observed. However, with OneTaq, retention was better for both pairs. Retention of the dTPT3-dDM2 pair is 58% and 69% with 1 min and 10 s extension times, respectively. Remarkably, dTPT3-d2MN is amplified with retentions of 96% and 94% with 1 min and 10 s extension times, respectively.

TABLE 6

Amplification and fidelity data of dTPT3 against either d2MN or dDM2, α analogs without an ortho H-bond acceptor.

| Enzyme | dβTP | dαTP | Extension Time | Amplification | Retention, % | Fidelity per Doubling, % |
|---|---|---|---|---|---|---|
| OneTaq | TPT3 | 2MN | 1 min | 880 | 95.54 ± 1.55 | 99.53 ± 0.17 |
| | | | 10 s | 224 | 93.53 ± 1.42 | 99.15 ± 0.20 |
| | TPT3 | DM2 | 1 min | 1420 | 57.92 ± 6.02 | 94.89 ± 0.94 |
| | | | 10 s | 376 | 68.46 ± 4.34 | 95.65 ± 0.72 |
| Taq | TPT3 | 2MN | 1 min | —[a] | — | — |
| | | | 10 s | —[a] | — | — |
| | TPT3 | DM2 | 1 min | 334 | <50 [b] | <85 [b] |
| | | | 10 s | 266 | <50 [b] | <85 [b] |

[a] No amplification was detected for these samples.
[b] Unnatural base pair retention was below 50% and fidelity is thus estimated less than 85%.

Discussion. A PCR-based screen to identify the most promising UBPs was performed herein. To increase the SAR content of the screen, seven novel α derivatives that are based on a pyridyl scaffold with different substituents at the positions ortho and para to the glycosidic linkage were included.

Structure-activity relationship data. Even under permissive conditions, where exonucleotidic proofreading activity was present and extension times were 1 min, only mixed groupings of α analogs with β analogs showed significant levels of retention, demonstrating that efficient replication requires the pairing of an α scaffold with a β scaffold. However, the only dβ groups that showed high retention were β5 and β6. This reveals the privileged status of the d5SICS/dTPT3-like scaffold relative to all of the others examined. The dominant contribution to the high retention with group β5 proved to result not from pairs involving d5SICS, but rather from pairs involving dSICS, and to a lesser extent dSNICS. For example, under all conditions, dSICS-dNaM was better replicated than d5SICS-dNaM. d5SICS resulted from the optimization of dSICS for pairing with dMMO2; apparently, the increased bulk of dNaM makes the added methyl group deleterious. Furthermore, dSNICS-dNaM is replicated nearly as well (with OneTaq) or better (with Taq) than d5SICS-dNaM, suggesting that a 6-aza substituent optimizes UBP synthesis by facilitating insertion of the unnatural triphosphate opposite dNaM or by increasing the efficiency with which the unnatural nucleotide templates the insertion of dNaMTP. Finally, dSNICS-dFEMO is also better replicated than d5SICS-dNaM, but only in the presence of proofreading, suggesting that while triphosphate insertion may be less efficient, increased efficiency of extension results in an overall increase in fidelity. The dominant contribution to high fidelity retention with group β6 was provided by dTPT3 and dFTPT3. In general, both paired well with dNaM, dFEMO, dFIMO, or dIMO. dTPT3 paired especially well with dFIMO and dIMO, suggesting that the para iodo substituent mediates favorable interactions, and it also paired well with dFEMO and especially dNaM when exonuclease activity was present. dFTPT3 paired well with either dIMO or dFEMO in the presence of exonuclease activity, as well as with dFIMO and dNaM in its absence.

While the nitrogen substituent of the pyridine-based α analogs (group α6) was generally detrimental for replication, a more detailed analysis of the UBPs formed with dTPT3 revealed several trends. A methyl, chloro, or amino substituent at the position ortho to the C-glycosidic linkage resulted in poorly replicated pairs, presumably due to poor extension after incorporation of the unnatural triphosphate. The ortho methoxy substituent of dTOK581 resulted in better replication, presumably due to its ability to both hydrophobically pack with the template during UBP synthesis and accept an H-bond with a polymerase-based H-bond donor during extension. The data also revealed that the methylsulfanyl ortho substituent of dTOK588, dTOK576, and especially dTOK587 results in better replication. This improvement is likely due to more optimized compromise between the ability to hydrophobically pack and the ability to accept an H-bond from the polymerase at the primer terminus. In addition, the para substituent in this series of derivatives can contribute to efficient replication, with a bromo substituent being the best, followed by a second methylsulfanyl group, and then finally a simple methyl group. When dTOK587, with its combination of the ortho methylsulfanyl and para bromo substituents, was paired with dTPT3, the resulting UBP was replicated by OneTaq and 1 min extension times with a fidelity (calculated from retention level) of 99.3%, which is slightly better than d5SICS-dMMO2 under similar conditions. Clearly, similar ortho methylsulfanyl and para bromo substituents should be examined with the more efficiently replicated a—like scaffolds, such as dFIMO and dNaM.

The replication of the pairs formed between dTPT3 and d2MN or dDM2 also merits discussion. DNA containing these pairs is not amplified by Taq alone, but is well amplified by OneTaq. This result was unexpected because neither d2MN nor dDM2 possesses the ortho H-bond acceptor that has been postulated to be essential for extension of the nascent (natural or unnatural) primer terminus. Specifically, when a nucleotide is positioned at the growing primer terminus, the H-bond acceptor is disposed into the developing minor groove where it accepts an H-bond from the polymerase, and this H-bond is thought to be required for proper terminus alignment. When amplified with OneTaq and a 1 min extension time, dTPT3-d2MN is replicated with a fidelity of 99.5%, which only drops to 99.1% when the extension time is reduced to 10 s. The absence of amplification in the absence of proofreading, coupled with the only small decrease observed in the presence of proofreading when extension times were reduced, implies that the surprisingly high fidelity amplification of DNA containing dTPT3-d2MN results from selective extension of the UBP relative to mispairs. This suggests that the absence of an ortho H-bond acceptor is more deleterious for the extension of a mispair than for the extension of the UBPs.

Efforts toward the expansion of the genetic alphabet. Overall, the data confirms that dTPT3-dNaM is the most promising UBP of those tested. However, the pairs formed between dTPT3 and dFEMO, dFIMO, or dIMO, or between dFTPT3 and dNaM, dFEMO, dFIMO, or dIMO, are also promising. In addition to the most promising UBPs noted above, it is noteworthy that a remarkable number of additional novel pairs are replicated with only a moderately reduced fidelity, or are replicated with a high fidelity when the amplification is performed under less stringent conditions (Table 7). Along with the most efficiently replicated UBPs, these pairs provide a wide range of scaffolds with diverse physicochemical properties for further optimization efforts, where different physicochemical properties are expected to bestow the constituent nucleotides with different pharmacokinetic-like properties.

TABLE 7

| dβTP | dαTP | Retention (%) |
|---|---|---|
| SICS | NaM | 99[a] |
| SICS | FEMO | 92[b] |
| SNICS | NaM | 90[a] |
| SNICS | FEMO | 95[b] |
| SNICS | IMO | 88[b] |
| TPT3 | NMO | 89[b] |
| TPT3 | ZMO | 86[b] |
| TPT3 | ClMO | 90[b] |
| TPT3 | QMO | 90[b] |
| TPT3 | CNMO | 91[b] |
| FTPT3 | NMO | 94[a] |
| FTPT3 | ZMO | 88[a] |
| FTPT3 | ClMO | 97[a] |
| FTPT3 | QMO | 87[a] |
| FTPT3 | CNMO | 94[a] |

[a]PCR Conditions: 100 pg D8 template amplified for 16 cycles with Taq polymerase under thermocycling conditions: initial denaturation at 96° C. for 1 min, 96° C. for 30 s, 60° C. for 15 s, 68° C. for 60 s.
[b]PCR Conditions: 10 pg D6 template amplified for 24 cycles with OneTaq polymerase under thermocycling conditions: initial denaturation at 96° C. for 1 min, 96° C. for 5 s, 60° C. for 5 s, 68° C. for 10 s.

Example 2. General Procedure for Triphosphate Synthesis

Proton sponge (1.3 equiv) and the free nucleoside derivative (1.0 equiv) were dissolved in dry trimethyl phosphate (40 equiv) and cooled to −15° C. under nitrogen atmosphere. Freshly distilled POCl3 (1.3 equiv) was added dropwise and the resulting mixture was stirred at −10° C. for 2 h. Tributylamine (6.0 equiv) and a solution of tributylammonium pyrophosphate (5.0 eq.) in dimethylformamide (0.5 M) were added. Over 30 min, the reaction was allowed to warm slowly to 0° C. and then was quenched by addition of 0.5 M aqueous Et3NH2CO3 (TEAB) pH 7.5 (2 vol-equiv.). The mixture was diluted two-fold with H2O and the product was isolated on a DEAE Sephadex column (GE Healthcare) with an elution gradient of 0 to 1.2 M TEAB, evaporated, and co-distilled with H2O (3×). Additional purification by reverse-phase (C18) HPLC (0-35% CH3CN in 0.1 M TEAB, pH 7.5) was performed, (10%-31% yield).

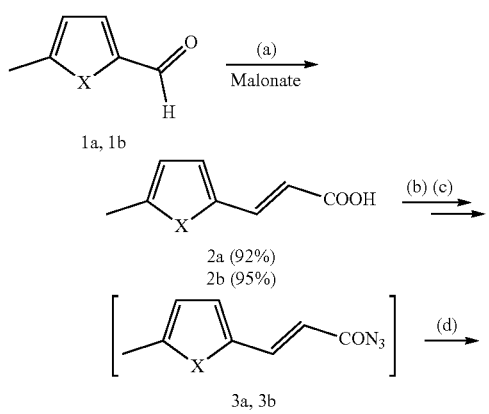

Scheme S1

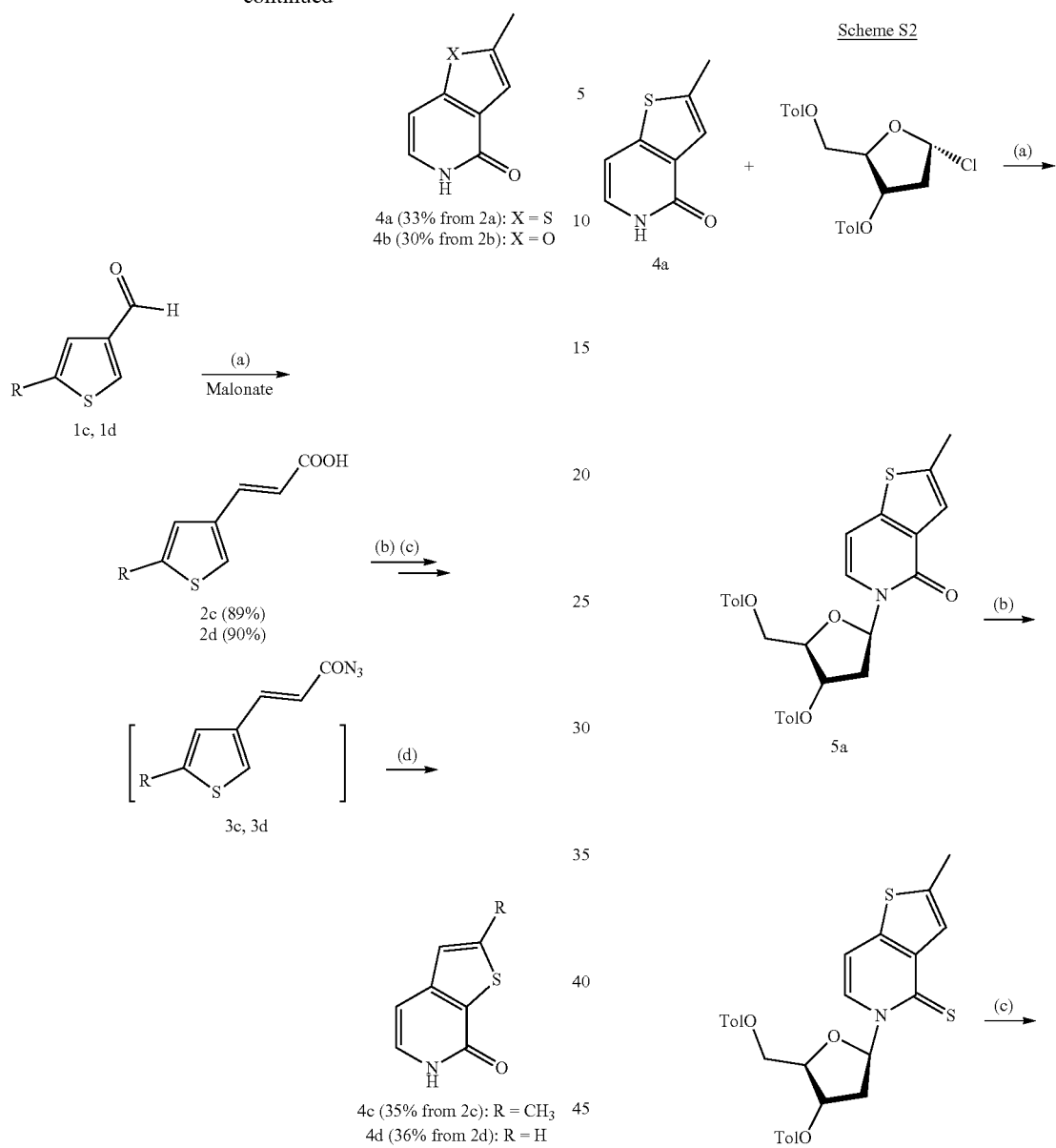

(a) Piperidine, Py, 100° C., 12 h, then reflux for 1 h; (b) SOCl2, DMF, CHCl3, reflux, 3 h, (c) NaN3, 1,4-dioxane, H2O, 5° C., 0.5 h; (d) diphenyl ether, 230° C., 1 h.

The nucleobase analogs 4a, 4b, 4c and 4d were synthesized based on literature methods1,2 as shown in Scheme 51. Briefly, condensation of the aldehyde (1a-d) with malonic acid at 100° C. in pyridine as a solvent and piperidine as a catalyst for 12 h, followed by a reflux for 1 h, yielded the corresponding acrylic acid intermediates (2a-d). Chlorination of these acids with thionyl chloride in chloroform in the presence of DMF afforded the acyl chlorides, which were not purified but could be used directly in the preparation of the azides (3a-d). Compounds 3a-d were prepared in a biphasic mixture of 1,4-dioxane and water at 5° C. with sodium azide. Crude mixtures of 3a-d in CHCl3 solutions were added portion-wise to diphenyl ether and heated to 230° C. to give the isocyanates that underwent subsequent intramolecular cyclization to the fused 6-5 bicyclic systems 4a-d.

-continued

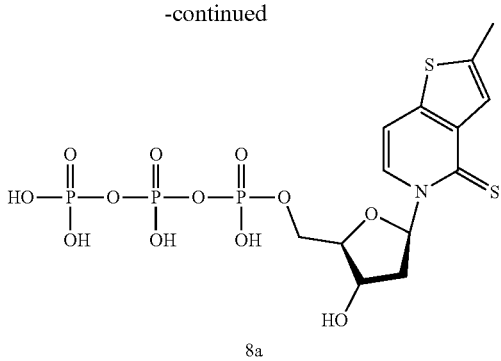

8a (a) N,O-bis(TMS)acetamide, SnCl4 (1M in CH2Cl2), CH2Cl2, 3 h, 45%;
(b) Lawesson's reagent, toluene, reflux, overnight, 58%; (c) 30% NaOMe, MeOH, rt, 1 h, 85%; (d) Proton sponge, POCl3, Bu3N, Bu3NPPi, (MeO)3P, DMF, -20° C., 31%.

Compound 5a. To a solution of 4a (54 mg, 0.33 mmol) in CH2Cl2 (8 mL) at room temperature under nitrogen atmosphere was added bis(trimethylsilyl)acetamide (83 mg, 0.39 mmol). After stirring for 40 min, 3,5-bis(toluoyl)-2-deoxyribosyl chloride (196 mg, 0.39 mmol) was added. The reaction mixture was cooled to 0° C. and SnCl4 was added dropwise (1.0 M in CH2Cl2, 160 µL, 0.16 mmol). The solution was stirred for 2 h at room temperature. The reaction mixture was diluted with EtOAc, quenched with saturated aqueous NaHCO3, extracted with EtOAc, dried, filtered and evaporated. The crude product was subjected to silica gel column chromatography (Hexane/EtOAc) to afford compound 5a as white foam (77 mg, 0.15 mmol, 45%). 1H NMR (500 MHz, CDCl3) δ 7.97-6.82 (m, 11H, Ar—H), 6.44 (d, J=7.5 Hz, 1H, H-1'), 5.63 (d, J=6.5 Hz, 1H, H-3'), 4.76-4.68 (m, 2H, H-5'a, 5'b), 4.59 (d, J=2.5 Hz, H-4'), 2.89 (dd, J=1.5, 0.5 Hz, 1H, H-2'a), 2.59 (s, 3H, Ar—CH3), 2.43 (s, 3H, Ar—CH3), 2.43 (s, 3H, Ar—CH3), 2.36-2.30 (m, 1H, H-2'b). 13C NMR (125 MHz, CDCl3) δ 166.6, 166.5, 158.5, 147.2, 144.8, 144.6, 140.0, 131.1, 130.3, 130.0, 129.9, 129.7, 127.1, 126.9, 125.6, 122.8, 102.7, 85.9, 83.3, 75.6, 64.8, 39.6, 22.1, 16.1. HRMS (ESI+) m/z calcd for C29H28NO6S (M+H+) 518.1632, found 518.1621.

Compound 6a. Compound 5a (27 mg, 0.052 mmol) was dried by 3 co-evaporations with anhydrous toluene. The residue was dissolved in anhydrous toluene (1 mL). Lawesson's reagent (41.5 mg, 0.10 mmol) was added and the mixture was heated overnight at reflux. After filtration on cotton, the filtrate was concentrated and the crude product was subjected to a silica gel column chromatography (Hexane/EtOAc) to afford compound 6a as a yellow foam (16 mg, 0.03 mmol, 58%). 1H NMR (500 MHz, CDCl3) δ 8.00-7.89 (m, 4H, Ar—H), 7.71 (m, 1H, Ar—H), 7.49-7.48 (m, 1H, H-1'), 7.29-7.21 (m, 4H, Ar—H), 7.65-7.62 (m, 1H, Ar—H), 6.90 (d, J=7.5 Hz, 1H, Ar—H), 5.64-5.62 (m, 1H, H-4'), 4.85-4.74 (m, 2H, H-5'a), 4.68-4.67 (m, 1H, H-5'b), 3.38-3.34 (m, 1H, H-3'), 2.26 (s, 3H), 2.44 (s, 3H), 2.41 (s, 3H), 2.28-2.22 (m, 1H). 13C NMR (125 MHz, CDCl3) δ 174.6, 166.6, 144.9, 144.8, 142.9, 142.7, 142.3, 130.3, 130.0, 129.7, 127.9, 127.0, 126.9, 126.8, 108.3, 100.0, 91.4, 84.0, 74.9, 64.5, 39.3, 22.2, 22.1, 16.3. HRMS (ESI+) m/z calcd for C29H28NO5S2 (M+H+) 534.1403, found 534.1404.

Compound 7a. To a solution of 6a (20 mg, 0.037 mmol) in methanol (1.0 mL) was added dropwise 30% NaOMe (8.66 mg, 0.16 mmol). The reaction mixture was stirred for 1 h at room temperature and monitored by TLC. The reaction mixture was then concentrated and the crude product was subjected to silica gel column chromatography (MeOH/CH2Cl2) to afford compound 7a as yellow foam (9.2 mg, 0.031 mmol, 85%). 1H NMR (500 MHz, CD3OD) δ 8.36 (d, J=4 Hz, 1H, Ar—H), 7.58 (d, J=1Hz, 1H, Ar—H), 7.35 (t, J=4 Hz, 1H, H-1'), 7.22 (d, J=8 Hz, 1H, Ar—H), 4.07-4.06 (m, 1H, H-4'), 4.07 (d, J=4 Hz, 1H, H-3'), 3.80 (dd, J=24, 4 Hz, 2H, H-5'a, b), 2.79-2.76 (m, 1H, H-2'a), 2.13-2.08 (m, 1H, H-2'b). 13C NMR (125 MHz, CD3OD) δ 173.60, 143.29, 142.26, 142.23, 129.35, 126.11, 108.01, 91.14, 88.44, 70.37, 61.35, 41.59, 14.81. HRMS (ESI+) m/z calcd for C13H16NO3S2 (M+H+) 298.0566, found 298.0569.

Compound 8a (dTPT1TP). Compound 8a (11.2 mg, 20.8 µmol, 31%) was synthesized using the General Procedure for Triphosphate Synthesis described above starting from 7a (20 mg, 67.3 µmol). 31P NMR (162 MHz, D2O) δ -10.3 (d, J=19.8 Hz, γ-P), -10.9 (d, J=20.1 Hz, α-P), -22.8 (t, J=19.4 Hz, β-P). MS (MALDI-TOF-, matrix: 9-aminoacridine) (m/z): [M-H]- calcd for C13H17NO12P3S2, 536.3, found, 536.7.

Scheme S3

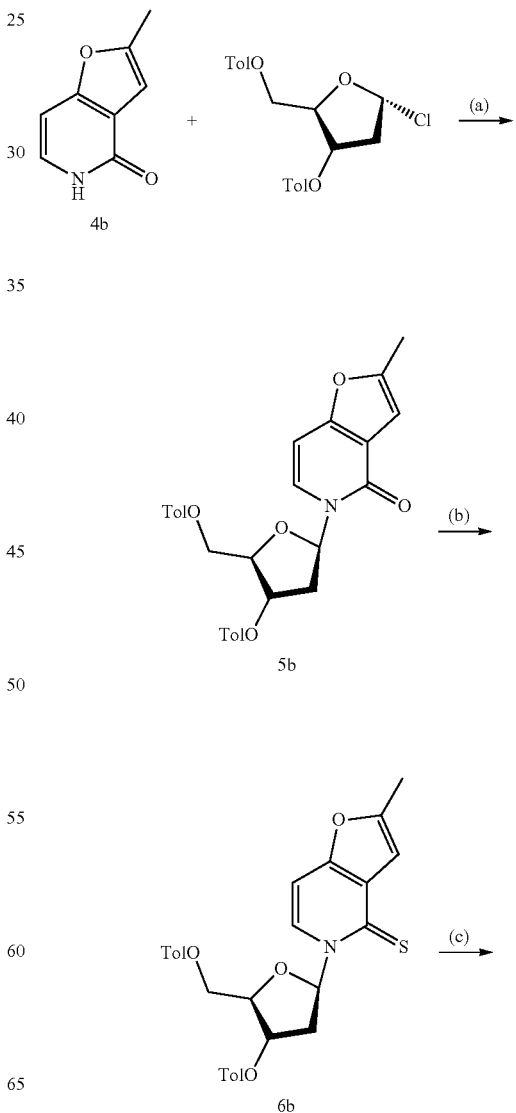

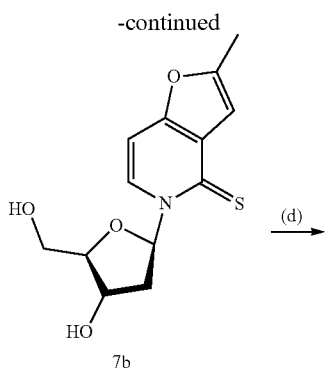

(a) N,O-bis(TMS)acetamide, SnCl4 (1M in CH2Cl2), CH2Cl2, 3 h, 41%;
(b) Lawesson's reagent, toluene, reflux, overnight, 52%; (c) 30% NaOMe, MeOH, rt, 1 h, 85%; (d) Proton sponge, POCl3, Bu3N, Bu3NPPi, (MeO)3P, DMF, -20° C., 21%.

Compound 5b. To a solution of 4b (100 mg, 0.67 mmol) in CH2Cl2 (8 mL) at room temperature under nitrogen atmosphere was added bis(trimethylsilyl)acetamide (165 mg, 0.81 mmol). After stirring for 40 min, 3,5-bis(toluoyl)-2-deoxyribosyl chloride (292 mg, 0.81 mmol) was added. The reaction mixture was cooled to 0° C. and SnCl4 was added dropwise (1.0 M in CH2Cl2, 200 µL, 0.2 mmol). The solution was stirred for 2 h at room temperature. The reaction mixture was diluted with EtOAc, quenched with saturated aqueous NaHCO3, extracted with EtOAc, dried, filtered and evaporated. The crude product was subjected to silica gel column chromatography (Hexane/EtOAc) to afford compound 5b as white foam (137 mg, 0.27 mmol, 41%). 1H NMR (500 MHz, CDCl3) δ 7.99 (d, J=8.1 Hz, 2H, Ar—H), 7.93 (d, J=8.1 Hz, 2H, Ar—H), 7.55 (d, J=7.7 Hz, 1H, Ar—H), 7.33-7.28 (m, 2H, Ar—H), 7.27-7.20 (m, 2H, Ar—H), 6.82 (dd, J=8.3, 5.6 Hz, 1H, Ar—H), 6.57 (d, J=0.9 Hz, 1H, Ar—H), 6.41 (d, J=7.7 Hz, 1H, H-1'), 5.68-5.61 (m, 1H, H-4'), 4.75 (dd, J=12.1, 3.4 Hz, 2H, H-5' a, b), 4.62 (q, J=3.1 Hz, 1H, H-3'), 2.94 (ddd, J=14.3, 5.6, 1.7 Hz, 1H, H-2'a), 2.48-2.39 (s, 3×3H, Ar—CH3), 2.36-2.26 (m, 1H, H-2'b). 13C NMR (125 MHz, CDCl3) δ 166.6, 166.5, 159.2, 159.1, 154.5, 144.8, 144.6, 130.2, 130.0, 129.7, 127.5, 127.1, 126.9, 117.5, 103.3, 96.6, 86.0, 83.2, 75.5, 64.7, 39.8, 22.1, 14.1. HRMS (ESI+) m/z calcd for C29H28NO7 (M+H+) 502.1860, found 502.1885.

Compound 6b. Compound 5b (29 mg, 0.056 mmol) was dried by 3 co-evaporations with anhydrous toluene. The residue was dissolved in anhydrous toluene (1 mL). Lawesson's reagent (41.5 mg, 0.10 mmol) was added and the mixture was heated overnight at reflux. After filtration on cotton, the filtrate was concentrated and the crude product was subjected to a silica gel column chromatography (Hexane/EtOAc) to afford compound 6b as a yellow foam (15 mg, 0.029 mmol, 52%). 1H NMR (500 MHz, CDCl3) δ 8.10-7.89 (m, 5H, Ar—H), 7.52-7.48 (m, 1H, H-1'),7.29-7.22 (m, 4H, Ar—H), 6.8 (d, J=1Hz, 1H, Ar—H), 6.73 (d, J=7.5 Hz, 1H, Ar—H), 5.65-5.62 (m, 1H, H-4'), 4.84-4.74 (m, 2H, H-5'a, b), 4.67-4.65 (m, 1H, H-3'), 3.36-3.32 (m, 1H, H-2'a), 2.44 (s, 3H, Ar—CH3), 2.43 (s, 3H, s, 3H, Ar—CH3), 2.41 (s, 3H, s, 3H, Ar—CH3), 2.27-2.21 (m, 1H, H-2'b). 13C NMR (125 MHz, CDCl3) δ 166.6, 156.9, 153.9, 144.8, 130.3, 130.0, 129.8, 129.7, 127.9, 106.4, 96.0, 83.9, 56.6, 39.5, 22.1, 12.6. HRMS (ESI+) m/z calcd for C29H28NO6S (M+H+) 518.1632, found 518.1638.

Compound 7b. To a solution of 6b (20 mg, 0.039 mmol) in methanol (1.0 mL) was added dropwise 30% NaOMe (8.66 mg, 0.16 mmol). The reaction mixture was stirred for 1 h at room temperature and monitored by TLC. The reaction mixture was then concentrated and the crude product was subjected to silica gel column chromatography (MeOH/CH2Cl2) to afford compound 7b as yellow foam (9.3 mg, 0.033 mmol, 85%). 1H NMR (500 MHz, CD3OD) δ 8.57 (d, J=5 Hz, 1H, Ar—H), 7.42 (t, J=4 Hz, 1H, H-1'), 7.13 (d, J=7.5 Hz, 1H, Ar—H), 6.80 (s, 1H, Ar—H), 4.50-4.47 (m, 1H, H-4'), 4.12 (d, J=3.5 Hz, 1H, H-3'), 3.95 (dd, J=30, 3 Hz, 2H, H-5'a, b), 2.81-2.77 (m, 1H, H-2'a), 2.50 (s, 3H, Ar—CH3), 2.18-2.14 (m, 1H, H-2'b). 13C NMR (125 MHz, CD3OD) δ 172.9, 157.2, 154.5, 132.7, 131.3, 105.4, 100.8, 90.9, 88.5, 70.3, 61.3, 41.8, 12.7. HRMS (ESI+) m/z calcd for C13H16NO4S (M+H+) 282.0795, found 282.0790.

Compound 8b (dFPT1TP). Compound 8b (3.7 mg, 7.1 µmol, 10%) was synthesized using the General Procedure for Triphosphate Synthesis described above starting from 7b (20 mg, 71.2 µmol). 31P NMR (162 MHz, D2O) δ −10.4 (d, J=20.0 Hz, γ-P), −10.9 (d, J=19.4 Hz, α-P), −22.8 (t, J=20.0 Hz, β-P). MS (MALDI-TOF-, matrix: 9-aminoacridine) (m/z): [M−H]− calcd for C13H17NO13P3S, 520.3, found, 520.1.

Scheme S4

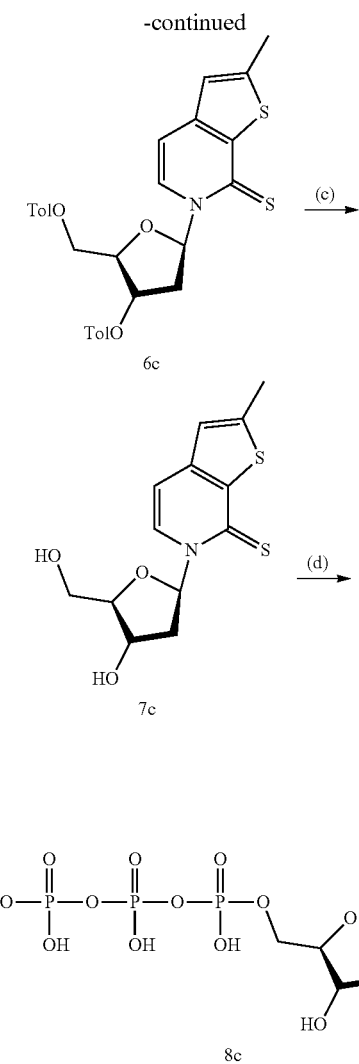

6c

7c

8c (a) N,O-bis(TMS)acetamide, SnCl4 (1M in CH2Cl2), CH2Cl2, 3 h, 40%;
(b) Lawesson's reagent, toluene, reflux, overnight, 31%; (c) 30% NaOMe, MeOH, rt,
1 h, 81%; (d) Proton sponge, POCl3, Bu3N, Bu3NPPi, (MeO)3P, DMF, -20° C., 15%.

Compound 5c. To a solution of 4c (46 mg, 0.28 mmol) in CH2Cl2 (8 mL) at room temperature under nitrogen atmosphere was added bis(trimethylsilyl)acetamide (66 mg, 0.33 mmol). After stirring for 40 min, 3,5-bis(toluoyl)-2-deoxyribosyl chloride (120 mg, 0.33 mmol) was added. The reaction mixture was cooled to 0° C. and SnCl4 was added dropwise (1.0 M in CH2Cl2, 140 µL, 0.14 mmol). The solution was stirred for 2 h at room temperature. The reaction mixture was diluted with EtOAc, quenched with saturated aqueous NaHCO3, extracted with EtOAc, dried, filtered and evaporated. The crude product was subjected to silica gel column chromatography (Hexane/EtOAc) to afford compound 5c as white foam (58 mg, 0.11 mmol, 40%). 1H NMR (500 MHz, CDCl3) δ 7.98-7.90 (m, 4H, Ar—H), 7.53 (d, J=7.4 Hz, 1H, Ar—H), 7.27-7.21 (m, 4H, Ar—H), 6.83-6.82 (m, 2H, Ar—H), 6.44 (d, J=7.5 Hz, 1H, H-1'), 5.63 (d, J=6.5 Hz, 1H, H-4'), 4.76-4.60 (m, 2H, H-5'a, b), 4.59 (d, J=2.5 Hz, 1H, H-3'), 2.89 (dd, J=13, 5.5 Hz, H-2'a), 2.59 (s, 3H, Ar—CH3), 2.43 (s, 3H, Ar—CH3), 2.40 (s, 3H, Ar—CH3), 2.37-2.30 (m, 1H, H-2'b). 13C NMR (125 MHz, CDCl3) δ 166.5, 158.0, 149.9, 146.3, 144.8, 144.6, 130.3, 130.0, 129.7, 128.8, 127.3, 122.8, 103.7, 100.0, 85.8, 83.2, 75.5, 64.8, 39.5, 22.1, 16.7. HRMS (ESI+) m/z calcd for C29H28NO6S (M+H+) 518.1632, found 518.1631.

Compound 6c. Compound 5c (50 mg, 0.097 mmol) was dried by 3 co-evaporations with anhydrous toluene. The residue was dissolved in anhydrous toluene (1.5 mL). Lawesson's reagent (83 mg, 0.20 mmol) was added and the mixture was heated overnight at reflux. After filtration on cotton, the filtrate was concentrated and the crude product was subjected to a silica gel column chromatography (Hexane/EtOAc) to afford compound 6c as a yellow foam (16 mg, 0.03 mmol, 31%). 1H NMR (500 MHz, CDCl3) δ 8.13-7.97 (m, 5H, Ar—H), 7.52-7.49 (m, 1H, H-1'), 7.37-7.29 (m, 4H, Ar—H), 6.99 (d, J=1Hz, 1H, Ar—H), 6.91 (d, J=7.5 Hz, 1H, Ar—H), 5.73-5.71 (m, 1H, H-4'), 4.91-4.82 (m, 2H, H-5'a, b), 4.76-4.74 (m, 1H, H-3'), 3.41-3.37 (m, 1H, H-2'a), 2.68 (s, 3H, Ar—CH3), 2.52 (s, 3H, Ar—CH3), 2.49 (s, 3H, Ar—CH3), 2.39-2.34 (m, 1H, H-2'b). 13C NMR (125 MHz, CDCl3) δ 172.1, 166.6, 154.0, 144.9, 144.7, 140.4, 130.3, 130.0, 129.7, 129.6, 127.0, 126.8, 122.7, 109.0, 91.2, 83.9, 75.0, 64.5, 39.4, 22.2, 22.1, 17.0. HRMS (ESI+) m/z calcd for C29H28NO5S2 (M+H+) 534.1403, found 534.1406.

Compound 7c. To a solution of 6c (20 mg, 0.037 mmol) in methanol (1.0 mL) was added dropwise 30% NaOMe (8.66 mg, 0.16 mmol). The reaction mixture was stirred for 1 h at room temperature and monitored by TLC. The reaction mixture was then concentrated and the crude product was subjected to silica gel column chromatography (MeOH/CH2Cl2) to afford compound 7c as yellow foam (8.9 mg, 0.03 mmol, 81%). 1H NMR (500 MHz, CD3OD) δ 8.48, (d, J=7.5 Hz, 1H, Ar—H), 7.42 (t, J=5 Hz, 1H, H-1'), 7.20 (d, J=5 Hz, 1H, Ar—H), 7.12 (s, 1H, Ar—H), 4.51-4.48 (m, 1H, H-4'), 4.13 (d, J=5 Hz, 1H, H-3'), 3.95 (dd, J=30, 5 Hz, 2H, H-5'a, b), 2.81-2.78 (m, 1H, H-2'a), 2.67 (s, 3H, Ar—CH3), 2.21-2.16 (m, 1H, H-2'b). 13C NMR (125 MHz, CD3OD) δ 171.1, 154.0, 144.1. 141.1, 131.1, 122.7, 108.8, 90.9, 88.5, 70.5, 61.4, 41.7, 15.4. HRMS (ESI+) m/z calcd for C13H16NO3S2 (M+H+) 298.0566, found 298.0566.

Compound 8c. Compound 8c (10.8 mg, 20.2 µmol, 30%) was synthesized using the General Procedure for Triphosphate Synthesis described above starting from 7c (20 mg, 67.3 µmol). 31P NMR (162 MHz, D2O) δ −10.8 (d, J=19.8 Hz, γ-P), −11.5 (d, J=20.1 Hz, α-P), −23.3 (t, J=20.1 Hz, β-P). MS (MALDI-TOF-, matrix: 9-aminoacridine) (m/z): [M−H]− calcd for C13H17NO12P3S2, 536.3, found, 536.1

Scheme S5

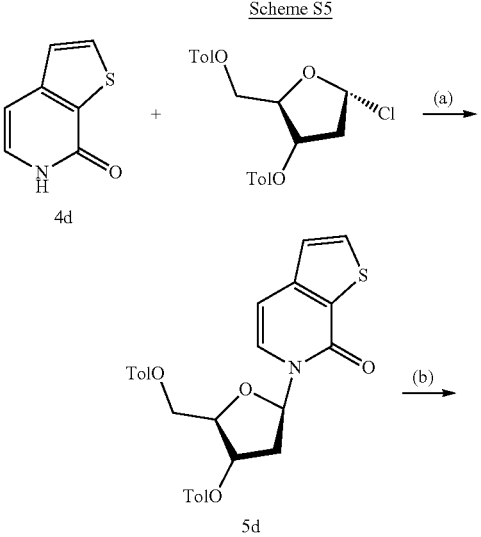

4d

5d

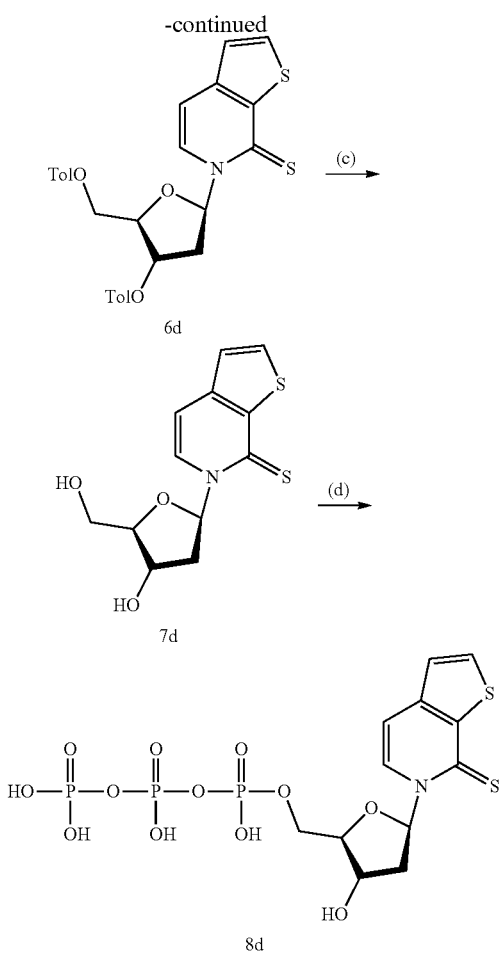

(a) N,O-bis(TMS)acetamide, SnCl4 (1M in CH2Cl2), CH2Cl2, 3 h, 39%;
(b) Lawesson's reagent, toluene, reflux, overnight, 33%; (c) 30% NaOMe, MeOH, rt, 1 h, 82%; (d) Proton sponge, POCl3, Bu3N, Bu3NPPi, (MeO)3P, DMF, -20° C., 30%.

Compound 5d. To a solution of 4d (200 mg, 1.32 mmol) in CH2Cl2 (8 mL) at room temperature under nitrogen atmosphere was added bis(trimethylsilyl)acetamide (298 mg, 1.46 mmol). After stirring for 40 min, 3,5-bis(toluoyl)-2-deoxyribosyl chloride (563 mg, 1.46 mmol) was added. The reaction mixture was cooled to 0° C. and SnCl4 was added dropwise (1.0 M in CH2Cl2, 660 μL, 0.66 mmol). The solution was stirred for 2 h at room temperature. The reaction mixture was diluted with EtOAc, quenched with saturated aqueous NaHCO3, extracted with EtOAc, dried, filtered and evaporated. The crude product was subjected to silica gel column chromatography (Hexane/EtOAc) to afford compound 5d as a white foam (260 mg, 0.52 mmol, 39%). 1H NMR (500 MHz, CDCl3) δ 7.98-7.90 (m, 4H, Ar—H), 7.70 (d, J=6 Hz, 1H, Ar—H), 7.55 (d, J=9.5 Hz, 1H, Ar—H), 7.28-7.16 (m, 5H, Ar—H), 6.84-6.85 (m, 1H, Ar—H), 6.57 (d, J=9.5 Hz, H-1'), 5.66-5.64 (m, 1H, H-4'), 4.75-4.72 (m, 2H, H-5'a, b), 4.61 (m, 1H, H-3'), 2.95-2.90 (m, 1H, H-2'a), 2.43 (s, 3H, Ar—CH3), 2.40 (s, 3H, Ar—CH3), 2.39-2.31 (m, 1H, H-2'b). 13C NMR (125 MHz, CDCl3) δ 166.2, 166.1, 158.1, 145.1, 144.4, 144.2, 133.8, 129.9, 129.6, 129.3, 129.1, 126.9, 126.5, 124.2, 103.5, 85.5, 82.9, 75.1, 64.4, 39.2, 21.7. HRMS (ESI+) m/z calcd for C20H20Cl2N2O5S (M+H+) 504.1475, found 504.1480.

Compound 6d. Compound 5d (50 mg, 0.1 mmol) was dried by 3 co-evaporations with anhydrous toluene. The residue was dissolved in anhydrous toluene (1 mL). Lawesson's reagent (48 mg, 0.12 mmol) was added and the mixture was heated overnight at reflux. After filtration on cotton, the filtrate was concentrated, and the crude product was subjected to a silica gel column chromatography (Hexane/EtOAc) to afford compound 6d as a yellow foam (17 mg, 0.033 mmol, 33%). 1H NMR (500 MHz, CDCl3) δ 8.14-7.82 (m, 7H, Ar—H), 7.51 (dd, J=7.5, 6.0 Hz, 1H, H-1'), 7.32-7.23 (m, 5H, Ar—H), 6.99 (d, J=7.2 Hz, 1H, Ar—H), 74-5.73 (m, 1H, H-4'), 4.92-4.83 (m, 2H, H-5'a, b), 4.78-4.77 (m, 1H, H-3'), 3.43-3.40 (m, 1H, H-2'a), 2.51 (s, 3H, Ar—CH3), 2.48 (s, 3H, Ar—CH3), 2.39-2.36 (m, 1H, H-2'b). 13C NMR (125 MHz, CDCl3) δ 173.5, 166.6, 144.9, 144.8, 139.5, 138.0, 134.5, 130.3, 130.0, 129.7, 129.5, 126.8, 124.7, 109.5, 91.4, 84.0, 75.0, 64.5, 39.4, 22.2, 22.1. HRMS (ESI+) m/z calcd for C28H26NO5S2 (M+H+) 520.1247, found 520.1241.

Compound 7d. To a solution of 6d (20 mg, 0.039 mmol) in methanol (1.0 mL) was added dropwise 30% NaOMe (8.66 mg, 0.16 mmol). The reaction mixture was stirred for 1 h at room temperature and monitored by TLC. The reaction mixture was then concentrated and the crude product was subjected to silica gel column chromatography (MeOH/CH2Cl2) to afford compound 7d as yellow foam (9.0 mg, 0.032 mmol, 82%). 1H NMR (500 MHz, CD3OD) δ 8.48 (d, J=5 Hz, 1H, Ar—H), 8.01 (d, J=5 Hz, 1H, Ar—H), 7.40-7.38 (m, 2H, Ar—H), 7.29 (d, J=10 Hz, 1H, H-1'), 4.47-4.46 (m, 1H, H-4'), 4.10 (m, 1H, H-3'), 3.94-3.88 (m, 2H, H-5'a, b), 2.77-2.76 (m, 1H, H-2'a), 2.19-2.14 (m, 1H, H-2'b). 13C NMR (125 MHz, CD3OD) δ 171.2, 144.7, 139.6, 137.6, 130.5, 124.2, 108.8, 90.7, 88.2, 70.1, 61.0, 41.3. HRMS (ESI+) m/z calcd for C12H14NO3S2 (M+H+) 284.041, found 284.0410.

Compound 8d (dTPT3TP). Compound 8d (5.7 mg, 10.9 μmol, 31%) was synthesized using the General Procedure for Triphosphate Synthesis described above starting from 7d (10 mg, 35.3 μmol). 31P NMR (162 MHz, D2O) δ -9.3 (d, J=19.5 Hz, γ-P), -10.8 (d, J=19.8 Hz, α-P), -22.4 (t, J=20.0 Hz, β-P). MS (MALDI-TOF-, matrix: 9-aminoacridine) (m/z): [M−H]− calcd for C12H15NO12P3S2−, 521.9, found, 521.9.

Scheme S6

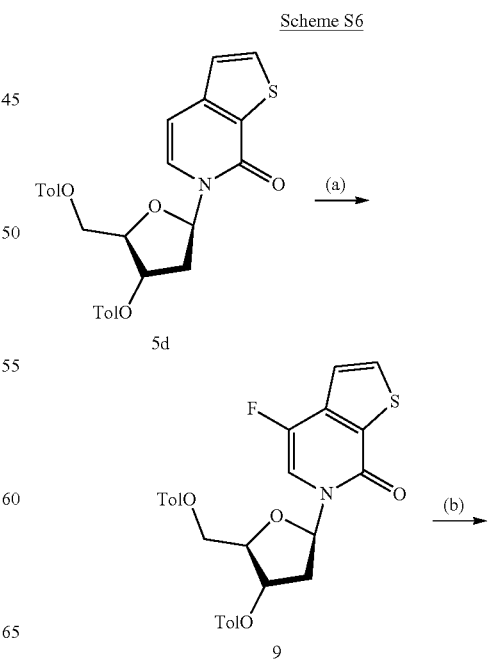

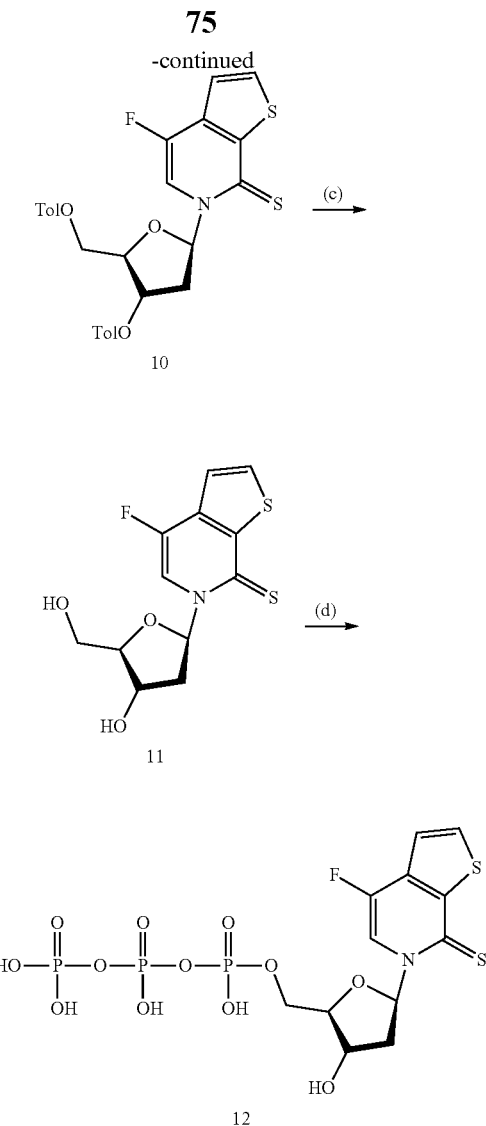

(a) i. Selectfluor, MeOH/CH3CN, reflux, 3 h: ii. TfOH-CH2Cl (1:1 v/v), 1 h, 85%;
(b) Lawesson's reagent, toluene, reflux, overnight, 32%; (c) 30% NaOMe, MeOH, rt, 1 h, 85%; (d) Proton sponge, POCl3, Bu3N, Bu3NPPi, (MeO)3P, DMF, -20° C., 10%.

Compound 9. Compound 5d (55 mg, 0.11 mmol) was dissolved in 1.0 mL MeOH—CH3CN (1:1 v/v), Selectfluor (42 mg, 0.12 mmol) was added and the mixture was heated at reflux for 3 h, then the solvent was evaporated, the residue was dissolved in EtOAc (20 mL), the organic phase was washed with water three times. Then the organic solvent was evaporated, and the solid residue was dried by 3 co-evaporations with anhydrous toluene. The residue was dissolved in 1 mL TfOH-CH2Cl2 (1:1 v/v) and the mixture was stirred at room temperature for 1 h, then the mixture was concentrated, and the crude product was subjected to a silica gel column chromatography (hexane/EtOAc) to afford compound 9 as a white solid (49 mg, 0.093 mmol, 85%). 1H NMR (500 MHz, CDCl3) δ 7.98-7.92 (m, 4H, Ar—H), 7.75 (d, J=5 Hz, 1H, Ar—H), 7.52 (d, J=7.5 Hz, 1H, Ar—H), 7.32-7.21 (m, 5H, Ar—H), 6.82-6.78 (m, 1H, H-1'), 5.64-5.61 (m, 1H, H-4'), 4.80-4.59 (m, 2H, H-5'a, b), 4.62-4.59 (m, 1H, H-3'), 2.93-2.87 (m, 1H, H-2'a), 2.43 (s, 3H, Ar—CH3), 2.39 (s, 3H, Ar—CH3), 2.34-2.27 (m, 1H, H-2'b). 13C NMR (125 MHz, CDCl3) δ 166.2, 166.1, 156.4, 144.5, 144.3, 137.7, 137.5, 134.6, 129.9, 129.6, 129.3, 126.6, 126.4, 120.2, 112.1, 111.7, 85.5, 83.1, 75.0, 64.2, 39.1, 21.8, 21.7. 19F NMR (376 MHz, CDCl3) δ -151.5. HRMS (ESI+) m/z calcd for C28H25FNO6S (M+H+) 522.1381, found 522.1380.

Compound 10. Compound 9 (20 mg, 0.038 mmol) was dried by 3 co-evaporations with anhydrous toluene. The residue was dissolved in anhydrous toluene (1 mL). Lawesson's reagent (18.5 mg, 0.046 mmol) was added and the mixture was heated overnight at reflux. After filtration on cotton, the filtrate was concentrated and the crude product was subjected to a silica gel column chromatography (Hexane/EtOAc) to afford compound 10 as a yellow foam (6.5 mg, 0.012 mmol, 32%). 1H NMR (500 MHz, CDCl3) δ 8.11-7.85 (m, 6H, Ar—H), 7.40-7.39 (m, 2H, Ar—H, H-1'), 7.28-7.21 (m, 4H, Ar—H), 5.64-5.63 (m, 1H, H-4'), 4.83 (m, 2H, H-5'a, b), 4.69 (m, 1H, H-3'), 3.34-3.29 (m, 1H, H-2'a), 2.44 (s, 1H, Ar—CH3), 2.40 (s, 3H, Ar—CH3), 2.30-2.26 (m, 1H, H-2'b). 13C NMR (125 MHz, CDCl3) δ 170.9, 166.6, 166.5, 144.9, 144.8, 138.6, 130.3, 130.0, 129.9, 129.7, 129.7, 126.9, 126.7, 120.5, 116.3, 116.0, 100.0, 91.6, 84.3, 74.7, 64.3, 39.2, 22.2, 22.1. 19F NMR (376 MHz, CDCl3) δ -142.9. HRMS (ESI+) m/z calcd for C28H25FNO5S2 (M+H+) 538.1153, found 538.1155.

Compound 11. To a solution of 10 (10 mg, 0.019 mmol) in methanol (1.5 mL) was added dropwise 30% NaOMe (4.33 mg, 0.08 mmol). The reaction mixture was stirred for 1 h at room temperature and monitored by TLC. The reaction mixture was then concentrated and the crude product was subjected to silica gel column chromatography (MeOH/CH2Cl2) to afford compound 11 as yellow foam (4.9 mg, 0.016 mmol, 85%). 1H NMR (500 MHz, CD3OD) δ 8.68 (d, J=5 Hz, 1H, Ar—H), 8.12 (d, J=5 Hz, 1H, Ar—H), 7.52 (d, J=5 Hz, 1H, Ar—H), 7.28 (t, J=6.5 Hz, 1H, H-1'), 4.48 (m, 1H, H-4'), 4.10 (m, 1H, H-3'), 3.94 (dd, J=35, 3 Hz, 2H, H-5'a, b), 2.78-2.75 (m, 1H, H-2'a), 2.24-2.19 (m, 1H, H-2'b). 13C NMR (125 MHz, CD3OD) δ 170.2, 150.2, 148.3, 139.0, 131.7, 131.6, 119.8, 117.8, 117.4, 91.5, 88.7, 70.1, 61.0, 41.5. 19F NMR (376 MHz, CD3OD) δ -145.3. HRMS (ESI+) m/z calcd for C12H13FNO3S2 (M+H+) 302.0315, found 302.0314.

Compound 12 (dFTPT3TP). Compound 12 (2.0 mg, 3.7 µmol, 22%) was synthesized using the General Procedure for Triphosphate Synthesis described above starting from 11 (5 mg, 16.6 µmol). 31P NMR (162 MHz, D2O) δ -10.9 (d, J=20.0 Hz, y-P), -11.6 (d, J=21.1 Hz, a-P), -23.3 (t, J=23.1 Hz, f3-P). 19F NMR (376 MHz, D2O) δ -138.5 (s). MS (MALDI-TOF-, matrix: 9-aminoacridine) (m/z): [M-H]- calcd for C12H14FNO12P3S2-, 539.9, found, 540.1.

Scheme S7

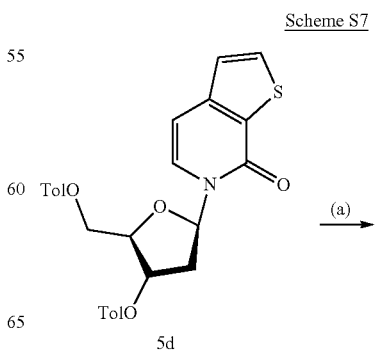

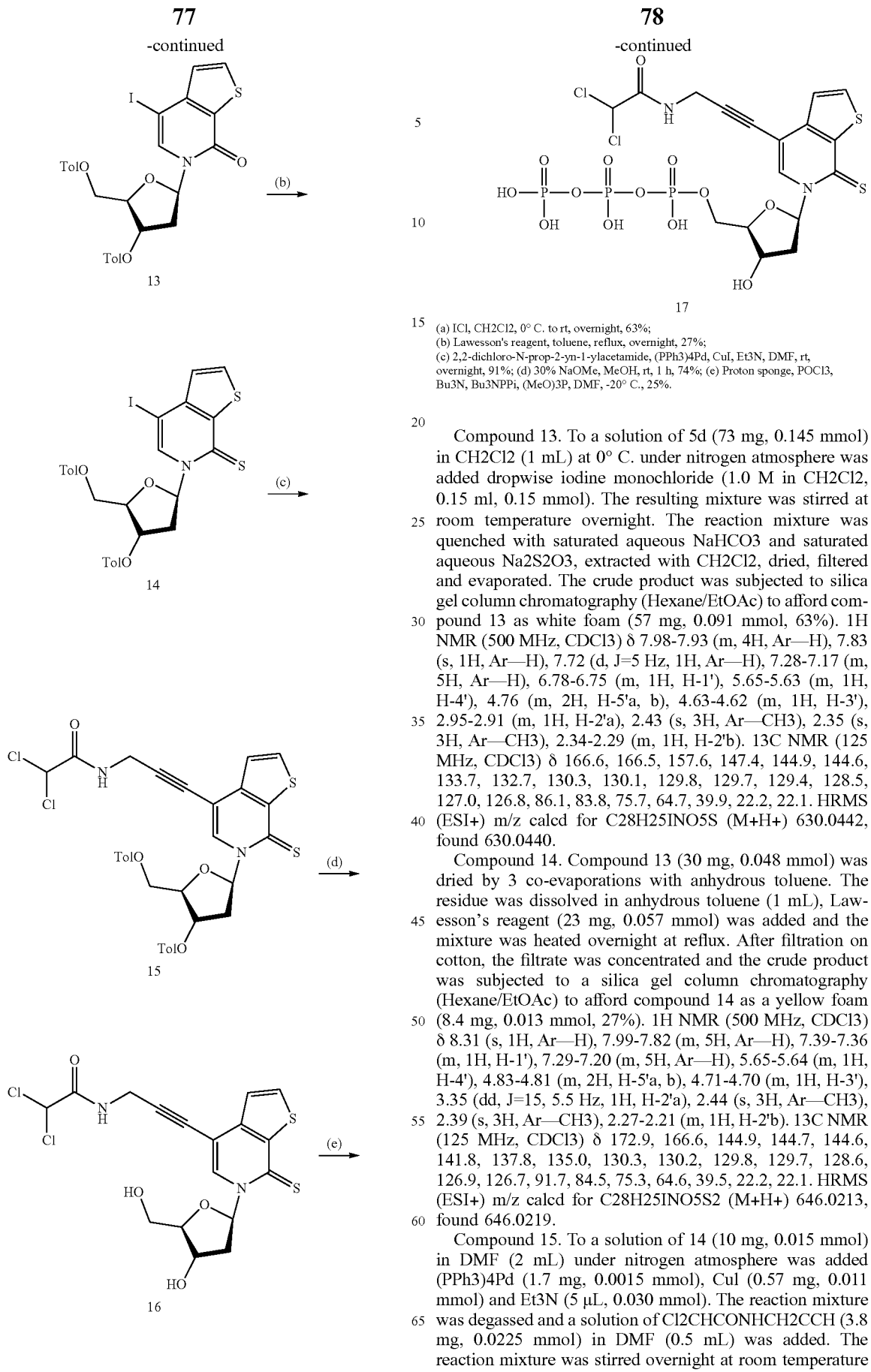

(a) ICl, CH2Cl2, 0° C. to rt, overnight, 63%;
(b) Lawesson's reagent, toluene, reflux, overnight, 27%;
(c) 2,2-dichloro-N-prop-2-yn-1-ylacetamide, (PPh3)4Pd, CuI, Et3N, DMF, rt, overnight, 91%; (d) 30% NaOMe, MeOH, rt, 1 h, 74%; (e) Proton sponge, POCl3, Bu3N, Bu3NPPi, (MeO)3P, DMF, -20° C., 25%.

Compound 13. To a solution of 5d (73 mg, 0.145 mmol) in CH2Cl2 (1 mL) at 0° C. under nitrogen atmosphere was added dropwise iodine monochloride (1.0 M in CH2Cl2, 0.15 ml, 0.15 mmol). The resulting mixture was stirred at room temperature overnight. The reaction mixture was quenched with saturated aqueous NaHCO3 and saturated aqueous Na2S2O3, extracted with CH2Cl2, dried, filtered and evaporated. The crude product was subjected to silica gel column chromatography (Hexane/EtOAc) to afford compound 13 as white foam (57 mg, 0.091 mmol, 63%). 1H NMR (500 MHz, CDCl3) δ 7.98-7.93 (m, 4H, Ar—H), 7.83 (s, 1H, Ar—H), 7.72 (d, J=5 Hz, 1H, Ar—H), 7.28-7.17 (m, 5H, Ar—H), 6.78-6.75 (m, 1H, H-1'), 5.65-5.63 (m, 1H, H-4'), 4.76 (m, 2H, H-5'a, b), 4.63-4.62 (m, 1H, H-3'), 2.95-2.91 (m, 1H, H-2'a), 2.43 (s, 3H, Ar—CH3), 2.35 (s, 3H, Ar—CH3), 2.34-2.29 (m, 1H, H-2'b). 13C NMR (125 MHz, CDCl3) δ 166.6, 166.5, 157.6, 147.4, 144.9, 144.6, 133.7, 132.7, 130.3, 130.1, 129.8, 129.7, 129.4, 128.5, 127.0, 126.8, 86.1, 83.8, 75.7, 64.7, 39.9, 22.2, 22.1. HRMS (ESI+) m/z calcd for C28H25INO5S (M+H+) 630.0442, found 630.0440.

Compound 14. Compound 13 (30 mg, 0.048 mmol) was dried by 3 co-evaporations with anhydrous toluene. The residue was dissolved in anhydrous toluene (1 mL), Lawesson's reagent (23 mg, 0.057 mmol) was added and the mixture was heated overnight at reflux. After filtration on cotton, the filtrate was concentrated and the crude product was subjected to a silica gel column chromatography (Hexane/EtOAc) to afford compound 14 as a yellow foam (8.4 mg, 0.013 mmol, 27%). 1H NMR (500 MHz, CDCl3) δ 8.31 (s, 1H, Ar—H), 7.99-7.82 (m, 5H, Ar—H), 7.39-7.36 (m, 1H, H-1'), 7.29-7.20 (m, 5H, Ar—H), 5.65-5.64 (m, 1H, H-4'), 4.83-4.81 (m, 2H, H-5'a, b), 4.71-4.70 (m, 1H, H-3'), 3.35 (dd, J=15, 5.5 Hz, 1H, H-2'a), 2.44 (s, 3H, Ar—CH3), 2.39 (s, 3H, Ar—CH3), 2.27-2.21 (m, 1H, H-2'b). 13C NMR (125 MHz, CDCl3) δ 172.9, 166.6, 144.9, 144.7, 144.6, 141.8, 137.8, 135.0, 130.3, 130.2, 129.8, 129.7, 128.6, 126.9, 126.7, 91.7, 84.5, 75.3, 64.6, 39.5, 22.2, 22.1. HRMS (ESI+) m/z calcd for C28H25INO5S2 (M+H+) 646.0213, found 646.0219.

Compound 15. To a solution of 14 (10 mg, 0.015 mmol) in DMF (2 mL) under nitrogen atmosphere was added (PPh3)4Pd (1.7 mg, 0.0015 mmol), CuI (0.57 mg, 0.011 mmol) and Et3N (5 μL, 0.030 mmol). The reaction mixture was degassed and a solution of Cl2CHCONHCH2CCH (3.8 mg, 0.0225 mmol) in DMF (0.5 mL) was added. The reaction mixture was stirred overnight at room temperature and monitored by TLC. The reaction mixture was diluted with EtOAc, quenched with saturated aqueous NaHCO3, extracted with EtOAc, dried, filtered and evaporated. The crude product was subjected to silica gel column chromatography (MeOH/CH2Cl2) to afford compound 15 as yellow foam (9.2 mg, 0.0135 mmol, 91%). 1H NMR (500 MHz, CDCl3) δ 8.26 (s, 1H, Ar—H), 7.99-7.82 (m, 5H, Ar—H), 7.40-7.37 (m, 2H, Ar—H, H-1'), 7.29-7.21 (m, 4H, Ar—H), 6.71 (br, 1H, NH), 6.95 (s, 1H, CHCl2), 5.65-5.64 (m, 1H, H-4'), 4.85-4.79 (m, 2H, H-5'a, b), 4.73 (m, 1H, H-3'), 4.26-4.11 (m, 2H, NHCH2), 3.38-3.34 (m, 1H, H-2'a), 2.44 (s, 3H, Ar—CH3), 2.40 (s, 3H, Ar—CH3), 2.31-2.25 (m, 1H, H-2'b). 13C NMR (125 MHz, CDCl3) δ 173.3, 166.6, 164.1, 144.8, 139.0, 138.3, 133.4, 130.3, 130.1, 129.8, 129.7, 126.9, 124.3, 104.8, 91.8, 88.3, 84.5, 78.8, 75.2, 66.4, 64.7, 39.6, 31.3, 22.2. 22.1. HRMS (ESI+) m/z calcd for C33H29Cl2N2O6S2 (M+H+) 683.0839, found 683.0854.

Compound 16. To a solution of 15 (9.2 mg, 0.0135 mmol) in methanol (1.0 ml) was added dropwise 30% NaOMe (2.92 mg, 0.32 mmol). The reaction mixture was stirred for 1 h at room temperature and monitored by TLC. The reaction mixture was concentrated and the crude product was subjected to silica gel column chromatography (MeOH/CH2Cl2) to afford compound 16 as yellow foam (4.5 mg, 0.01 mmol, 74%). 1H NMR (500 MHz, CD3OD) δ 8.69 (s, 1H, Ar—H), 8.06 (d, J=5 Hz, 1H, Ar—H), 7.53 (d, J=5 Hz, 1H, Ar—H), 7.30 (t, J=5 Hz, 1H, H-1'), 6.33 (s, 1H, CHCl2), 4.47-4.46 (m, 1H, H-4'), 4.36 (s, 2H, NHCH2), 4.11-4.08 (m, 1H, H-3'), 3.97 (dd, J=12, 3Hz, 2H, H-5'a, b), 2.79-2.74 (m, 1H, H-2'a), 2.21-2.16 (m, 1H, H-2'b). 13C NMR (125 MHz, CD3OD) δ 172.9, 138.4, 134.3, 123.9, 122.8, 104.7, 100.0, 91.2, 88.6, 77.1, 70.3, 66.4, 61.1, 41.7, 30.2. HRMS (ESI+) m/z calcd for C17H17Cl2N2O4S2 (M+H+) 447.0001, found 447.0020.

Compound 17 (dTPT3PATP). Compound 17 (2.2 mg, 3.1 μmol, 28%) was synthesized using the General Procedure for Triphosphate Synthesis described above starting from 16 (5 mg, 11.2 μmol). 31P NMR (162 MHz, D2O) δ −10.85 (d, J=19.9 Hz, γ-P), −11.63 (d, J=20.0 Hz, α-P), −23.07 (s), −23.26 (t, J=19.7 Hz, β-P). MS (MALDI-TOF-, matrix: 9-aminoacridine) (m/z): [M−H]− calcd for C17H18Cl2N2O13P3S2-, 684.9, found, 685.0.

Example 3. General Procedure for PCR Amplification Assay to Determine Fidelity

Materials. Taq and OneTaq DNA polymerases were purchased from New England Biolabs (Ipswich, MA). A mixture of dNTPs was purchased from Fermentas (Glen Burnie, MD). SYBR Green I Nucleic Acid Gel Stain (10,000×) was purchased from Life Technologies (Carlsbad, CA).

DNA oligonucleotides. Complete oligonucleotide sequences are provided in Table 8. Fully natural primers were purchased from Intergrated DNA Technologies (Coralville, Iowa). Reagents and solvents for synthesis of unnatural primers 1-3 were obtained from Glen Research (Sterling, VA) and/or Applied Biosystems (Foster City, CA). The oligonucleotides were prepared using standard automated DNA synthesis with ultra-mild natural phosphoramidites (Glen Research) and dNaM phosphoramidite (Berry & Associates, Inc., Dexter, MI) on controlled pore glass supports (0.20 μmol, 1000 Å, Glen Research) and an ABI Expedite 8905 synthesizer. After automated synthesis, the oligonucleotides were cleaved from the support, deprotected by incubation in conc. aqueous ammonia overnight at room temperature, purified by DMT purification (Glen-Pak™ cartridge, Glen Research), and desalted over Sephadex G-25 (NAP-25 Columns, GE Healthcare). The concentration of single stranded oligonucleotides was determined by UV absorption at 260 nm.

PCR assay. PCR amplifications were performed in a total volume of 25 μL and with conditions specific for each assay as described in Table 9. After amplification, a 5 μL aliquot was analyzed on a 6% non-denaturing PAGE gel ran along with 50 bp ladder (Life Technologies) to confirm amplicon size. The remaining solution was purified by spin-column (DNA Clean and Concentrator-5; Zymo Research, Irvine, CA), followed by 4% agarose gel, recovered with Zymoclean Gel DNA Recovery Kit (Zymo Research), quantified by fluorescent dye binding (Quant-iT dsDNA HS Assay kit, Life Technologies), and sequenced on a 3730 DNA Analyzer (Applied Biosystems). Fidelity was determined as the average % retention of the unnatural base pair per doubling as described below.

Determination of fidelity. The percent retention of an unnatural base pair (F) was measured using raw sequencing data and normalized to fidelities per doubling. Briefly, the presence of an unnatural nucleotide leads to a sharp termination of the sequencing profile, while mutation to a natural nucleotide results in "readthrough". The extent of the "readthrough" is thus inversely correlated with the retention of the unnatural base pair. To use the sequencing data as a quantitative measurement of PCR fidelity, we performed calibration experiments in the range of 50-100% retention of the unnatural base pair. Therefore, low retention (<50%) and high "read-through" make the quantification inaccurate.

Quantification of the high retention (>50%) was performed by adjusting the start and stop points for the Sequencing Analysis software (Applied Biosystems) and then determining the average signal intensity individually for each channel (A, C, G and T) for peaks within those defined points (35-45 nucleotides in length) before (section L) and S36 after (section R) the unnatural nucleotide. The R/L ratio was normalized using sequencing calibration plots to account for both noise in the sequencing chromatograms and the read-through in the control samples. The R/L, ratio of after normalization (R/Lnorm) corresponds to the percentage of the natural sequences in the pool. Finally, F was calculated as 1−(R/L)norm and the retention of the unnatural base pair per doubling (fidelity, f) was calculated as $1/(F^{log 2A})$, where A is an amplification and log 2A is the number of doublings. Each sample before and PCR amplification was sequenced in triplicate in each direction to minimize sequencing error. Corresponding data is provided in Table 10. Under standard PCR conditions, DNA containing dTPT3-dNaM was amplified by OneTaq with an efficiency that is only 4-fold lower than that of DNA containing just the natural base pairs, and with a fidelity in excess of 99.98%. This fidelity corresponds to an error rate of $10^{-4}$ per nucleotide, which overlaps with the $10^{-4}$ to $10^{-7}$ error rate of fully natural DNA with commonly used PCR systems. With Taq polymerase, the efficiency is only 2.5-fold lower than that of a natural base pair, and the fidelity is 99.7%. This fidelity corresponds to an error rate of $10^{-3}$, which is similar to that observed with the Taq-medicated amplification of natural DNA.

TABLE 8

DNA sequences.

| Name | Sequence (5' to 3') Primer regions underlined | Remarks |
|---|---|---|
| Fend1 | CACACAGGAAACAGCTATGAC (SEQ ID NO: 1) | Primers for PCR (templates D6 and 134mer) |
| Fend2 | GAAATTAATACGACTCACTATAGG (SEQ ID NO: 2) | |
| Fend1-poly-dT | TTTTTTTTTTTTTTTTTTTTTTTTTTTTTTTTTTTTTTTTTTTTTTTTTTTTTTCACACAGGAAACAGCTATGAC (SEQ ID NO: 3) | Primers for Sanger sequencing (templates D6 and 134mer) |
| Fend2-poly-dT | TTTTTTTTTTTTTTTTTTTTTTTTTTTTTTTTTTTTTTTTTTTTTTTTTTTGAAATTAATACGACTCACTATAGG (SEQ ID NO: 4) | |
| D6 | CACACAGGAAACAGCTATGACCCGGGTTATTACATGCGCTAGCACTTGGAATTCACCAGACGNNNNaM NNNCGGGACCCATAGTAAATCTCCTTCTTAAAGTTAAGCTTAACCCTATAGTGAGTCGTATTAATTTC (SEQ ID NO: 6) | N = randomized natural nucleotide |
| 134mer | CACACAGGAAACAGCTATGACCCGGGTTATTACATGCGCTAGCACTTGGAATTCACAATACT NaM TCTTTAAGGAAACCATAGTAAATCTCCTTCTTAAAGTTAAGCTTAACCCTATAGTGAGTCGTATTAATTTC (SEQ ID NO: 5) | |
| Primer 1 | NaM CCTGCGTCAATGTAATGTTC (SEQ ID NO: 7) | Primers for PCR with Temp1-3 |
| Primer2 | TTCACGGT NaM AGCACGCATAGG (SEQ ID NO: 8) | |
| Primer3 | CCAATGTACC NaM TGCGTATGTTC (SEQ ID NO: 9) | |
| Primer-rev | CCCTGCGTTTATCTGCTCTC (SEQ ID NO: 10) | |
| Temp1 | CCCTGCGTTTATCTGCTCTCTCGGTCGTTCGGCTGCGGCGGAACATTACATTGACGCAGG (SEQ ID NO: 11) | The nucleotides shown in bold form a mispair with dNaM in the first round of PCR |
| Temp2 | CCCTGCGTTTATCTGCTCTCTCGGTCGTTCGGCTGCGCGCCTATGCGTGCTTACCGTGAA (SEQ ID NO: 12) | |
| Temp3 | CCCTGCGTTTATCTGCTCTCTCGGTCGTTCGGCTGCCGGAACATACGCATGGTACATTGG (SEQ ID NO: 13) | |

TABLE 9

PCR Conditions.

| | OneTaq | Taq | PCR for biotin labeling (unnatural base pair centrally located) | PCR for biotin labeling (unnatural base pair positioned at 1, 9, 11 positions) |
|---|---|---|---|---|
| Buffer | 1× OneTaq | 1× Taq | 1× OneTaq | 1× OneTaq |
| Enzyme, U/μL | OneTaq, 0.02 | Taq, 0.02 | OneTaq, 0.02 | OneTaq, 0.02 |
| Template | D6 (0.01 ng) | D6 (0.01 ng) | 134mer (0.5 ng) | 60mer (0.5 ng) |
| dNTPs, μM | 200 | 200 | 200 | 200 |
| dNaMTP, μM | 100 | 100 | 100 | 100 |
| dXTP, μM | 100 | 100 | 100 of d5SICS$^{PA}$TP or dTPT3$^{PA}$TP | 100 of d5SICS$^{PA}$TP or dTPT3$^{PA}$TP |
| Mg$^{2+}$, mM | 3 | 3 | 3 | 3 |
| Primers, μM | 1 | 1 | 1 | 1 |
| SYBR Green I | 0.5× | 0.5× | 0.5× | 0.5× |
| Thermal conditions | | | | |
| Initial denaturing | — | — | 96° C., 1 min | 96° C., 1 min |
| Denaturing | 96° C., 10 s | 96° C., 10 s | 96° C., 15 s | 96° C., 15 s |
| Annealing | 60° C., 15 s | 60° C., 15 s | 60° C., 30 s | 64° C., 30 s |
| Extension | 68° C., 60 s | 68° C., 15 s | 68° C., 2 min | 68° C., 2 min |
| # cycles | 16 + 16 + 16 | 20 | 12 | 12 |

TABLE 10

| dXTP | OneTaq PCR (48 cycles) | | | Taq PCR (20 cycles) | | |
|---|---|---|---|---|---|---|
| | amplification ×$10^{12}$ | retention, % | fidelity, % | amplification ×$10^{13}$ | retention, % | fidelity, % |
| 5SICS | 9.4 | 96.3 ± 1.7 | 99.91 ± 0.04 | 7.7 | 86.7 ± 1.0 | 98.90 ± 0.01 |
| TPT3 | 12.9 | >99 | >99.98 | 11.7 | 95.6 ± 1.7 | 99.66 ± 0.13 |
| TPT3$^{PA}$ | 4.7 | 98.6 ± 1.2 | 99.97 ± 0.03 | 3.5 | 85 ± 4 | 98.7 ± 0.4 |
| 5SICS$^{PA}$ | 9.2 | 45 ± 2 | 98.16 ± 0.12 | 6.4 | —[a] | —[a] |

[a]Unnatural base pair lost during amplification

Example 4: Site-Specific Labeling of TPT3: Analysis Via Streptavidin Gel Shift Assay A 134-mer DNA comprising a centrally positioned dTPT3$^{PA}$-dNaM or d5SICS$^{PA}$-dNaM was synthesized. DNA templates were amplified by PCR under the conditions described in Table 9. Upon completion, NaOH (1 M, 12.5 µL) was added directly to PCR samples to a final concentration of 0.2 M and incubated for 5 hr at room temperature. After the addition of NaOAc (3 M, pH 5.5, 7.5 µL) and 200 µL of cold ethanol, the samples were mixed, incubated on ice overnight, and DNA was precipitated by centrifugation at 10,000 rfu for 30 min at 4° C. The supernatant was removed and the pellets were carefully washed with 80% ethanol. The samples were resuspended in 50 µL of the annealing buffer (50 mM Na phosphate, pH 7.5, 100 mM NaCl, 1 mM EDTA), heated to 95° C. and cooled to room temperature over 30 min. NHS-PEG$_4$-biotin (Thermo Scientific) solution in the annealing buffer (40 mM, 50 µL) was mixed with the DNA samples and incubated overnight at room temperature. The samples were purified by spin-column (DNA Clean and Concentrator-5, Zymo Research) and eluted in 10 µL of elution buffer. Half of the sample (5 µL) was mixed with 1 µg of streptavidin (Promega) in annealing buffer, incubated for 30 min at 37° C., mixed with 5× non-denaturing loading buffer (Qiagen), and loaded on 6% non-denaturing PAGE. The remaining half was mixed with 5× non-denaturing loading buffer, and loaded directly on the gel as a control. After running the gel at 110 V for 30 min, the gel was soaked in 1× Sybr Gold Nucleic Acid Stain (Life Technologies) for 30 min and visualized using a Molecular Imager Gel Doc XR+ equipped with 520DF30 filter (Bio-Rad). A schematic of the labeling strategy described is shown below.

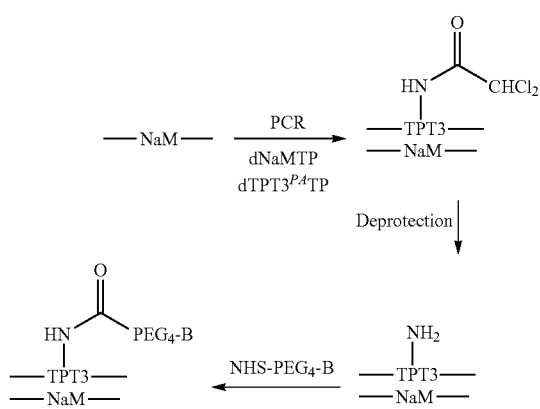

Example 5. General Procedure for Transcription of an Unnatural Base Pair

To characterize the transcription of the unnatural base pairs formed by dTPT3 and dNaM, or analogs or derivatives thereof (wherein derivatives include linker moieties), ribonucleotides and deoxynucleotides are synthesized and converted to the corresponding triphosphates or deoxyphosphoramidites, and the deoxyphosphoramidites are incorporated into DNA templates using automated DNA synthesis. Transcription experiments are conducted with 100 nM DNA substrate, 1× Takara buffer (40 mM Tris-HCl, pH 8.0, 8 mM MgCl$_2$, 2 mM spermidine), DEPC-treated and nuclease-free sterilized water (Fisher), T7 polymerase (50 units), 20 µM each natural NTP, α-$^{32}$P-ATP (2.5 µCi, MP Biomedicals), and either 5 µM TPT3TP or 5 µM NamTP. After incubation for 2 hr at 37° C., the reaction is quenched by the addition of 10 µL of gel loading solution (10 M urea, 0.05% bromophenol blue), and the reaction mixture is loaded onto a 20% polyacrylamide-7 M urea gel, subjected to electrophoresis, and analyzed by phosphorimaging. Transcription efficiency is examined by measuring (at low percent conversion) the amount of full-length product formed as a function of time.

Example 6. General Procedure for Thermodynamic Analysis of a DNA Duplex Comprising an Unnatural Base Pair UV melting experiments are carried out using a Cary 300 Bio UV-visible spectrophotometer. The absorbance of a sample (3 µL oligonucleotide comprising an unnatural base pair, 10 mM PIPES buffer, pH 7.0, 100 mM NaCl, 10 mM MgCl$_2$) is monitored at 260 nm from 21° C. to 80° C. at a heating rate of 0.5° C. per min. Melting temperatures are determined via the derivative method using the Cary Win UV thermal application software.

Thermodynamic parameters are determined by van't Hoff analysis $T_m^{-1} = R[\ln([C_T]/4)]\Delta H + \Delta S°/\Delta H°$, where $\Delta H°$ and $\Delta S°$ are the standard enthalpy and entropy changes determined from UV experiments, respectively, R is the universal gas constant and $[C_T]$ is the total oligonucleotide strand concentration. The changes in the number of water molecules associated with the melting process, $\Delta n_w$, are obtained from the dependence of $T_m$ on water activity ($\alpha_w$) according to the equation $\Delta n_w = (-\Delta H/R)[\delta(T_m^{-1})/\delta(\ln \alpha_w)]$. The slope of the plot of reciprocal temperature ($K^{-1}$) of melting versus the logarithm of water activity at different concentrations (0, 2, 5, 7, 10, 12 and 15% wt %) of ethylene glycol is taken as the value of $\delta(T_m^{-1})/\delta(\ln \alpha_w)$.

CD experiments are performed with an Aviv model 61 DS spectropolarimeter equipped with a Peltier thermoelectric temperature control unit (3 µM oligonucleotide concentration, 10 mM PIPES buffer, pH 7.0, 100 mM NaCl, 10 mM MgCl$_2$). The data are collected using a 1 cm path length quartz cuvette with scanning from 360 to 220 nm, a time constant of 3 s and a wavelength step size of 0.5 nm at 25° C.

Example 7. In Vitro Selection with Unnatural Nucleobases

An oligonucleotide library comprising unnatural nucleic acids is generated. A sample of the library is subjected to sequential binding and elution from a target molecule, for example, a protein. The pool of binding nucleic acids are amplified by PCR and subjected to another round of selection for binding to the target molecule. This selection process is repeated a number of times. To increase selection pressure, in the last few rounds of selection, the concentration of target molecule and/or incubation time is reduced. Surviving nucleic acids are sequenced as potential aptamers. The binding affinities of potential aptamers are determined using flow-cytometry.

Example 8. General Procedure for DNA Click Reaction

To a DNA solution (0.2 pmol) in 14 µL DMSO was added 1 µL azide-PEG(3+3)—S—S-Biotin(20 mM in H$_2$O), followed by 2 µL of ligand (BimC$_4$A)$_3$(4 mM in H$_2$O), 1 µL of sodium ascorbate (100 mM in H$_2$O), and 1 µL of PBS buffer (5×), the mixture was then vortexed and as the last component, 1 µL of a freshly prepared CuSO$_4$ solution (4 mM in H$_2$O) was added. The solution was shaken for 2 h at 37° C., and then the resulting product DNA was purified (DNA Clean & Concentrator-5 kit, Zymo Research Corp.). The purified samples were used directly for gel mobility assays (see below).

Example 9. General Procedures for Post-Amplification DNA Labeling (From Seo et al., JACS 2011, 133, 19878)

For post-enzymatic synthesis labeling, dsDNA with a free amino group was incubated with 10 mM EZ-Link sulfo-NHS—SS-biotin or EZ-Link NHS-PEG4-biotin (Thermo Scientific) for 1 h at rt in phosphate labeling buffer (50 mM sodium phosphate, pH 7.5, 150 mM NaCl, 1 mM EDTA), and then purified using the Qiagen PCR purification kit. With either dichloroacetyl protected amine derivatives such as dTPT3$^{PA}$ or d5SICS$^{PA}$, the amine first required deprotection, which was accomplished by overnight incubation in a concentrated aqueous ammonia solution at rt. Ammonia was removed via a SpeedVac concentrator (water aspirator followed by oil vacuum pump). To cleave the disulfide containing linkers (i.e. SS-biotin or SS-PEG$_4$-biotin), dsDNA was treated with DTT (final concentration of 30 mM) for 1 hour at 37° C. For backbone labeling, dsDNA with a backbone phosophorothioate was incubated with 25 mM EZ-Link iodoacetyl-PEG$_2$-biotin (Thermo Scientific) in phosphate labeling buffer overnight at 50° C., and products were purified with Qiagen PCR Purification Kit. All reactions manipulating attached biotin moieties were quantified by streptavidin gel-shift assays.

Gel Mobility Assays. DNA samples (10-50 ng) were mixed with 1 µg of streptavidin (Promega) in phosphate labeling buffer (50 mM sodium phosphate, pH 7.5, 150 mM NaCl, 1 mM EDTA), incubated for 30 min at 37° C., mixed with 5× nondenaturing loading buffer (Qiagen), and loaded on 6% nondenaturing PAGE. The gel was run at 150 V for 25-40 min, then stained with 1× Sybr Gold Nucleic Acid Stain (Life Technologies) in TBE for 30 min and visualized using a Molecular Imager Gel Doc XR+ equipped with 520DF30 filter (Bio-Rad). Strong bands corresponding to dsDNA (at ~150 bp) and the 1:1 complex between dsDNA and streptavidin (at ~400 bp) were apparent. Faint bands corresponding to higher order (slower migrating) complexes of DNA and streptavidin or from unbiotinylated, single-stranded DNA resulting from incomplete annealing after PCR in some cases were also apparent.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present embodiments have been specifically disclosed by preferred embodiments and optional features, modification and variation of the concepts herein disclosed may be resorted to by those skilled in the art, and that such modifications and variations are considered to be within the scope of this disclosure as defined by the appended claims.

What is claimed is:

1. A nucleobase pair comprising a first nucleobase analog having the structure β9b, and a second nucleobase analog having any of the structures α15a or α15b:

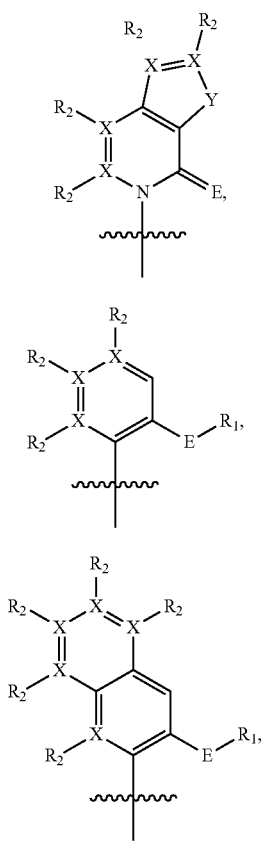

β9b

α15a

α15b wherein each X is independently carbon or nitrogen,
wherein each $R_1$ is independently hydrogen, alkyl group, a reactive linker comprising a reactive center a linker coupled to a cargo,
wherein each $R_2$ is optional and when present is independently hydrogen, alkyl, alkenyl, alkynyl, methoxy, methanethiol, methaneseleno, halogen, cyano, azide, nitro group, a reactive linker comprising a reactive center, or a linker coupled to a cargo,
wherein each Y is independently sulfur, oxygen, selenium, or a secondary amine,
wherein each E is independently oxygen, sulfur or selenium,
and the wavy line indicates a point of bonding to a ribosyl, deoxyribosyl, or dideoxyribosyl moiety or an analog thereof, wherein the ribosyl, deoxyribosyl, or dideoxyribosyl moiety, or analog thereof is in free form, is bound to a mono-phosphate, diphosphate, triphosphate, α-thiotriphosphate, β-thiophosphate, or γ-thiophosphate group, or is included in an RNA or a DNA or in an RNA analog or a DNA analog.

2. A double-stranded oligonucleotide comprising the nucleobase pair of claim 1.

3. The nucleobase pair of claim 1, wherein the ribosyl, deoxyribosyl, or dideoxyribosyl moiety or analog thereof is included in an RNA.

4. The nucleobase pair of claim 1, wherein the ribosyl, deoxyribosyl, or dideoxyribosyl moiety or analog thereof is included in a DNA.

5. The nucleobase pair of claim 1, wherein each X in structure β9b is carbon.

6. The nucleobase pair of claim 1, wherein each $R_2$ in structure β9b is hydrogen.

7. The nucleobase pair of claim 1, wherein Y is sulfur.

8. The nucleobase pair of claim 7, wherein E in structure β9b is sulfur.

9. The nucleobase pair of claim 1, wherein the first nucleobase analog is

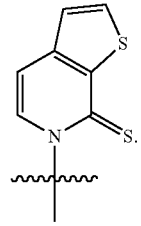 [SMILES: *n1ccc2ccsc2c1=S]

10. The nucleobase pair of claim 1, wherein the first nucleobase analog is

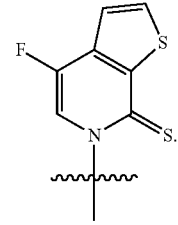

11. The nucleobase pair of claim 1, wherein each X in structure α15b and α15a is carbon.

12. The nucleobase pair of claim 1, wherein the second nucleobase analog has the structure α15b.

13. The nucleobase pair of claim 12, wherein $R_1$ in structure α15b is methyl.

14. The nucleobase pair of claim 13, wherein E in structure α15b is oxygen.

15. The nucleobase pair of claim 12, wherein each $R_2$ in structure α15b is hydrogen.

16. The nucleobase pair of claim 12, wherein the second nucleobase analog is

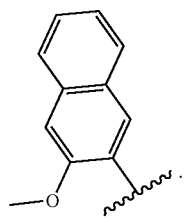 [SMILES: *c1cc2ccccc2cc1OC]

17. The nucleobase pair of claim 1, wherein the second nucleobase analog has the structure α15a.

18. The nucleobase pair of claim 17, wherein at least one R₂ is CN.

19. The nucleobase pair of claim 17, wherein R₁ in structure α15a is methyl.

20. The nucleobase pair of claim 19, wherein E in structure α15a is oxygen.

21. The nucleobase pair of claim 17, wherein the second nucleobase analog is

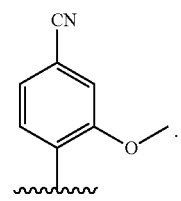 [SMILES: *c1ccc(C#N)cc1OC]

22. The nucleobase pair of claim 1, wherein the second nucleobase analog has any of the structures

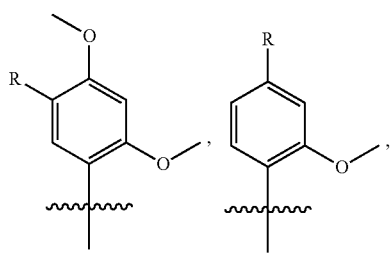

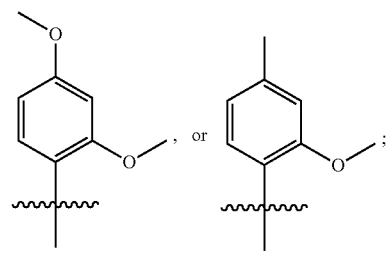

wherein each R is independently hydrogen, or the reactive linker.

23. The nucleobase pair of claim 1, wherein the first nucleobase analog is

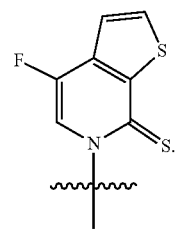

24. The nucleobase pair of claim 23, wherein the second nucleobase analog is

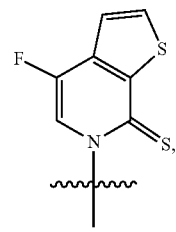

25. The nucleobase pair of claim 1, wherein the first nucleobase analog is

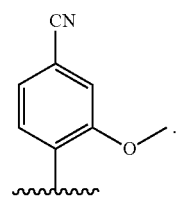 [SMILES: *c1ccc(C#N)cc1OC]

and the second nucleobase analog is

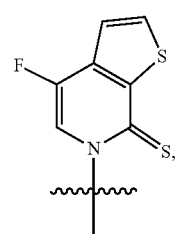

26. The nucleobase pair of claim 1, wherein the first nucleobase analog is and the second nucleobase analog is

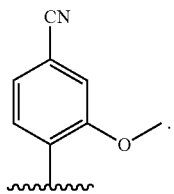 [SMILES: *c1ccc(C#N)cc1OC]

27. The nucleobase pair of claim 1, wherein the first nucleobase analog is

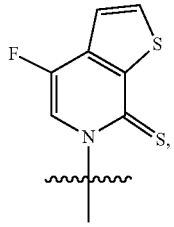

and the second nucleobase analog is

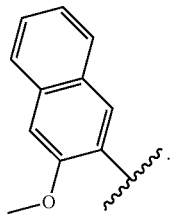 [SMILES: *c1cc2ccccc2cc1OC]

28. The nucleobase pair of claim 1, 7, or 8, wherein at least one $R_2$ in structure β9b is halogen.

29. The nucleobase pair of claim 8, wherein each X in structure β9b is carbon.

30. The nucleobase pair of claim 1, wherein the first nucleobase analog is

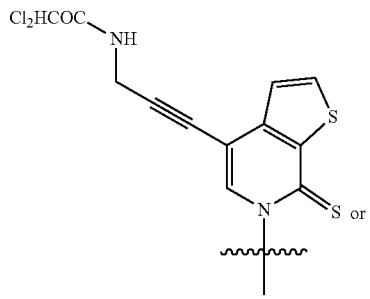

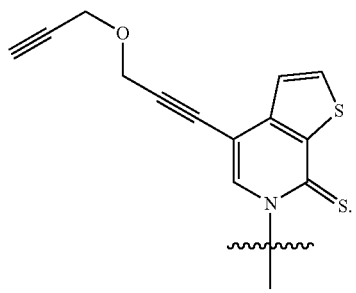

31. The nucleobase pair of claim 1, wherein the first nucleobase analog is

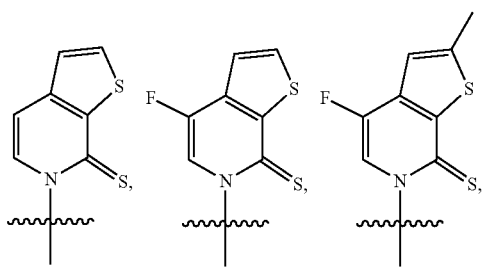

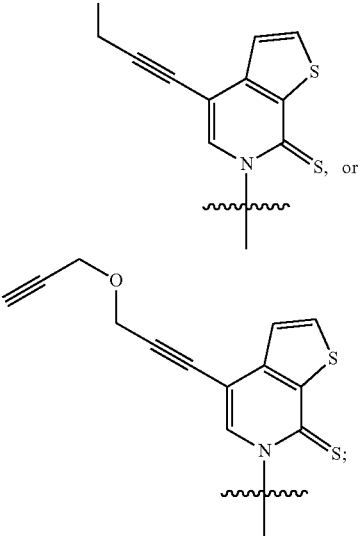

and the second nucleobase analog is

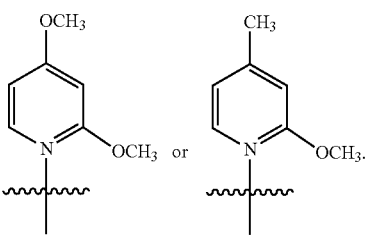

32. A nucleobase pair comprising a first nucleobase analog having the structure and a second nucleobase analog having the structure

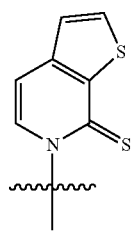 [SMILES: *n1ccc2ccsc2c1=S]

and a second nucleobase analog having the structure

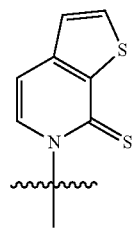

wherein the wavy line indicates a point of bonding to a ribosyl, deoxyribosyl, or dideoxyribosyl moiety, wherein the ribosyl, deoxyribosyl, or dideoxyribosyl moiety (i) has its 5'-hydroxy group in free form or bound to a mono-phosphate, diphosphate, triphosphate, α-thiotriphosphate, β-thiophosphate, γ-thiophosphate group, or (ii) is included in an RNA or a DNA.

33. A nucleobase pair comprising a first nucleobase analog having the structure

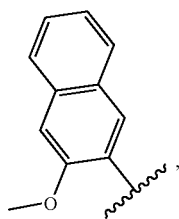 [SMILES: *c1cc2ccccc2cc1OC ; ","]

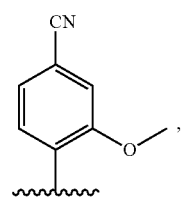 [SMILES: *c1ccc(C#N)cc1OC ; ","]

wherein the wavy line indicates a point of bonding to a ribosyl, deoxyribosyl, or dideoxyribosyl moiety, wherein the ribosyl, deoxyribosyl, or dideoxyribosyl moiety (i) has its 5'-hydroxy group in free form or bound to a mono-phosphate, diphosphate, triphosphate, α-thiotriphosphate, β-thiophosphate, or γ-thiophosphate group, or (ii) is included in an RNA or a DNA.

34. A double-stranded oligonucleotide comprising the nucleobase pair of claim 32.

35. A double-stranded oligonucleotide comprising the nucleobase pair of claim 33.

* * * * *

SEQUENCE LISTING

```
Sequence total quantity: 16
SEQ ID NO: 1            moltype = DNA  length = 21
FEATURE                 Location/Qualifiers
source                  1..21
                        mol_type = other DNA
                        organism = synthetic construct
SEQUENCE: 1
cacacaggaa acagctatga c                                               21

SEQ ID NO: 2            moltype = DNA  length = 24
FEATURE                 Location/Qualifiers
source                  1..24
                        mol_type = other DNA
                        organism = synthetic construct
SEQUENCE: 2
gaaattaata cgactcacta tagg                                            24

SEQ ID NO: 3            moltype = DNA  length = 80
```

```
FEATURE                 Location/Qualifiers
source                  1..80
                        mol_type = other DNA
                        organism = synthetic construct
SEQUENCE: 3
tttttttttt tttttttttt tttttttttt tttttttttt tttttttttt tttttttttc   60
acacaggaaa cagctatgac                                               80

SEQ ID NO: 4            moltype = DNA  length = 85
FEATURE                 Location/Qualifiers
source                  1..85
                        mol_type = other DNA
                        organism = synthetic construct
SEQUENCE: 4
tttttttttt tttttttttt tttttttttt tttttttttt tttttttttt tttttttttt   60
tgaaattaat acgactcact atagg                                         85

SEQ ID NO: 5            moltype = DNA  length = 134
FEATURE                 Location/Qualifiers
modified_base           63
                        mod_base = OTHER
                        note =
                        ((2R,3S,5R)-2-(Hydroxymethyl)-5-(3-methoxynaphthalen-2-yl)o
                        xolan-3-ol)
source                  1..134
                        mol_type = other DNA
                        organism = synthetic construct
SEQUENCE: 5
cacacaggaa acagctatga cccgggttat tacatgcgct agcacttgga attcacaata   60
ctntctttaa ggaaaccata gtaaatctcc ttcttaaagt taagcttaac cctatagtga  120
gtcgtattaa tttc                                                    134

SEQ ID NO: 6            moltype = DNA  length = 134
FEATURE                 Location/Qualifiers
modified_base           66
                        mod_base = OTHER
                        note =
                        ((2R,3S,5R)-2-(Hydroxymethyl)-5-(3-methoxynaphthalen-2-yl)o
                        xolan-3-ol)
source                  1..134
                        mol_type = other DNA
                        organism = synthetic construct
SEQUENCE: 6
cacacaggaa acagctatga cccgggttat tacatgcgct agcacttgga attcaccaga   60
cgnnnnnnnc gggacccata gtaaatctcc ttcttaaagt taagcttaac cctatagtga  120
gtcgtattaa tttc                                                    134

SEQ ID NO: 7            moltype = DNA  length = 21
FEATURE                 Location/Qualifiers
modified_base           1
                        mod_base = OTHER
                        note =
                        ((2R,3S,5R)-2-(Hydroxymethyl)-5-(3-methoxynaphthalen-2-yl)o
                        xolan-3-ol)
source                  1..21
                        mol_type = other DNA
                        organism = synthetic construct
SEQUENCE: 7
ncctgcgtca atgtaatgtt c                                             21

SEQ ID NO: 8            moltype = DNA  length = 21
FEATURE                 Location/Qualifiers
modified_base           9
                        mod_base = OTHER
                        note =
                        ((2R,3S,5R)-2-(Hydroxymethyl)-5-(3-methoxynaphthalen-2-yl)o
                        xolan-3-ol)
source                  1..21
                        mol_type = other DNA
                        organism = synthetic construct
SEQUENCE: 8
ttcacggtna gcacgcatag g                                             21

SEQ ID NO: 9            moltype = DNA  length = 22
FEATURE                 Location/Qualifiers
modified_base           11
                        mod_base = OTHER
                        note =
                        ((2R,3S,5R)-2-(Hydroxymethyl)-5-(3-methoxynaphthalen-2-yl)o
```

```
                        xolan-3-ol)
source                  1..22
                        mol_type = other DNA
                        organism = synthetic construct
SEQUENCE: 9
ccaatgtacc ntgcgtatgt tc                                            22

SEQ ID NO: 10           moltype = DNA  length = 20
FEATURE                 Location/Qualifiers
source                  1..20
                        mol_type = other DNA
                        organism = synthetic construct
SEQUENCE: 10
ccctgcgttt atctgctctc                                               20

SEQ ID NO: 11           moltype = DNA  length = 60
FEATURE                 Location/Qualifiers
source                  1..60
                        mol_type = other DNA
                        organism = synthetic construct
SEQUENCE: 11
ccctgcgttt atctgctctc tcggtcgttc ggctgcggcg aacattaca ttgacgcagg    60

SEQ ID NO: 12           moltype = DNA  length = 60
FEATURE                 Location/Qualifiers
source                  1..60
                        mol_type = other DNA
                        organism = synthetic construct
SEQUENCE: 12
ccctgcgttt atctgctctc tcggtcgttc ggctgcgcgc ctatgcgtgc ttaccgtgaa   60

SEQ ID NO: 13           moltype = DNA  length = 60
FEATURE                 Location/Qualifiers
source                  1..60
                        mol_type = other DNA
                        organism = synthetic construct
SEQUENCE: 13
ccctgcgttt atctgctctc tcggtcgttc ggctgccgga acatacgcat ggtacattgg   60

SEQ ID NO: 14           moltype = DNA  length = 21
FEATURE                 Location/Qualifiers
source                  1..21
                        mol_type = other DNA
                        organism = synthetic construct
SEQUENCE: 14
ataatacgac tcactatagg g                                             21

SEQ ID NO: 15           moltype = DNA  length = 35
FEATURE                 Location/Qualifiers
modified_base           5
                        mod_base = OTHER
                        note =
                        (2R,3S,5R)-2-(Hydroxymethyl)-5-(3-methoxynaphthalen-2-yl)ox
                        olan-3-ol) or
                        2-[(2R,4S,5R)-4-Hydroxy-5-(hydroxymethyl)oxolan-2-yl]-6-met
                        hylisoquinoline-1(2H)-thione
source                  1..35
                        mol_type = other DNA
                        organism = synthetic construct
SEQUENCE: 15
cactnctcgg gattccctat agtgagtcgt attat                              35

SEQ ID NO: 16           moltype = RNA  length = 17
FEATURE                 Location/Qualifiers
modified_base           13
                        mod_base = OTHER
                        note = MMO2, MMO2 with a protecting group, MMO2 with a
                        propargyl amine,
                        (2-[(2R,4S,5R)-4-Hydroxy-5-(hydroxymethyl)oxolan-2-yl]-6-me
                        thylisoquinoline-1(2H)-thione),
                        (2-[(2R,4S,5R)-4-Hydroxy-5-(hydroxymethyl)oxolan-2-yl]-6-me
                        thylisoquinoline-1(2H)-thione) with a protecting group, or
                        (2-[(2R,4S,5R)-4-Hydroxy-5-(hydroxymethyl)oxolan-2-yl]-6-me
                        thylisoquinoline-1(2H)-thione) with a propargyl amine
source                  1..17
                        mol_type = other RNA
                        organism = synthetic construct
```

-continued

SEQUENCE: 16
gggaatcccg agnagtg      17